US012642442B2

(12) United States Patent
Barnacka et al.

(10) Patent No.: US 12,642,442 B2
(45) Date of Patent: Jun. 2, 2026

(54) SYSTEM AND METHOD FOR CARDIOVASCULAR MONITORING AND REPORTING

(71) Applicants: Anna Barnacka, Cambridge, MA (US); Charles R Bridges, Auburndale, MA (US); Siddharth Patel, Allston, MA (US)

(72) Inventors: Anna Barnacka, Cambridge, MA (US); Charles R Bridges, Auburndale, MA (US); Siddharth Patel, Allston, MA (US)

( * ) Notice: Subject to any disclaimer, the term of this patent is extended or adjusted under 35 U.S.C. 154(b) by 391 days.

(21) Appl. No.: 18/500,895

(22) Filed: Nov. 2, 2023

(65) Prior Publication Data

US 2024/0065605 A1      Feb. 29, 2024

Related U.S. Application Data

(63) Continuation of application No. 16/991,990, filed on Aug. 12, 2020, now Pat. No. 11,844,618.

(51) Int. Cl.
A61B 5/316 (2021.01)
A61B 5/00 (2006.01)
(Continued)

(52) U.S. Cl.
CPC .............. A61B 5/316 (2021.01); A61B 5/021 (2013.01); A61B 5/318 (2021.01); A61B 5/6815 (2013.01);
(Continued)

(58) Field of Classification Search
CPC ......... A61B 5/316; A61B 5/318; A61B 5/021; A61B 5/6815; A61B 5/7246;
(Continued)

(56) References Cited

U.S. PATENT DOCUMENTS

| | | | |
|---|---|---|---|
| 10,646,121 | B2 | 5/2020 | Narasimhan et al. |
| 2011/0125063 | A1 | 5/2011 | Shalon et al. |

(Continued)

FOREIGN PATENT DOCUMENTS

| | | |
|---|---|---|
| WO | WO2019019119 | 1/2019 |
| WO | WO2019019119 A1 | 1/2019 |
| WO | PCT/US2019/017832 | 8/2019 |

OTHER PUBLICATIONS

Canada Application No. 3,150,852 filed on Aug. 12, 2020, based upon Int'l app. No. PCT/2020/046021: Office Action dated Feb. 22, 2024 from the Canada Intellectual Property Office (CIPO); 4 pages.

(Continued)

*Primary Examiner* — Jennifer Robertson
*Assistant Examiner* — Om Patel
(74) *Attorney, Agent, or Firm* — Gillis Patent Law, LLC; John Gillis

(57) ABSTRACT

A system and method for cardiovascular monitoring and reporting are disclosed. The system (CV monitoring system) includes a data analysis system and an in-ear biosensor system that preferably includes left and right earbuds. The earbuds include infrasound/vibration sensors that detect biosignals from the individual including signals associated with cardiovascular activity (CV signals). The analysis system calculates cardiovascular function measurements (CV function measurements) based upon the CV signals. The CV monitoring system uses machine learning to predict blood pressure (BP) measurements of the individual based upon the CV signals and the calculated CV function measurements. In an embodiment, the CV monitoring system includes an EKG detection system that detects EKG signals associated with heart function. The analysis system can calculate additional CV function measurements from the EKG signals to augment the CV function measurements (Continued)

| baseline CV data 930/user CV data 950 | | | | | | |
|---|---|---|---|---|---|---|
| CV signals 101 | stacked CV signal 101S | | user app version 964 | | | 952-1 |
| MVC 201 | AVO 202 | AVC 203 | systolic peak 218 | diastolic peak 220 | elasticity index 412 | 954-1 |
| IVC 207 | LVET 208 | IVR period 211 | stroke volume (SV) 210 | VC period 301 | inflection point 222 | vascular aging index 414 |
| measured systolic BP 370 | measured diastolic BP 372 | measured mean arterial pressure 374 | predicted systolic BP 376 | predicted diastolic BP 378 | predicted mean arterial pressure 380 | 956-1 |

630-1
time stamp 602-1

⋮

| CV signals 101 | stacked CV signal 101S | | user app version 964 | | | 952-1 |
|---|---|---|---|---|---|---|
| MVC 201 | AVO 202 | AVC 203 | systolic peak 218 | diastolic peak 220 | elasticity index 412 | 954-N |
| IVC 207 | LVET 208 | IVR period 211 | stroke volume (SV) 210 | VC period 301 | inflection point 222 | vascular aging index 414 |
| measured systolic BP 370 | measured diastolic BP 372 | measured mean arterial pressure 374 | predicted systolic BP 376 | predicted diastolic BP 378 | predicted mean arterial pressure 380 | 956-N |

630-N
Time stamp 602-N calculated from the CV signals, and predict BP measurements using the full complement of CV function measurements.

25 Claims, 26 Drawing Sheets

(51) Int. Cl.

| | |
|---|---|
| *A61B 5/021* | (2006.01) |
| *A61B 5/318* | (2021.01) |
| *G16H 10/60* | (2018.01) |

(52) U.S. Cl.
CPC .......... *A61B 5/7246* (2013.01); *A61B 5/7264* (2013.01); *A61B 5/7275* (2013.01); *A61B 5/7465* (2013.01); *G16H 10/60* (2018.01)

(58) Field of Classification Search
CPC ... A61B 5/7264; A61B 5/7275; A61B 5/7465; A61B 5/02116; A61B 5/6817; G16H 10/60; G16H 15/00; G16H 50/20; G16H 80/00; G16H 50/30
See application file for complete search history.

(56) References Cited

U.S. PATENT DOCUMENTS

| | | |
|---|---|---|
| 2016/0051150 A1 | 2/2016 | Aarts |
| 2017/0135633 A1 | 5/2017 | Connor |
| 2018/0001184 A1 | 1/2018 | Tran et al. |
| 2018/0235540 A1 | 8/2018 | Kirszenblat et al. |
| 2019/0247010 A1 | 8/2019 | Barnacka et al. |
| 2019/0343480 A1* | 11/2019 | Shute .................. A61B 5/7203 |

OTHER PUBLICATIONS

Canada Application No. 3,150,852 filed on Aug. 12, 2020, based upon Int'l app. No. PCT/2020/046021: Notice of Allowance dated Oct. 14, 2025 from the Canada Intellectual Property Office (CIPO); 2 pages.

EP Application No. 20852885.1 filed on Aug. 12, 2020, based upon Int'l app. No. PCT/2020/046021: Examination Report dated Jul. 27, 2025 from the European Patent Office (EPO); 5 pages.

Supplementary European Search Report, mailed on Jul. 27, 2023, from related EP application No. EP20852885 filed on Mar. 4, 2022. Two (2) pages.

Supplementary European Search Opinion, mailed on Jul. 27, 2023, from related EP application No. EP20852885 filed on Mar. 4, 2022. Three (3) pages.

International Search Report, mailed on Nov. 19, 2020, from related International application PCT/ US2020/046021, filed on Aug. 20, 2020. Two (2) pages.

Written Opinion, mailed on Nov. 19, 2020, from related International application PCT/US2020/046021, filed on Aug. 20, 2020. Five (5) pages.

\* cited by examiner

| medical record 50 |
|---|
| user data (e.g. name, address, telephone) 902 |
| biometric data (e.g. age, weight, height) 904 |
| baseline cardiovascular (CV) data 930 |
| user CV data 950 |
| normal ranges of cardiovascular (CV) function measurements 932 |
| normal ranges of blood pressure (BP) measurements 934 |
| threshold percentage change values of the CV function measurements 936 |
| threshold percentage change values of the BP measurements 938 |

FIG. 4A

| user account 60 |
|---|
| credentials (e.g. user/password, biometric ID) 960 |
| in-ear biosensor system version 962 |
| user application (user app) version 964 |
| system calibration data 966 |

FIG. 4B

Figure 5A:
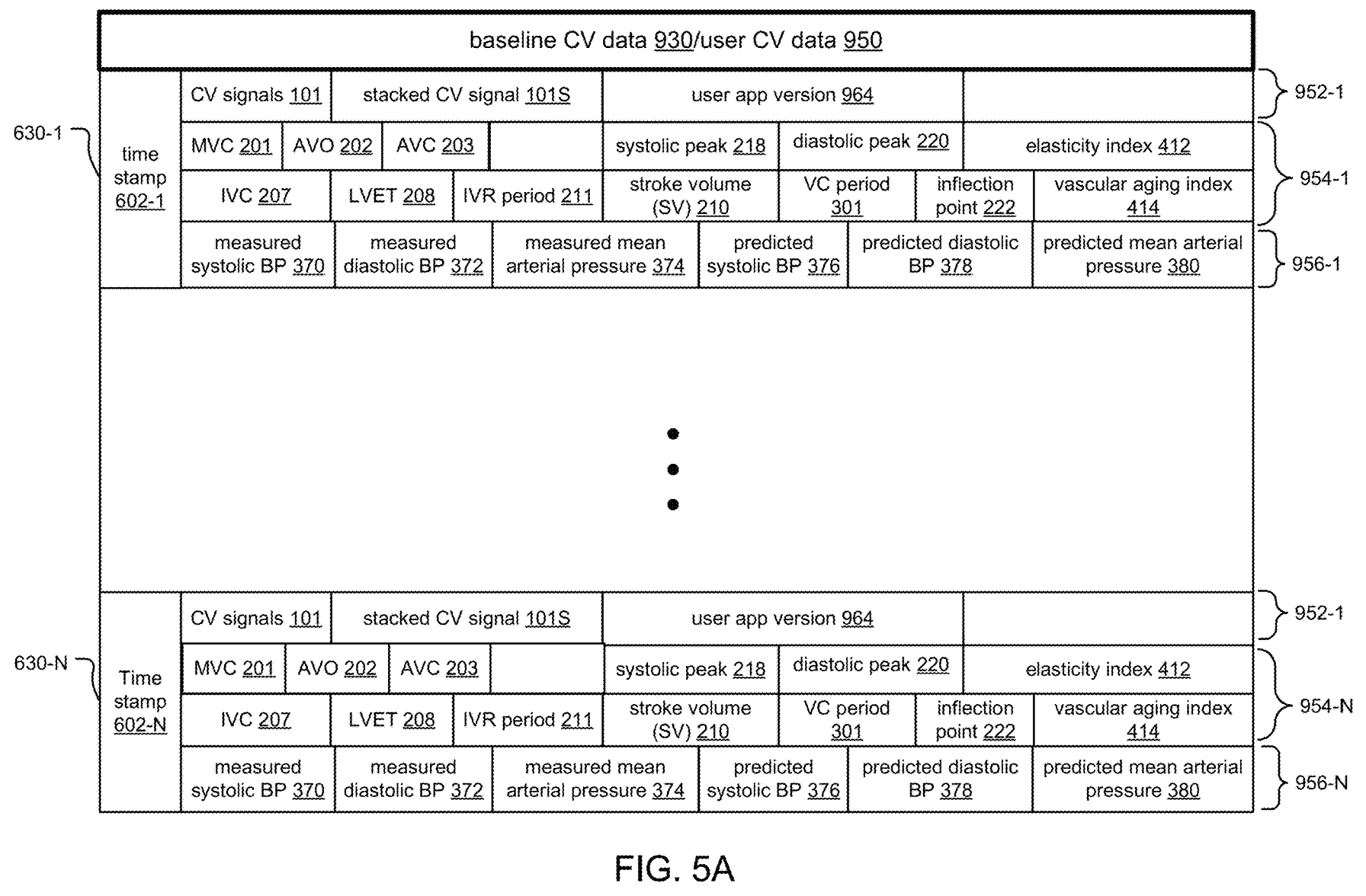

| baseline CV data 930/user CV data 950 | | | | | | | | | | |
|---|---|---|---|---|---|---|---|---|---|---|
| | CV signals 101 | stacked CV signal 101S | | | user app version 964 | | | | | |
| | | | | | | elasticity index 412 | | | | |
| time stamp 602-1 | MVC 201 | AVO 202 | AVC 203 | | systolic peak 218 | diastolic peak 220 | | vascular aging index 414 | | |
| | IVC 207 | LVET 208 | IVR period 211 | | stroke volume (SV) 210 | VC period 301 | inflection point 222 | predicted mean arterial pressure 380 | | |
| | measured systolic BP 370 | measured diastolic BP 372 | measured mean arterial pressure 374 | | predicted systolic BP 376 | predicted diastolic BP 378 | | | | |
| 952-1 | | | | | 954-1 | | | 956-1 | | |

● ● ●

| | CV signals 101 | stacked CV signal 101S | | | user app version 964 | | | | | |
|---|---|---|---|---|---|---|---|---|---|---|
| | | | | | | elasticity index 412 | | | | |
| Time stamp 602-N | MVC 201 | AVO 202 | AVC 203 | | systolic peak 218 | diastolic peak 220 | | vascular aging index 414 | | |
| | IVC 207 | LVET 208 | IVR period 211 | | stroke volume (SV) 210 | VC period 301 | inflection point 222 | predicted mean arterial pressure 380 | | |
| | measured systolic BP 370 | measured diastolic BP 372 | measured mean arterial pressure 374 | | predicted systolic BP 376 | predicted diastolic BP 378 | | | | |
| 952-1 | | | | | 954-N | | | 956-N | | |

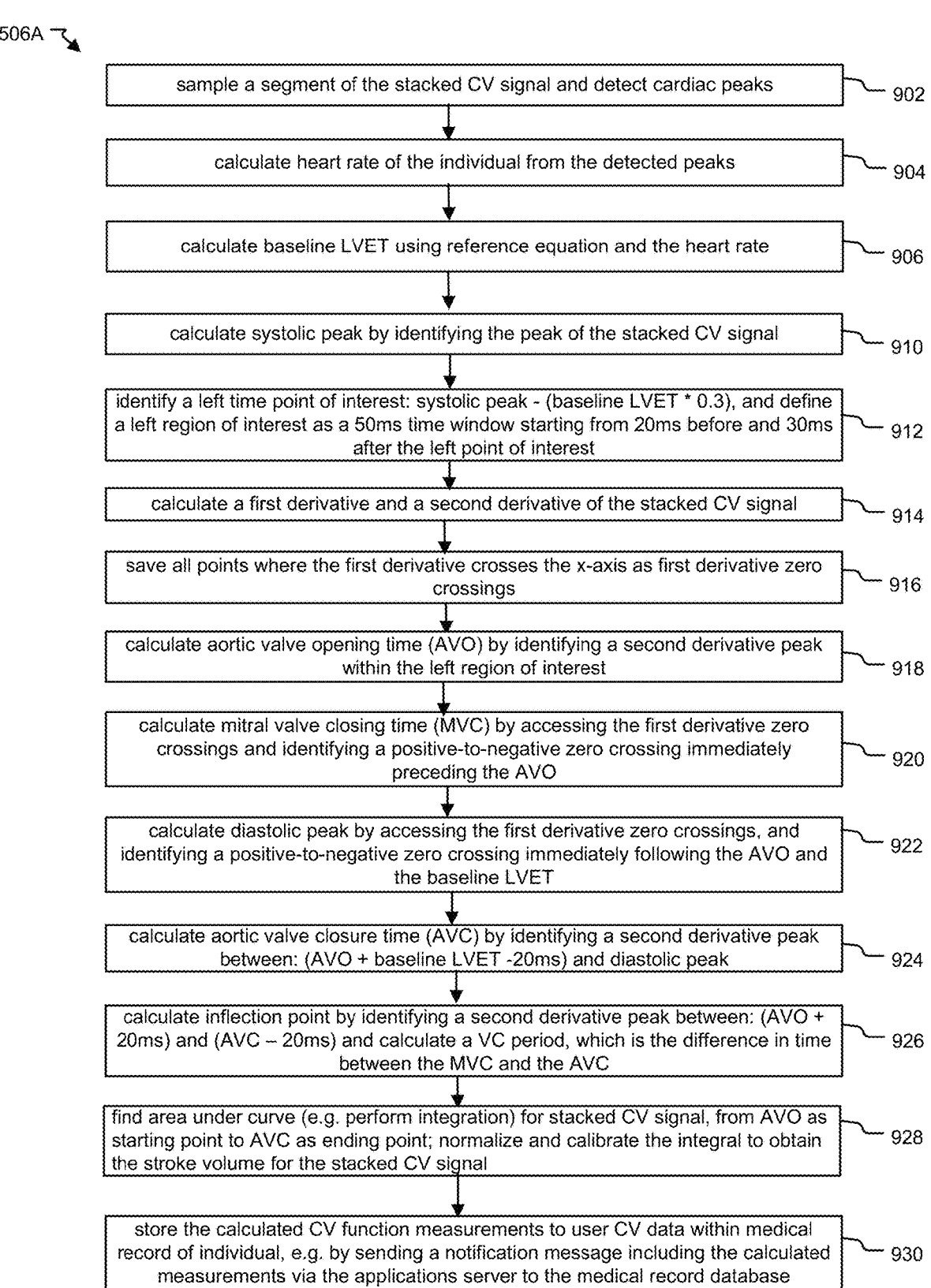

sample a segment of the stacked CV signal and detect cardiac peaks — 902 calculate heart rate of the individual from the detected peaks — 904 calculate baseline LVET using reference equation and the heart rate — 906 calculate systolic peak by identifying the peak of the stacked CV signal — 910 identify a left time point of interest: systolic peak - (baseline LVET * 0.3), and define a left region of interest as a 50ms time window starting from 20ms before and 30ms after the left point of interest — 912 calculate a first derivative and a second derivative of the stacked CV signal — 914 save all points where the first derivative crosses the x-axis as first derivative zero crossings — 916 calculate aortic valve opening time (AVO) by identifying a second derivative peak within the left region of interest — 918 calculate mitral valve closing time (MVC) by accessing the first derivative zero crossings and identifying a positive-to-negative zero crossing immediately preceding the AVO — 920 calculate diastolic peak by accessing the first derivative zero crossings, and identifying a positive-to-negative zero crossing immediately following the AVO and the baseline LVET — 922 calculate aortic valve closure time (AVC) by identifying a second derivative peak between: (AVO + baseline LVET -20ms) and diastolic peak — 924 calculate inflection point by identifying a second derivative peak between: (AVO + 20ms) and (AVC – 20ms) and calculate a VC period, which is the difference in time between the MVC and the AVC — 926 find area under curve (e.g. perform integration) for stacked CV signal, from AVO as starting point to AVC as ending point; normalize and calibrate the integral to obtain the stroke volume for the stacked CV signal — 928 store the calculated CV function measurements to user CV data within medical record of individual, e.g. by sending a notification message including the calculated measurements via the applications server to the medical record database — 930

FIG. 8

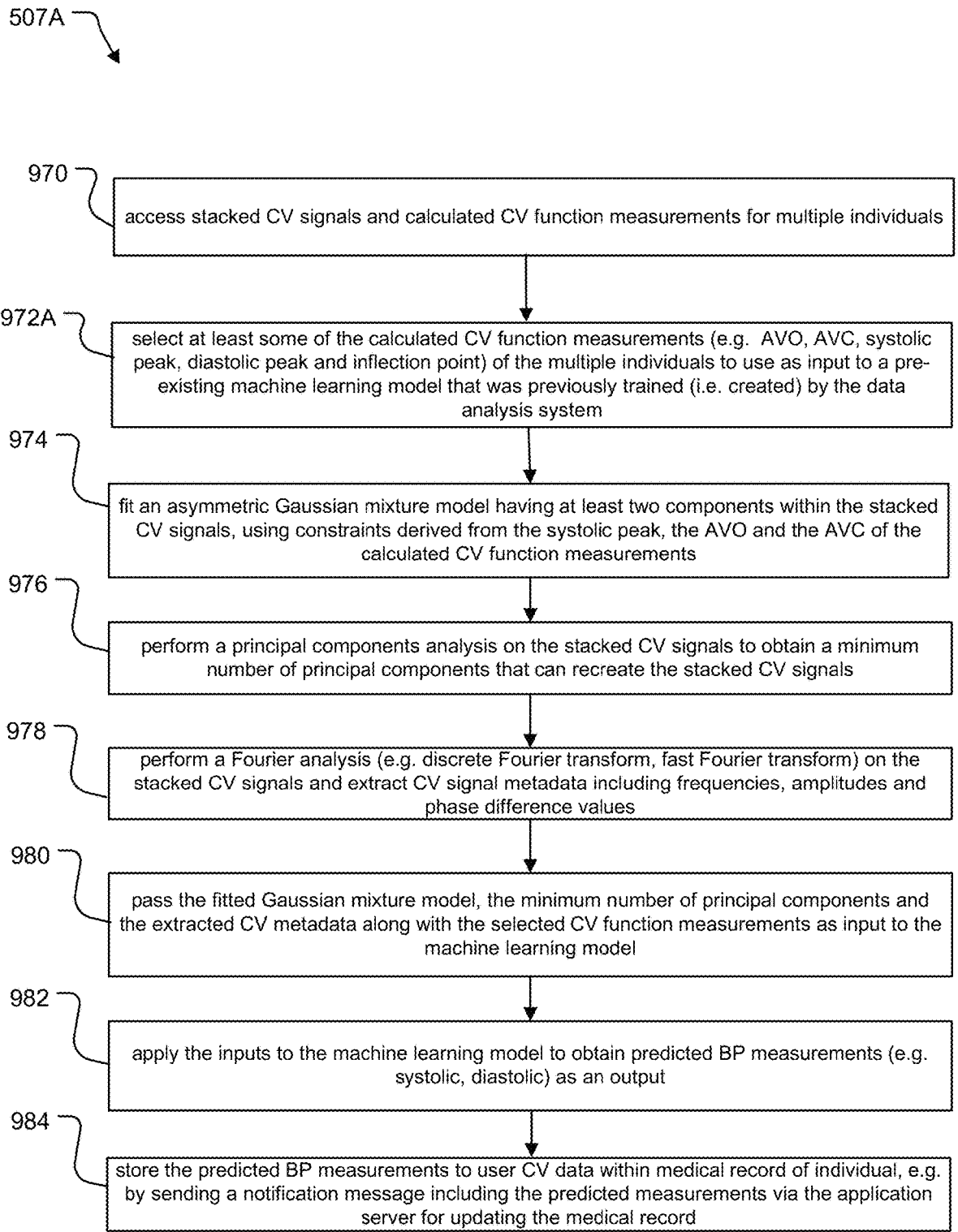

507A

970 — access stacked CV signals and calculated CV function measurements for multiple individuals 972A — select at least some of the calculated CV function measurements (e.g. AVO, AVC, systolic peak, diastolic peak and inflection point) of the multiple individuals to use as input to a pre-existing machine learning model that was previously trained (i.e. created) by the data analysis system 974 — fit an asymmetric Gaussian mixture model having at least two components within the stacked CV signals, using constraints derived from the systolic peak, the AVO and the AVC of the calculated CV function measurements 976 — perform a principal components analysis on the stacked CV signals to obtain a minimum number of principal components that can recreate the stacked CV signals 978 — perform a Fourier analysis (e.g. discrete Fourier transform, fast Fourier transform) on the stacked CV signals and extract CV signal metadata including frequencies, amplitudes and phase difference values 980 — pass the fitted Gaussian mixture model, the minimum number of principal components and the extracted CV metadata along with the selected CV function measurements as input to the machine learning model 982 — apply the inputs to the machine learning model to obtain predicted BP measurements (e.g. systolic, diastolic) as an output 984 — store the predicted BP measurements to user CV data within medical record of individual, e.g. by sending a notification message including the predicted measurements via the application server for updating the medical record

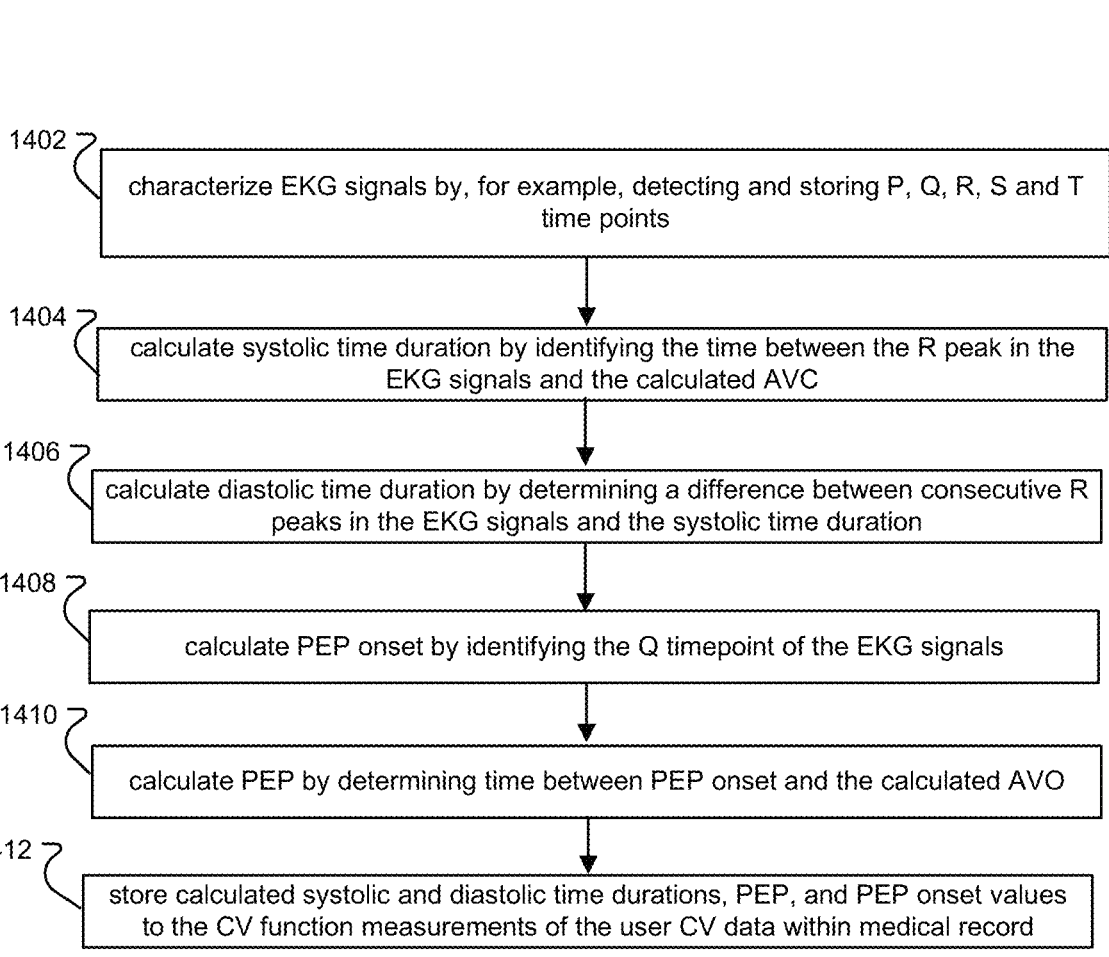

1402   characterize EKG signals by, for example, detecting and storing P, Q, R, S and T time points 1404   calculate systolic time duration by identifying the time between the R peak in the EKG signals and the calculated AVC 1406   calculate diastolic time duration by determining a difference between consecutive R peaks in the EKG signals and the systolic time duration 1408   calculate PEP onset by identifying the Q timepoint of the EKG signals 1410   calculate PEP by determining time between PEP onset and the calculated AVO 1412   store calculated systolic and diastolic time durations, PEP, and PEP onset values to the CV function measurements of the user CV data within medical record

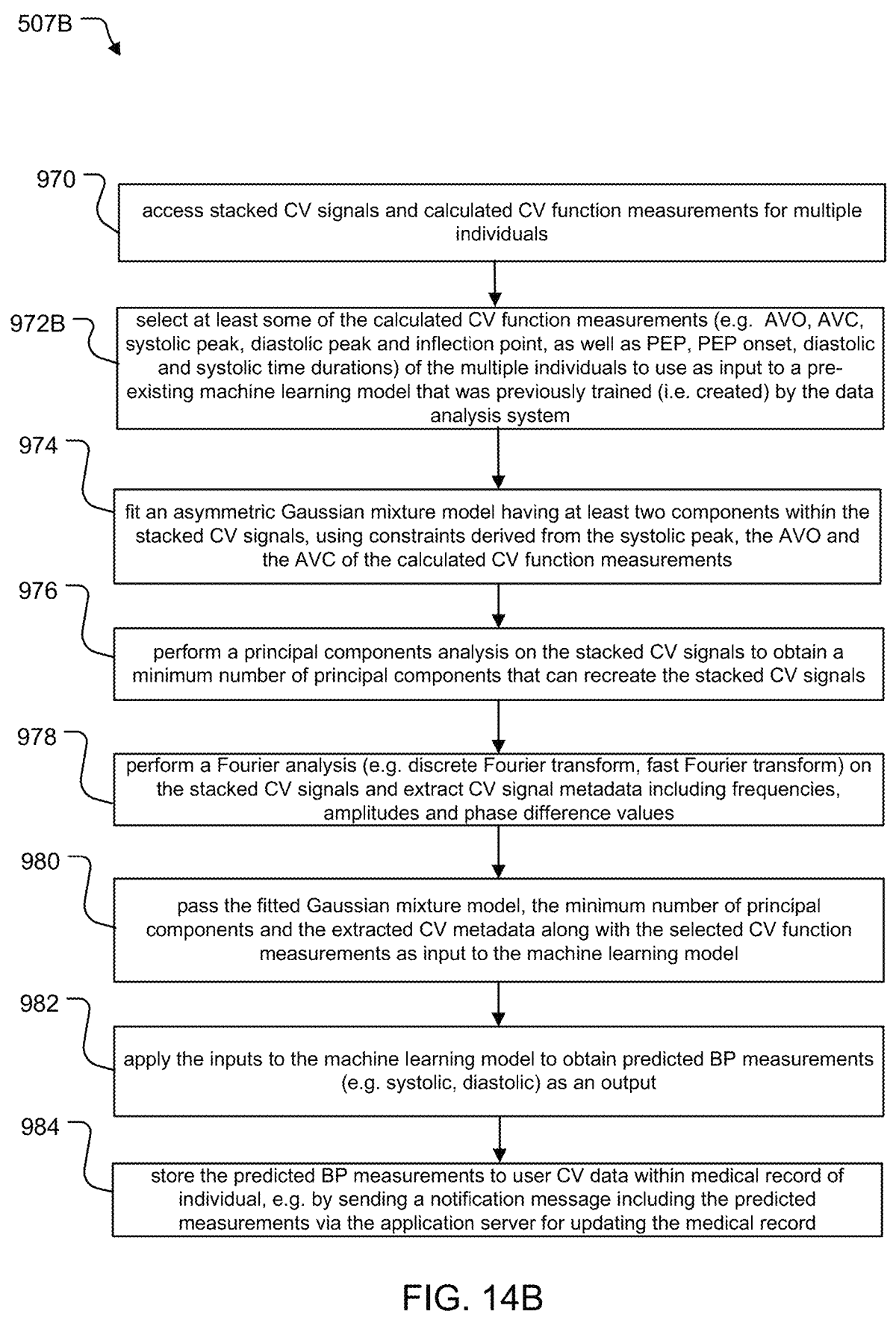

970 — access stacked CV signals and calculated CV function measurements for multiple individuals 972B — select at least some of the calculated CV function measurements (e.g. AVO, AVC, systolic peak, diastolic peak and inflection point, as well as PEP, PEP onset, diastolic and systolic time durations) of the multiple individuals to use as input to a pre-existing machine learning model that was previously trained (i.e. created) by the data analysis system 974 — fit an asymmetric Gaussian mixture model having at least two components within the stacked CV signals, using constraints derived from the systolic peak, the AVO and the AVC of the calculated CV function measurements 976 — perform a principal components analysis on the stacked CV signals to obtain a minimum number of principal components that can recreate the stacked CV signals 978 — perform a Fourier analysis (e.g. discrete Fourier transform, fast Fourier transform) on the stacked CV signals and extract CV signal metadata including frequencies, amplitudes and phase difference values 980 — pass the fitted Gaussian mixture model, the minimum number of principal components and the extracted CV metadata along with the selected CV function measurements as input to the machine learning model 982 — apply the inputs to the machine learning model to obtain predicted BP measurements (e.g. systolic, diastolic) as an output 984 — store the predicted BP measurements to user CV data within medical record of individual, e.g. by sending a notification message including the predicted measurements via the application server for updating the medical record

FIG. 14B

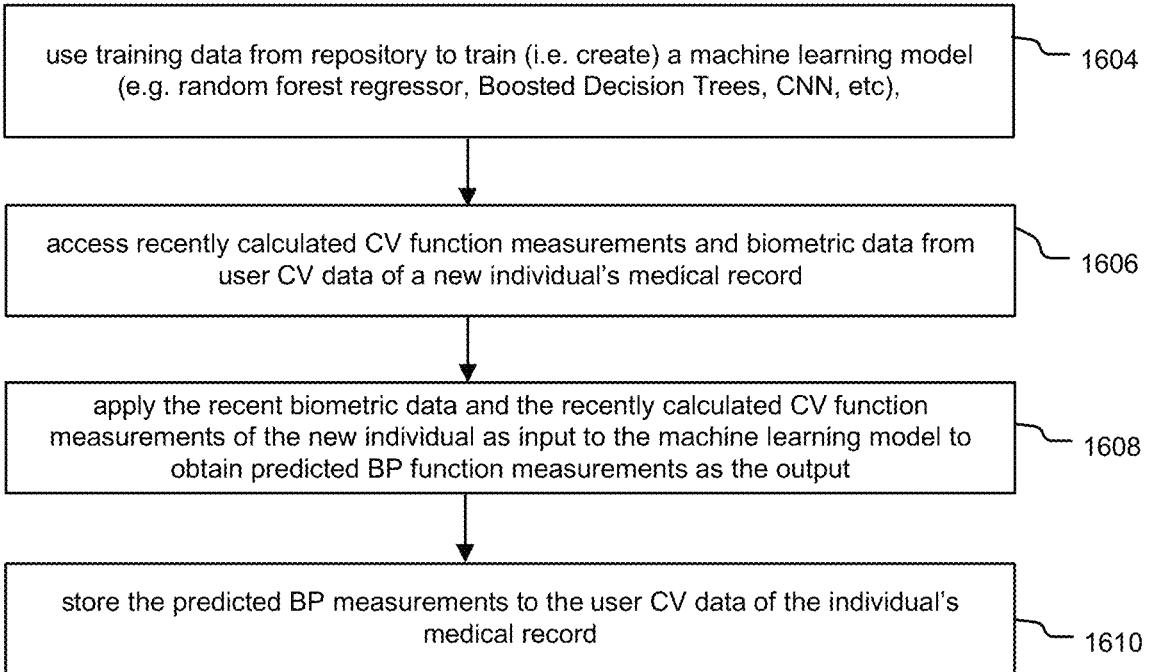

use training data from repository to train (i.e. create) a machine learning model (e.g. random forest regressor, Boosted Decision Trees, CNN, etc), — 1604 access recently calculated CV function measurements and biometric data from user CV data of a new individual's medical record — 1606 apply the recent biometric data and the recently calculated CV function measurements of the new individual as input to the machine learning model to obtain predicted BP function measurements as the output — 1608 store the predicted BP measurements to the user CV data of the individual's medical record — 1610

FIG. 16A

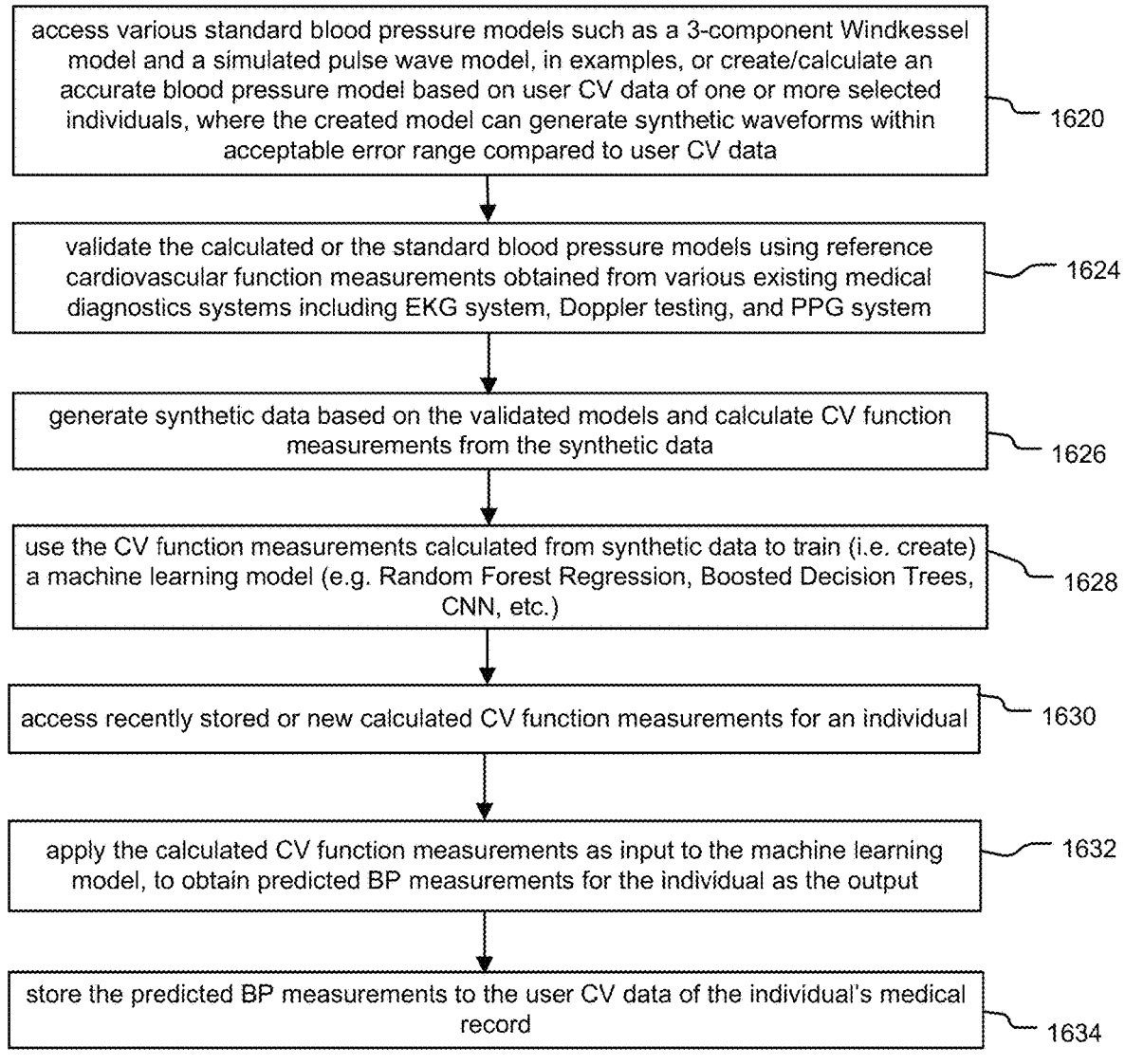

access various standard blood pressure models such as a 3-component Windkessel model and a simulated pulse wave model, in examples, or create/calculate an accurate blood pressure model based on user CV data of one or more selected individuals, where the created model can generate synthetic waveforms within acceptable error range compared to user CV data ⟍ 1620 validate the calculated or the standard blood pressure models using reference cardiovascular function measurements obtained from various existing medical diagnostics systems including EKG system, Doppler testing, and PPG system ⟍ 1624 generate synthetic data based on the validated models and calculate CV function measurements from the synthetic data ⟍ 1626 use the CV function measurements calculated from synthetic data to train (i.e. create) a machine learning model (e.g. Random Forest Regression, Boosted Decision Trees, CNN, etc.) ⟍ 1628 access recently stored or new calculated CV function measurements for an individual ⟍ 1630 apply the calculated CV function measurements as input to the machine learning model, to obtain predicted BP measurements for the individual as the output ⟍ 1632 store the predicted BP measurements to the user CV data of the individual's medical record ⟍ 1634

FIG. 16B

SYSTEM AND METHOD FOR CARDIOVASCULAR MONITORING AND REPORTING

RELATED APPLICATIONS

This application is a continuation of U.S. patent application Ser. No. 16/991,990 filed on Aug. 12, 2020, which claims the benefit under 35 USC 119(e) of the following previously filed applications: U.S. Provisional Application No. 62/885,364 filed on Aug. 12, 2019; U.S. Provisional Application No. 62/888,067 filed on Aug. 16, 2019; and U.S. Provisional Application No. 62/888,075 filed on Aug. 16, 2019, all three of which are incorporated herein by reference in their entirety.

This application is related to:

U.S. application Ser. No. 16/274,873, filed on Feb. 13, 2019, entitled "INFRASOUND BIOSENSOR SYSTEM AND METHOD," now U.S. Patent Publication No. 2019/0247010A1; and International Application number PCT/US2019/017832, entitled "INFRASOUND BIOSENSOR SYSTEM AND METHOD," now International Application Publication No. WO2019/160939A2.

FIELD OF THE INVENTION

The present invention generally relates to the field of noninvasive cardiovascular function monitoring. In particular, the present invention is directed to a system and method for cardiovascular function detection, analysis and reporting.

BACKGROUND OF THE INVENTION

The heart of an individual is a muscular organ about the size of a first and has various components. These components include valves and chambers. The chambers include two atria, left and right, and two ventricles, left and right. The heart is located just behind and slightly left of the breastbone of the individual.

The heart pumps blood throughout the individual's body via a network of blood vessels including arteries, arterioles, capillaries, venules and veins. The blood vessels and the heart form a closed-loop system for circulating the blood throughout the body, also known as the cardiovascular system. Function and status of the cardiovascular system is essential to human health. For this reason, medical professionals use various medical diagnostics systems to detect and monitor operation of the cardiovascular systems of individuals. These systems include an electrocardiogram system (ECG/EKG system), echocardiogram system (echo system), phonocardiogram system (PCG system), and a sphygmomanometer (BP cuff system), in examples. Other, more invasive systems exist, including a doppler-based system, an Impedance Cardiography (ICG) system, a Holter monitor that is applied externally to monitor the heart for 24 hours up to 7 days continuously, and an implantable loop recorder that is installed subcutaneously to monitor the heart for up to three years.

The medical diagnostics systems generally operate as follows. The systems acquire different types of signal data associated with cardiovascular operation of individuals over multiple cardiac cycles. The systems then derive information concerning operation of the heart and its components from the signal data. This information is also known as cardiovascular function measurements (CV function measurements). Of these systems, the EKG system is the standard for determining many of the CV function measurements.

In the EKG system, a medical professional places multiple electrodes on the skin of the individual to detect electrical changes associated with cardiovascular operation. As many as 12 electrodes or more are attached to various locations on the skin near the torso, the heart and the upper arms, in examples. The individual is at rest during the procedure, which typically takes one minute or less after the electrodes are attached. The electrical changes across multiple successive cardiac cycles are recorded or plotted to form an electrocardiogram (ECG/EKG). The EKG system (or its operator) then derives the CV function measurements from the detected electrical signals. The EKG system might also include a display to present the signals obtained during the test (e.g. an electrocardiogram) for viewing by the medical professional, and a printer that can print the electrocardiogram.

Arterial blood pressure, or blood pressure, is the pressure that the blood exerts upon walls of the arteries in the cardiovascular system. The strength or force of this pressure can be detected and measured over time. These blood pressure measurements (BP measurements) include systolic and diastolic BP measurements which are measured in units of millimeters of mercury, or mmHg. The systolic BP measurement, or systolic BP, refers to the pressure detected in the arteries while the heart is actively pumping, i.e. in its systole phase. The diastolic BP measurement, or diastolic BP, refers to the pressure detected in the arteries while the heart is at rest, i.e. in its diastole phase. As a shorthand, the BP measurements taken at a particular instance in time are usually expressed in terms of the systolic BP "over" the diastolic BP.

Medical professionals use reference BP monitoring systems to accurately obtain the BP measurements of individuals. These systems meet the clinical standard of less than 5 mmHg of error in the obtained BP measurements. These reference systems include a BP cuff system and a catheter system. The BP cuff system is a non-intrusive device that includes a pressure-inflating device (e.g. manual inflation bulb or battery powered pump) with a release valve, a cuff with an inflatable bladder and a measuring device. The catheter is an intrusive device that includes a catheter connected to a measuring device.

The BP cuff system is the standard non-invasive measure of BP. Here, the cuff is typically worn around the individual's upper arm for obtaining BP measurements via the brachial artery. In traditional (i.e. manual) versions of the system, the cuff is typically attached to a column of mercury with a graduated scale in mmHg as the measuring device. In modern BP cuff systems, the measuring device is a combination of the cuff and a digital monitoring unit with a display. The monitoring unit also operates as the pressure-inflating device. The cuff additionally includes sensors that detect the changes in pressure using principles of oscillometry. Here, the sensors in the cuff detect changes in the applied pressure and varying amplitudes of blood volume oscillations as a function of the pressure, and report the oscillations in digital format to the monitoring unit. The monitoring unit then derives the BP measurements from the digitized oscillations and presents the measurements on its display.

The catheter system provides more precise BP measurements than the BP cuff system, but is invasive and must be performed in a clinical setting. The system requires insertion of its catheter into a large artery or vein of the individual as an entry site. This system is typically reserved for diagnosing issues with BP and cardiac function for critically ill individuals. In this system, the catheter is directed from the entry site into the heart through one of the heart valves. In one example, a Swan-Ganz catheter is used to measure venous BP and the BP of the pulmonary artery. Most importantly, this catheter is also used to measure cardiac output via the pulmonary artery using a technique known as thermodilution.

An individual's BP measurements are best obtained when the individual is at rest. A normal resting BP measurement consists of a systolic BP in the range of 90-120 mmHg and a diastolic BP that is in the range of 60-80 mmHg. In particular, a systolic BP of 120 mmHg and diastolic BP of 80 mmHg, often referred to "120 over 80," are considered to be the typical average BP measurements for healthy adult individuals.

An individual's resting BP measurements are an important indicator of cardiovascular health and thus overall health of an individual. When the resting BP measurements are considered to be unhealthy/outside the normal ranges, this is often an indicator of various health problems including cardiovascular disease, stroke and diabetes, in examples. In particular, if the BP measurements are consistently higher than their normal ranges, this is known as hypertension. Hypertension is usually associated with resting systolic BP that is consistently above 120 mmHg and resting diastolic BP that is consistently above 80 mmHg.

Over the last 30 years, various new BP monitoring systems have been proposed. These systems have claimed to provide accurate BP measurements while also providing improved portability and lower cost. In general, these systems include wearable devices that use photoplethysmography (PPG) sensors placed against the individual's skin. The sensors use optical signals to detect blood volume pulsations at the skin and convert the detected pulsations to associated waveforms. The devices then send the waveforms for analysis to predict the BP measurements based upon the waveforms. Example PPG-based BP monitoring systems include a fingertip pulse oximeter, and an Apple Watch 4 device made by Apple, Inc.

More recently, two wearable devices have been proposed from Apple, Inc. that claim the ability to measure blood pressure of individuals. These devices do not include PPG sensors. The first device is an Apple Watch 5 device introduced in 2019 that operates in conjunction with a consumer-oriented (i.e. non-clinical), modern BP cuff system that is separate from the watch device. In the Apple Watch 5 device, the separate BP cuff system obtains the blood pressure measurements and sends the measurements in digital form via a wireless link for presentation at a display of the watch. The second device is a proposed self-contained wrist worn device.

The disclosed second device includes a watchband that has capacitive tactile sensors arranged against the individual's skin. The device claims that its sensors can detect changes in arterial pressure and present blood pressure measurements on a display of the device. In one embodiment, the device additionally includes actuators in the watchband. The actuators apply varied levels of pressure to the sensors to urge the sensors against the individual's skin using principles of applanation tonometry. The device claims that its actuator-enhanced version can improve upon the accuracy of the arterial pressure detected by its sensors.

SUMMARY OF THE INVENTION

Biosignals are signals in living beings such as individuals that can be detected, observed and/or measured. Examples of biosignals from individuals include acoustic signals, pressure signals, thermal signals and electrical signals, to name a few. The acoustic signals are created as a result of breathing and physical/mechanical operations within the individual's body. These operations include blood flow throughout the cardiovascular system, and opening and closing of valves within the heart and the blood vessels, in examples. These acoustic signals can be in either the infrasonic range (infrasonic signals) or in the audible range (audible signals) or both. The pressure signals are created by pressure or tension within the body. The thermal signals are created in response to physical and biochemical processes within the body. The electrical signals are associated with changes in electrical current over time, across a specialized tissue, organ, or cell system such as the nervous system.

The existing medical diagnostics systems have limitations. In one example, even the non-invasive versions of these systems require that the individual attend a clinical setting/doctor's office in person. The standard EKG system, for example, requires a trained technician or medical professional to attach and place the multiple electrodes on the individual's skin and to operate the system. This is time-intensive and increases cost. In another example, the systems are "one shot" systems: they monitor the cardiovascular function of the individual for only a specific period of time, typically two minutes or less. In yet another example, these systems are susceptible to "white coat syndrome," which is named for the white laboratory coats that doctors and other medical professionals often wear in clinical and patient settings. When individuals attend in-office visits with their doctor or other medical professional, the individuals often exhibit anxiety that can artificially elevate their CV function measurements. In yet other examples, the invasive versions of the medical diagnostics systems are expensive, require extended hospital stays and/or multiple clinical office visits, and have a risk of vascular or cardiac perforation, bleeding, infection and even death in some rare instances.

The reference BP monitoring systems also have limitations. These systems present various levels of convenience, cost, discomfort and usage. While the catheter system is the most accurate and can monitor BP continuously, even while the individual is sleeping, it is expensive, invasive and requires hospitalization or an extended visit in a clinical setting. While the BP cuff system is non-invasive, portable, and some modern versions may not require an office visit, it is a "one shot" system that obtains BP measurements of a short time period of typically two minutes or less, and generally cannot be used while the individual is sleeping. The reference BP monitoring systems are also susceptible to white coat syndrome which can artificially elevate the obtained BP measurements. This can result in false indications of hypertension, in one example.

The BP monitoring systems that have been proposed over the last 30 years also have limitations. Though non-invasive, they are less accurate than and consistently provide lower values for the BP measurements as compared to those obtained by the reference BP monitoring systems. These proposed systems are also susceptible to motion of the individuals, interference from environmental factors such as light and wireless signals and typically have implicit assumptions about individual physiology, in examples. Even slight motion by the individuals can introduce significant motion artifacts into the detected waveforms, which reduces accuracy of the blood pressure measurements.

The two recently proposed wearable devices for obtaining BP measurements also have limitations. The Apple Watch 5 device merely displays the blood pressure measurements obtained by a separate, consumer-oriented BP cuff system. The separate BP cuff system must be periodically calibrated and must also be validated by Apple, Inc. for use with its Apple Watch 5 device, which limits wider use and deployment of the device. The proposed self-contained wrist worn device discloses that it may "increase the adoption of non-clinical measurements and monitoring of blood pressure by common consumers," an admission that its accuracy is less than that of the reference BP monitoring systems. See U.S. patent Ser. No. 10/646,121B2, Summary section. Moreover, its allegedly most accurate embodiment uses an actuator to continuously urge the sensors against the skin of the individual in a sweep-like fashion when obtaining the blood pressure measurements. This increases complexity, reduces battery life, and increases cost.

It is therefore an object of the present invention to provide a non-invasive cardiovascular monitoring system (CV monitoring system) that can calculate CV function measurements of individuals over any time period, with an accuracy that approaches that of the existing medical diagnostics systems such as the EKG system. Most importantly, the proposed CV monitoring system can calculate a superset of CV function measurements of an individual in a single system that uses a wearable biosensor system device. The superset of CV function measurements include various measurements such as a left ventricle ejection time (LVET), a systolic peak, and heart valve opening and closing times that until now could only be obtained by using a combination of multiple different medical diagnostics systems, each of which obtains separate and distinct subsets of the CV function measurements and requires an in-person visit to a clinic or medical office to obtain the measurements.

The proposed CV monitoring system is also much less expensive than the existing medical diagnostics systems, and can securely report its calculated measurements and update medical records with the measurements in real-time while the individual is in the comfort of their home. The proposed CV monitoring system can also minimize or eliminate white coat syndrome.

The CV function measurements that the proposed system calculates from the CV signals are associated with cardiovascular activity of individuals, and include various directly or indirectly calculated measurements. To calculate the measurements, the data analysis system typically creates an in-memory representation of the signals, and identifies information including features of and points in time within the representation. The data analysis system then extracts values associated with this information to obtain some of the direct CV function measurements, and performs various mathematical or statistical operations upon the information to obtain other direct measurements. For example, one direct CV measurement is a systolic peak, which the analysis system calculates by identifying a peak (amplitude) of a CV signal and then extracts its value to obtain the systolic peak. Another direct CV function measurement might be a first derivative of the CV signal.

The indirect CV function measurements, in contrast, are generally derived from the direct CV function measurements. In one example, a ventrical contraction period (VC period) is an indirect measurement that the data analysis system calculates as a difference in time between a mitral valve closing time (MVC) direct measurement and an atrial valve closing time (AVC) direct measurement. Still other indirect CV function measurements are calculated by applying various mathematical and/or statistical operations to one or more of the direct CV function measurements. These calculated CV function measurements, both direct and indirect, are then passed to the data analysis system to predict BP measurements of the individuals.

The proposed CV monitoring system has still other advantages. The proposed system can also predict BP measurements based on the CV function measurements with an accuracy that approaches that of the reference BP monitoring systems such as the BP cuff system and do so at a lower cost. The proposed CV monitoring system is also passive and non-interventional, which increases reliability and lowers cost. Moreover, because the proposed CV monitoring system can continuously monitor individuals in the comfort of their own home over any time frame and report the results in real-time, the system can detect previously undiagnosed cardiovascular disease when the individuals may not be experiencing symptoms or discomfort. This capability is especially advantageous in light of the fact that many cardiovascular disorders such as hypertension and atrial fibrillation are present in asymptomatic individuals, and earlier detection of these diseases is a significant benefit. In addition, the proposed CV system can filter motion artifacts from the biosignals/CV signals prior to analyzing the signals, or can selectively decide not to use some signals in the analysis if they include artifacts above a predetermined amplitude or content threshold.

In general, according to one aspect, the invention features a cardiovascular monitoring and reporting system (CV monitoring system). The CV monitoring system includes an in-ear biosensor system and a data analysis system. The biosensor system includes at least one earbud placed at or within an ear canal of an individual. The at least one earbud includes one or more infrasound/vibration sensors that detect biosignals including cardiovascular signals (CV signals) from the individual. The data analysis system receives the biosignals including the CV signals from the biosensor system and calculates cardiovascular function measurements (CV function measurements) of the individual based upon the CV signals. The data analysis system also predicts blood pressure measurements (BP measurements) of the individual based upon the CV signals and the calculated CV function measurements.

In one implementation, the data analysis system is included within the biosensor system. In an embodiment, the CV monitoring system also includes an electrocardiography (EKG) detection system that detects EKG signals associated with cardiovascular activity of the individual and sends the EKG signals to the data analysis system. The data analysis system can then calculate additional CV function measurements based upon the EKG signals.

In another implementation, the EKG detection system is included within the biosensor system. Typically, the data analysis system updates a medical record of the individual over time with the CV signals, the EKG signals, the calculated CV function measurements and the predicted BP measurements.

Preferably, the data analysis system compares the calculated CV function measurements to stored standard normal ranges and individual-specific normal ranges for each of the CV function measurements, identifies possible heart conditions based on the comparisons and other defined qualifying criteria, and notifies the individual and/or at least one medical professional in response. Then, in response to the comparisons and the other defined qualifying criteria, the data analysis system can notify the individual to engage in self-help activities including the need to rest, and to contact medical professionals for follow-up, in examples.

In a similar vein, the data analysis system also compares the predicted BP measurements to stored standard normal ranges and individual-specific normal ranges for each of the BP measurements, identifies possible health conditions including hypertension and hypotension based on the comparisons and other defined qualifying criteria, and can notify the individual and at least one medical professional in response. In one example, the data analysis system can notify the individual to engage in self-help activities including stress management based on the comparisons and the other defined qualifying criteria. The data analysis system then updates a medical record of the individual over time with the CV signals, the calculated CV function measurements and the predicted BP measurements.

The data analysis system can also create a machine learning model from training data, and applies the CV signals and the calculated CV function measurements of the individual as input to the model to obtain the predicted BP measurements of the individual as output of the model. In one example, the training data includes anonymized versions of calculated CV function measurements and/or CV signals copied from medical records of multiple individuals, along with corresponding reference BP measurements of the multiple individuals obtained from one or more reference BP monitoring systems. In another example, the training data includes CV function measurements and corresponding BP measurements calculated from waveforms generated from one or more blood pressure models.

In general, according to another aspect, the invention features a method for monitoring cardiovascular health of an individual. The method detects biosignals including cardiovascular signals (CV signals) from the individual, via one or more infrasound/vibration sensors included within at least one earbud of an in-ear biosensor system worn by the individual; calculates cardiovascular function measurements (CV function measurements) of the individual based upon the CV signals; and predicts blood pressure measurements (BP measurements) of the individual based upon the CV signals and the calculated CV function measurements.

The method additionally receives EKG signals associated with cardiovascular activity of the individual, detected by and sent from an EKG detection system, and calculates additional CV function measurements based upon the EKG signals.

Typically, the method compares the calculated CV function measurements to stored standard normal ranges and individual-specific normal ranges for each of the CV function measurements, identifies possible heart conditions based on the comparisons and other defined qualifying criteria, and notifies the individual and/or at least one medical professional in response. Additionally, the method notifies the individual to engage in self-help activities including the need to rest, and to contact medical professionals for follow-up.

In addition, the method compares the predicted BP measurements to stored standard normal ranges and individual-specific normal ranges for each of the BP measurements, identifies possible health conditions including hypertension and hypotension based on the comparisons and other defined qualifying criteria, and notifies the individual and/or at least one medical professional in response. The method can also notify the individual to engage in self-help activities including stress management based on the comparisons.

In one implementation, the method predicts BP measurements of the individual based upon the CV signals and the calculated CV function measurements by creating a machine learning model from training data, and applies the CV signals and the calculated CV function measurements of the individual as input to the model to obtain the predicted BP measurements as output of the model. For this purpose, in one example, the training data might include anonymized versions of calculated CV function measurements and/or CV signals copied from medical records of multiple individuals, along with corresponding reference BP measurements of the multiple individuals obtained from one or more reference BP monitoring systems. In another example, the training data might include CV function measurements and corresponding BP measurements calculated from waveforms generated from one or more blood pressure models.

In general, according to yet another aspect, the invention features a cardiovascular analysis system. The system includes in-ear biosensor systems worn by individuals, an application server and a data analysis system. The in-ear biosensor systems each include left and right earbuds placed at or within ear canals of the individuals, and the earbuds each include at least one infrasound/vibration sensor that detects biosignals including cardiovascular activity signals (CV signals) from the individuals. The application server validates each of the individuals as authorized users of the system. The data analysis system receives the biosignals including the CV signals from the biosensor systems, calculates CV function measurements of the users based upon the CV signals, and predicts BP measurements of the users based upon the CV signals and the calculated CV function measurements.

In general, according to still another aspect, the invention features a cardiovascular analysis system using machine learning. The system includes an in-ear biosensor system worn by an individual and a data analysis system. The in-ear biosensor system includes at least one earbud at or within an ear canal of the individual, and the at least one earbud includes at least one infrasound/vibration sensor that detects biosignals including cardiovascular signals (CV signals) from the individual. The data analysis system receives the detected biosignals including the CV signals from the biosensor system and calculates cardiovascular function measurements (CV function measurements) of the individual based upon the CV signals; creates a machine learning model from training data; and applies the CV signals and the calculated CV measurements as input to the machine learning model to obtain predicted BP measurements of the individual as output of the model.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings:

FIG. 4A is a block diagram showing major fields of a medical record of an individual stored in a medical record database of the CV monitoring system, and FIG. 4B is a block diagram showing major fields of a user account of an individual stored in a user account database of the CV monitoring system;

FIG. 5A is a block diagram showing more detail for time-stamped user CV data and baseline CV data fields within the medical record of FIG. 4A, where these fields include CV function measurements calculated at and populated by the data analysis system in the CV monitoring system of FIG. 1A;

FIG. 5B is a block diagram showing more detail for time-stamped user CV data and baseline CV data as in FIG. 5B, where the fields within the medical record additionally include CV function measurements calculated at and populated by the data analysis system in the CV monitoring system of FIG. 1B;

FIG. 8 is a flow diagram that provides more detail for the method of FIG. 7, where the diagram shows how the data analysis system calculates various CV function measurements based on the CV signals, according to one implementation;

FIG. 10 is a flow diagram that provides more detail for the method of FIG. 7, where the diagram describes how the data analysis system uses machine learning to predict BP measurements from the CV signals and the calculated CV function measurements, according to one implementation;

FIG. 14A is a flow diagram that provides more detail for the method of FIG. 13, where the diagram shows how the data analysis system calculates additional CV function measurements from EKG signals sent from any of the EKG detection systems in FIG. 1B;

FIG. 14B is a flow diagram that provides more detail for the method of FIG. 13, where the diagram describes how the data analysis system uses machine learning to predict BP measurements from the CV signals, the CV function measurements calculated from the CV signals, and the additional CV function measurements calculated from the EKG signals, according to one implementation;

FIG. 16A is a flow diagram that describes another implementation for how the data analysis system can use machine learning to predict the BP measurements; and FIG. 16B is a flow diagram that describes yet another implementation for how the data analysis system can use machine learning to predict the BP measurements.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION OF THE PREFERRED EMBODIMENTS

The invention now will be described more fully hereinafter with reference to the accompanying drawings, in which illustrative embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

As used herein, the term "and/or" includes any and all combinations of one or more of the associated listed items. Further, the singular forms and the articles "a", "an" and "the" are intended to include the plural forms as well, unless expressly stated otherwise. It will be further understood that the terms: includes, comprises, including and/or comprising, when used in this specification, specify the presence of stated features, integers, steps, operations, elements, and/or components, but do not preclude the presence or addition of one or more other features, integers, steps, operations, elements, components, and/or groups thereof. Further, it will be understood that when an element, including component or subsystem, is referred to and/or shown as being connected or coupled to another element, it can be directly connected or coupled to the other element or intervening elements may be present.

It will be understood that although terms such as "first" and "second" are used herein to describe various elements, these elements should not be limited by these terms. These terms are only used to distinguish one element from another element. Thus, an element discussed below could be termed a second element, and similarly, a second element may be termed a first element without departing from the teachings of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Figure 1A:
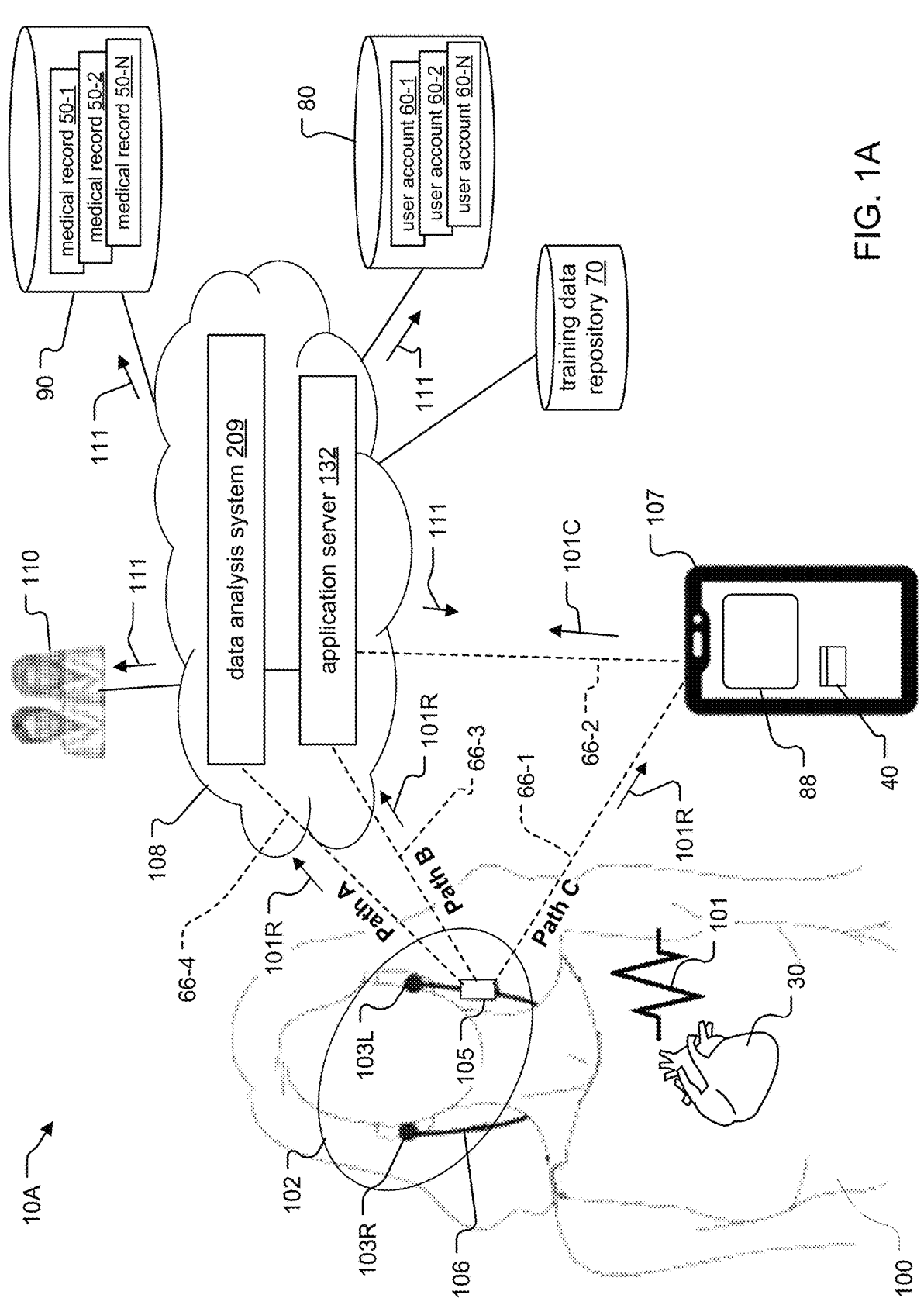
FIG. 1A is a schematic diagram of an exemplary cardiovascular monitoring and analysis system (CV monitoring system), according to an embodiment.

FIG. 1A shows an exemplary CV monitoring system 10A, according to an embodiment. The CV monitoring system 10A includes a biosensor system 102 worn by an individual 100 and a data analysis system 209. The biosensor system 102 includes infrasound/vibration sensors that detect biosignals including cardiovascular signals (CV signals) from the individual. The data analysis system 209 receives the biosignals including the CV signals from the biosensor system 102 and calculates cardiovascular function measurements (CV function measurements) of each individual based upon the CV signals, and predicts blood pressure measurements (BP measurements) of the individual based upon the CV signals and the calculated CV function measurements.

The system 10A also includes a user device 107 carried by the individual 100, an application server 132 located in a network cloud 108, and various databases that connect to the network cloud 108. The databases include a medical record database 90, a user database 80 and a training data repository 70.

The user devices 107 include portable user devices and stationary user devices. In examples, the portable user devices include mobile phones, smart glasses, smart watches, and laptops, in examples. The stationary user devices include workstations and gaming systems, in examples. A mobile phone/smartphone user device 107 is shown.

Each user device 107 is a computing device that includes a display 88 and one or more applications. An interactive application running on each user device 107, a user application (user app) 40, is shown. The user app 40 of each user device 107 executes upon a central processing unit (CPU) of the user device 107, receives information sent by other components in the system 10A and presents a graphical user interface (GUI) on the display 88. The GUI allows the individual 100 to enter information for the user app 40 and can display various information upon the display 88.

Medical professionals 110 are also shown. The medical professionals 110 include doctors, nurses/nurse practitioners, physician's assistants, and medical technicians, in examples. The medical professionals are trained in the use of medical diagnostics systems and reference BP monitoring systems.

The application server 132 is a computing device that connects the biosensor system 102 and the user device 107 to the databases 70,80,90, the medical professionals 110 and the data analysis system 209. The application server 132 includes secure website software (or a secure proprietary application) that executes on the application server 132.

More detail for the databases is as follows. The medical record database 90 includes medical records 50 of individuals 100 and the user database 80 includes user accounts 60 of the individuals. The user accounts 60 are associated with individuals 100 that the system 10A determines are authorized users of the system 10A. The training data repository 70 includes training data that the data analysis system 209 uses to predict BP measurements. In examples, the training data can include any combination of the following: anonymized content from the medical records 50 of multiple individuals; clinical trial data; anonymized CV function measurements of multiple individuals 100 obtained by one or more medical diagnostics systems; and anonymized BP measurements of multiple individuals 100 obtained by one or more reference BP monitoring systems.

The medical professionals 110, the user database 80, the user devices 107 and the medical record database 90 can connect to the network cloud 108 and components within the cloud 108 in various ways. These connections can be wired Internet-based or telephony connections, wireless cellular connections, and/or wireless Internet-based connections (e.g. Wi-Fi), in examples. In examples, the network cloud 108 is a public network, such as the Internet, or a private network.

The in-ear biosensor system 102 and the user devices 107 communicate with each other and with the network cloud 108 via wireless communications links 66. In more detail, the user device 107 connects to the in-ear biosensor system 102 via wireless link 66-1, and connects to the application server 132 via wireless link 66-2. The in-ear biosensor system 102 communicates with the application server 132 via wireless link 66-3 and might connect directly to the data analysis system 209 via wireless link 66-4. In this example, the capabilities provided by the application server 132 might be incorporated into the data analysis system 209. The wireless links 66 might be cellular-based or Internet-based (e.g. IEEE 802.11/Wi-Fi, or possibly even Bluetooth). In one example, the wireless links 66-3 and 66-4 are high-speed, 5G cellular links. These links 66 are also encrypted to provide secure communications between the components/to secure data sent between the components.

In the illustrated example, the data analysis system 109 and the application server 132 are located in the cloud network 108. The cloud network 108 is remote to the individual 100. In one implementation, the data analysis system 209 is a cloud-based service that is in communication with biosensor systems 102 worn by different individuals 100. As a result, the data analysis system can provide monitoring, analysis and reporting operations for multiple individuals 100. Alternatively, the data analysis system 209 and/or the server 132 might also be located on a local area network within a premises, such as a residence, commercial building or place of business of the individual 100.

In one implementation, as shown in the figure, the biosensor system is an in-ear biosensor system 102 that includes left and right earbuds 103L, 103R and a controller board 105. The earbuds 103 communicate with one another and with the controller board 105 via earbud connection 106. Here, the earbud connection 106 is a wired connection, but a wireless connection is also supported.

Infrasounds

Biosignals such as acoustic signals are generated internally in the body by breathing, heartbeat, coughing, muscle movement, swallowing, chewing, body motion, sneezing and blood flow, in examples. The acoustic signals can be also generated by external sources, such as air conditioning systems, vehicle interiors, various industrial processes, etc. The acoustic signals include audible and infrasonic signals.

The acoustic signals represent fluctuating pressure changes superimposed on the normal ambient pressure of the individual's body and can be defined by their spectral frequency components. Sounds with frequencies ranging from 20 Hz to 20 kHz represent those typically heard by humans and are designated as falling within the audible range. Sounds with frequencies below the audible range (i.e. from 0 Hz to 20 Hz) are termed infrasonic or infrasounds. The level of a sound is normally defined in terms of the magnitude of the pressure changes it represents. These changes can be measured and do not depend on the frequency of the sound.

The left and right earbuds 103L, 103R detect the biosignals from the individual 100 via sensors included within one or more of the earbuds 103. These sensors include acoustic sensors that include infrasound and vibration sensors and pressure sensors, in examples. The biologically-originating sound detected inside the ear canal by the earbuds 103 is mostly in the infrasound range. In particular, the infrasound and vibration sensors can detect biosignals from the individual 100 that are associated with operation of the cardiovascular system of the individual 100, also known as CV signals 101. The in-ear biosensor system 102 then sends the biosignals including the CV signals to the data analysis system 209 for analysis.

Typically, the biosignals are detected at each of the earbuds 103L,R at substantially the same times. This "stereo effect" can be utilized to improve a signal to noise ratio of the biosignals and thus more robustly identify/characterize the biosignals.

Each individual 100 might also register or "pair" personal information that identifies each of the individuals 100 with a particular in-ear biosensor system 102. Each individual would typically perform this registration or pairing process upon purchasing an in-ear biosensor system 102 or receiving one from a medical professional 110. For this purpose, the individual 100 accesses the user app 40 on the user device. The user app 40, in turn, communicates with the secure website software/secure proprietary application executing on the application server 132. Via the app 40, the individual 100 enters identifying information such as user credentials and a unique identifier associated with the in-ear biosensor system 102. The application server 132, in turn, stores the paired information to a user account 60 for the individual 100 in the user account database 90.

The CV monitoring system 10A generally operates as follows. An individual 100 wearing the in-ear biosensor system 102 typically initiates a login procedure by accessing the user app 40 of the user device 107. The individual 100 enters his/her credentials in the user app 40, which in turn sends the credentials for authentication to the application server 132. The secure website software at the application server 132 compares the entered credentials to those stored within the user accounts 60 of authorized users of the system 10A. Upon finding a match, the application server 132 establishes an authenticated, secure login session over wireless connection 66-2 between the user app 40 and the application server 132 for the individual as an authorized user of the system 10A.

The application server 132 then sends a copy of the matching user account 60 for local storage at the user app 40. The locally stored or "cached" version of the user account 60 is typically purged when stale, such as when the individual 100 does not access the user app 40 for a period of days or weeks. In this case, the individual 100 must repeat the login procedure. Once the individual 100 is authenticated, the user app 40 establishes secure wireless connection 66-1 between the user device 107 and the controller board 105. The user app 40 then sends various commands over the wireless connection 66-1 to the controller board 105.

The user app 40 might also determine whether the in-ear biosensor system 102 is paired to the proper authorized user. For this purpose, the user app 40 might access an identifier such as a serial number of the in-ear biosensor system 102 that the individual 100 previously entered into the app 40. Alternatively, the user app 40 might query the in-ear biosensor system 102 via its controller board 105 for the information. The user app 40 then compares the identifier to the stored identifier for the biosensor system 102 within the cached user account 60 record.

The earbuds 103L,103R continuously detect and collect the biosignals from the individual 100 and send the biosignals to the controller board 105. Here, the biosignals are in "raw" format: they are uncompressed and may include some noise and/or motion artifacts. In another embodiment, the biosignals might also be compressed, filtered, and preanalyzed. The controller board 105 buffers the biosignals for subsequent secure transmission to the data analysis system 209.

The earbuds 103L,103R send the detected biosignals to the data analysis system 209 by way of different communications paths. These paths are labeled Path A, B, and C in the figure and respectively include zero, one or more intermediary components located between the controller board 105 and the data analysis system 209. The decision of whether to send the biosignals along the different paths depends on factors including the speed capabilities of the wireless transceivers in the components, and characteristics of the wireless links 66 that form the communications paths. These characteristics include level of encryption, speed and available bandwidth, in examples. A description of Paths C, B, and A follow hereinbelow.

Path C is typically the slowest communications path. This path includes wireless links 66-1 and 66-2, and includes the user device 107 and the application server 132 as intermediary components between the in-ear biosensor system 102 and the data analysis system 209. In more detail, the controller board 105 first sends raw versions of the detected biosignals including raw CV signals 101R over link 66-1 to the user device 107. While the entirety of the detected raw biosignals are sent, only the raw CV signals 101R of the biosignals are indicated in the figure. The user app 40 then compresses the raw biosignals/CV signals 101R into compressed versions of the CV signals 101C for transmission over link 66-2 to the application server 132. The application server 132 then decompresses the compressed versions of the biosignals/CV signals 101C and forwards the raw versions to the data analysis system 209.

Path B is faster than Path C. Path B includes wireless link 66-3 and only one intermediary component, the application server 132, between the controller board 105 and the data analysis system 209. Because link 66-3 is a fast or high throughput link (such as a 5G cellular link), the controller board 105 can send the raw biosignals/CV signals 101R over link 66-3 to the application server 132 without having to compress the signals prior to transmission. Here, the application server 132 can perform various operations on the raw biosignals/CV signals 101R before forwarding the signals to the data analysis system 209 for analysis. These operations include filtering and characterization, authentication, and/or buffering of the signals.

Path A is as fast as or faster than Path B. Path A is a direct link to the data analysis system 209. Because link 66-4 is a fast or high throughput link similar to link 66-3, the controller board 105 can send the raw biosignals/CV signals 101R directly over link 66-4 to the data analysis system 209. In one example, such a communications path may be useful in a premises such as a large apartment building, clinical setting, college or work campus that includes the data analysis system 209 on a secure local area network that is maintained by a staff of information technology professionals. In this example, the data analysis system 209 can locally authenticate and service biosensor systems of possibly hundreds or thousands of individuals that live or work within range of the secure local area network. The locally managed, secure nature of the network can eliminate the need for the application server 132 to authenticate the frames of data including the biosignals/CV signals before sending the signals to the analysis system 209. Alternatively, the capabilities of the application server 132 can be integrated into the data analysis system 209 in this example.

The data analysis system 209 then analyzes the biosignals/CV signals 101, calculates cardiovascular function measurements of the individuals 100 based upon the CV signals, and predicts BP measurements of the individuals 100 based upon the cardiovascular function measurements and the CV signals 101. The data analysis system 209 or the application server 132 can access and update the medical record 50 of the individual 100 during and in response to the analysis.

The data analysis system 209 can also send various notification messages in response to analysis of the CV signals 101. For this purpose, the data analysis system 209 sends notification messages 111 that include information concerning the analysis and the results of the analysis to the medical professionals 110 and to the databases 80/90. The notification messages 111 can be in the form of an email, SMS/text message, phone call, database record in proprietary format or XML or CSV format, or possibly even audible speech, in examples.

The data analysis system 209 can also notify the individual 100 both during and after the analysis via the notification messages 111. Here, the user app 40 receives the notification messages 111 and might present the notification messages 111 at the display 88, or forward the messages 111 over the wireless link 66-1 to the in-ear biosensor system 102. In this way, the earbuds 103L, 103R could relay audible information to the individual 100 concerning operation of the system 10A, in one example.

As a result, the CV monitoring system 10A can continuously analyze biosignals/CV signals 101 detected by and sent from biosensor systems 102 worn by different individuals 100, calculate cardiovascular function measurements and BP measurements of the individuals 100 from the detected biosignals/CV signals 101, update medical records 50 for each of the individuals 100 with the calculated measurements, report problems/notify medical professionals 110, and provide feedback to the individuals 100 during and upon completion of the analysis.

Figure 1B:
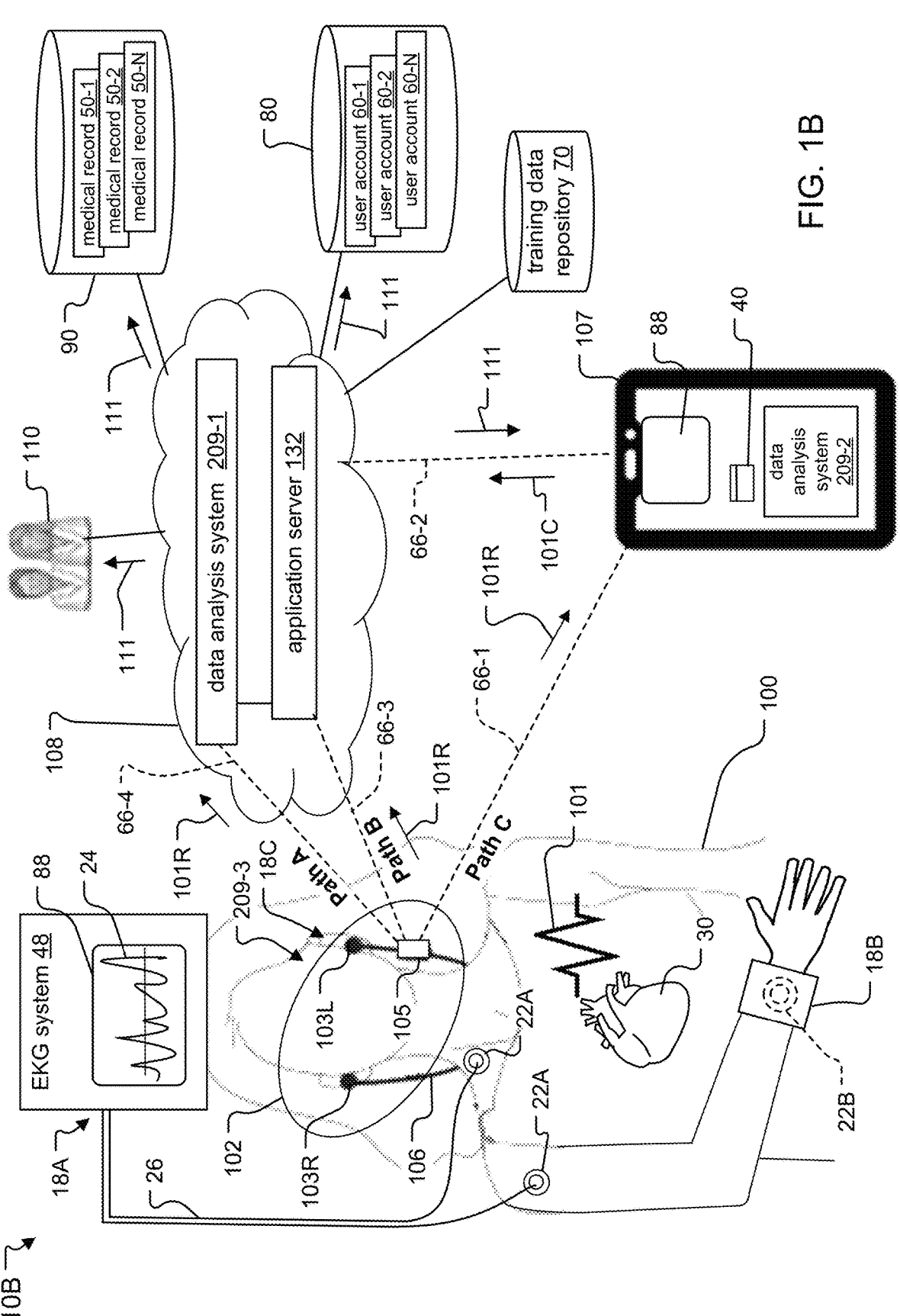
FIG. 1B is a schematic diagram of another exemplary CV monitoring system, according to another embodiment, where the system additionally includes one or more EKG detection systems that detect EKG signals of individuals.

FIG. 1B shows another exemplary CV monitoring system 10B, according to another embodiment. The system 10B includes similar components and operates in a substantially similar fashion as system 10A in FIG. 1A to calculate the cardiovascular function measurements of individuals and to predict the BP measurements of the individuals 100. However, there are differences.

The CV monitoring system 10B includes one or more EKG detection systems 18, three examples of which are shown. An EKG detection system is a component of an overall EKG system and includes electrodes 22 and wires/leads 26 attached to the electrodes 22. The electrodes 22 detect changes in electrical signals associated with cardiovascular activity of an individual 100 over a series of successive heart cycles. Via its wires 26, the detection system 18 sends the detected EKG electrical signals (EKG signals 24) to an analysis system such as the one or more data analysis systems 209 for analysis. The illustrated EKG detection systems 18 include EKG detection system 18A of a standard EKG system 48, a wrist-worn EKG detection system 18B, and a wearable EKG detection system 18C integrated within in-ear biosensor system 102 are shown.

Three different data analysis systems 209 are shown. Remote data analysis system 209-1 is located in the network cloud 108 and operates in a similar fashion as the data analysis system 209 in FIG. 1A. Data analysis system 209-2 is located with the user device 107. Here, the analysis system 209-2 is either a software or firmware application, or a collection of multiple software applications and hardware components of the user device 107. Data analysis system 209-3, in contrast, is a component of the in-ear biosensor system 102. In examples, the analysis system 209-3 is integrated within one or more of the earbuds 103LR; included within the controller board 105; or distributed across the controller board 105 and one or more of the earbuds 103L,R.

The CV monitoring system 10B can additionally process the EKG signals 24 detected by and sent from one or more of the EKG detection systems 18. In more detail, the various data analysis systems 209-1 through 209-3 can calculate additional CV function measurements based upon the EKG signals 24 and in conjunction with the CV function measurements obtained from the CV signals 101. These additional CV function measurements include a pre-ejection period (PEP) and onset time (PEP onset), a systolic timing duration and a diastolic timing duration. Typically, these additional CV function measurements are derived from the Q, R and S complexes within the EKG signals 24 in combination with other CV function measurements obtained from the CV signals 101.

For example, current EKG systems individually cannot measure the PEP 206 or the systolic timing duration 302 directly, using the CV function measurements that these systems obtain from their EKG signals 24. Typically, the echo system must also be used in conjunction with an EKG system to obtain the PEP 206 and the systolic timing duration 302. However, the CV monitoring system 10B in FIG. 1B can individually calculate the PEP 206 and the systolic timing duration 302 without the use of additional medical diagnostics systems.

In more detail, in one example, the EKG detection systems 18 can detect only the starting point of the systolic time duration 304. The echo system is thus required to provide the ending point of the systolic time duration 304. The ending point of the systolic time duration 304 is also the value of the AVC 203, which the echo system can calculate. However, the CV monitoring system 10A/B also accurately calculates the AVC 203 from the CV signals 101. Thus, the CV monitoring system 10B can calculate the systolic time duration 304 as an indirect CV function measurement, by subtracting the value of the AVC 203 from the value of the R peak obtained via the EKG signal 24.

In another example, the PEP 206 is the difference between the onset of left ventricular depolarization and the AVO time 202. While the onset of left ventricular depolarization is accurately indicated by the onset of the QRS complex in an EKG signal 24, the echo system is currently required to additionally obtain the AVO time 202. However, the CV monitoring system 10A/B also accurately calculates the AVO time 202 from the CV signals 101. Thus, the CV monitoring system 10B can calculate the PEP 206 as an indirect CV function measurement, by subtracting the value of the onset of left ventricular depolarization obtained via the EKG signal 24 from the value of the AVO time 202.

EKG detection system 18A is a component of a standard EKG system 48. The EKG system 48 includes an analysis system that analyzes the detected EKG signals from the electrodes 22/wires 26 and a display 88. The analysis system produces an EKG 24 from the signals, and displays the EKG 24 on the display 88.

EKG detection system 18B is a wrist-worn device that is a component of a wrist-worn EKG system. The wrist-worn EKG system is not as accurate as the EKG system 48. The detection system 18B has an electrode 22B placed against the skin of the individual 100. The electrode 22B is also located under the wristband of the wrist-worn device. The device can analyze the EKG signals 24 locally and also send its EKG signals via a wireless link to other devices or systems for analysis, such as to one or more of the data analysis systems 209-1 through 209-3. The data analysis systems 209 can then display the EKG signals 24 on a display, such as the display 88 of the user device 107. In this way, an EKG system can be formed from a combination of the EKG detection system 18B, one or more the data analysis systems 209-1 through 209-3 and a display such as display 88 of the user device 107, in one example.

EKG detection system 18C is integrated within the in-ear biosensor system 102. As with the integrated data analysis system 209-3, the integrated EKG detection system 18C can be included within: one or more of the earbuds 103L,R; the controller board 105; or distributed across these components. An EKG system can be formed from a combination of the EKG detection system 18C, one or more the data analysis systems 209-1 through 209-3 and a display such as display 88 of the user device 107.

The EKG detection systems 18 can wirelessly send their EKG signals 24 for processing to the various data analysis systems 209-1 through 209-3 using various communications paths. For example, the EKG detection systems 18 can use the same Paths A, B and C that the biosensor system 102 sends its CV signals 101 over for analysis by the remote data analysis system 209-1 or the data analysis system 209-2 at the user device 107. In another example, the integrated EKG detection system 18C sends its EKG signals 24 to the integrated data analysis system 209-3.

It can also be appreciated that the data analysis system 209 can be configured and implemented in additional ways.

In one example, the data analysis system 209 is an external hardware/firmware "addon module" that interfaces via a peripheral device port of the user device 107 such as its Universal Serial Bus (USB) interface. In yet other examples, the data analysis system 209 might be distributed across one or more user devices 107, or across the user device 107 and the application server 132.

A computing device includes at least one or more central processing units (CPUs) and a memory. The CPUs have internal logic circuits that perform arithmetical operations and execute machine code instructions of applications ("application code") loaded into the memory. The instructions control and communicate with input and output devices (I/O) such as displays, printers and network interfaces.

The CPUs of the computing devices are typically configured as either microprocessors or microcontrollers. A microprocessor generally includes only the CPU in a physical fabricated package, or "chip." Computer designers must connect the CPUs to external memory and I/O to make the microprocessors operational. Microcontrollers, in contrast, integrate the memory and the I/O within the same chip that houses the CPU.

Computing devices that use microprocessors and microcontrollers are typically suited for different applications. Designers of microprocessor-based computing devices can choose from many different types and sizes of the external memory and I/O during system design. The microprocessors also typically have significant computing power, enabled by having multiple "cores" (i.e. multiple CPUs) within the microprocessors. The flexibility of configuration and computing power of microprocessors allows microprocessor-based computing devices to have many different configurations for use in a wide array of applications. In contrast, the integrated nature of the microcontrollers makes them especially suited for special-purpose computing devices such as embedded systems. In embedded systems, factors such as cost, physical size, and power and cooling are typically more important than computing power and flexibility.

The CPUs of the microcontrollers and microprocessors execute application code that extends the capabilities of the computing devices. In the microcontrollers, the application code is typically pre-loaded into the memory before startup and cannot be changed or replaced during run-time. In contrast, the CPUs of the microprocessors are typically configured to work with an operating system that enables different applications to execute at different times during run-time.

The operating system has different functions. The operating system enables application code of different applications to be loaded and executed at run-time. Specifically, the operating system can load the application code of different applications within the memory for execution by the CPU, and schedule the execution of the application code by the CPU. In addition, the operating system provides a set of programming interfaces of the CPU to the applications, known as application programming interfaces (APIs). The APIs allow the applications to access features of the CPU while also protecting the CPU. For this reason, the operating system 172 is said to execute "on top of" the CPU.

Other examples of CPUs include Digital Signal Processors (DSPs), Application Specific Integrated Circuits (ASICs), and Field Programmable Gate Arrays (FPGAs). The DSPs are pre-programmed, special-purpose microprocessors optimized for the requirements of digital signal processing. The ASICs are CPUs that are pre-programmed and optimized for particular purposes such as image processing, video encoding and decoding, and cellular communications. The DSPs, the ASICs, and the FPGAs have internal logic/application code in the form of an executable image file. The image file of the DSPs and the ASICs have fixed image files, while the FPGAs allow the end user to iteratively replace the image file to customize, test, and reprogram its internal logic/application code. As compared to FPGAs, which seek a tradeoff between performance and the ability of the end user to reprogram, DSPs and ASICs typically have a small footprint, lower power consumption, can operate at higher frequencies, and provide higher performance than FPGAs.

The DSPs convert various types of input into digital signals, and perform operations upon the digital signals such as filtering, compression, conversion and transformation. The DSPs usually support analog to digital (A/D) and digital to analog (D/A) conversion and transformations including Fourier, Z, and wavelet transforms, in examples.

While only one individual 100 is shown in the CV monitoring systems 10A and 10B of FIGS. 1A and 1B, these systems 10 can include and service multiple individuals 100 that are registered users of these systems 10. When the data analysis system 209 is located in a network cloud 108 such as the Internet, for example, the registered users could be located anywhere in the world and be able to access the CV monitoring systems 10.

In this way, the CV monitoring system 10 can also form a cardiovascular analysis system. The cardiovascular analysis system includes in-ear biosensor systems 102 worn by individuals 100 that each include left and right earbuds 103L,R placed at or within ear canals of the individuals 100, where the earbuds 103 each include at least one infrasound/vibration sensor that detects biosignals including cardiovascular activity signals (CV signals) 101 from the individuals 100. The cardiovascular analysis system also includes an application server 132 and a data analysis system 209. The application server 132 validates each of the individuals 100 as authorized users of the cardiovascular analysis system. The data analysis system 209 receives the biosignals including the CV signals 101 from the biosensor systems worn by the authorized users, calculates CV function measurements 954 of the users based upon the CV signals 101, and predicts BP measurements of the users based upon the CV signals 101 and the calculated CV function measurements 954.

Figure 2A:
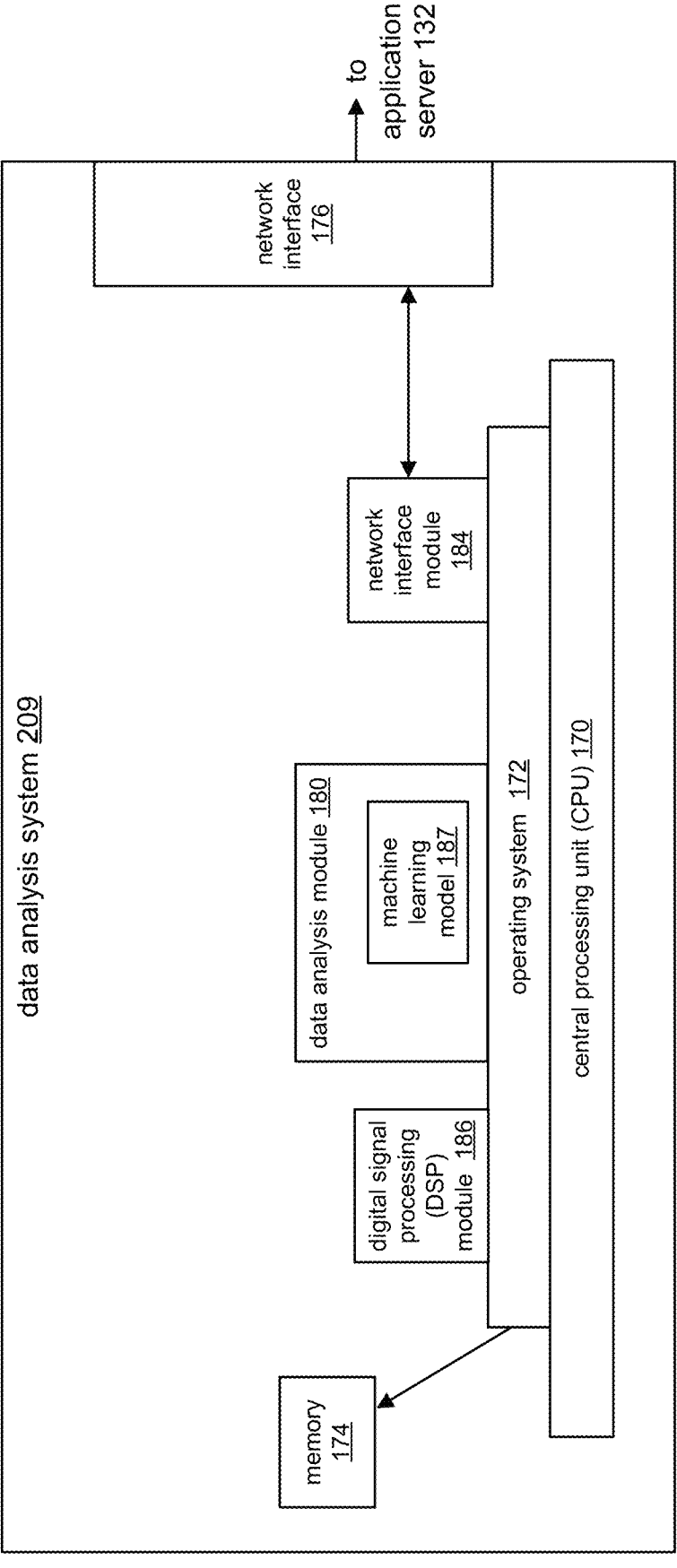
FIG. 2A is a schematic diagram that shows detail for an exemplary data analysis system in the CV monitoring systems of FIGS. 1A and 1B.

FIG. 2A shows detail for an exemplary data analysis system 209. The data analysis system 209 is configured as a microprocessor and includes a central processing unit (CPU) 170, an operating system 172, a non-volatile memory 174, a network interface 176, and various software applications. The software applications include a data analysis module 180, a digital signal processing (DSP) module 186 and a network interface module 184.

The data analysis module 180 includes a machine learning model 187. The analysis module 180 creates (i.e. trains) the machine learning model 187 using various training data from the training data repository 70. Here, the machine learning model 187 is located within temporary/volatile memory of the data analysis module 180 but can also be saved to the non-volatile memory 174.

The network interface module 184 communicates with the network interface 176. The network interface 176, in turn, connects to the application server 132.

Figure 2B:
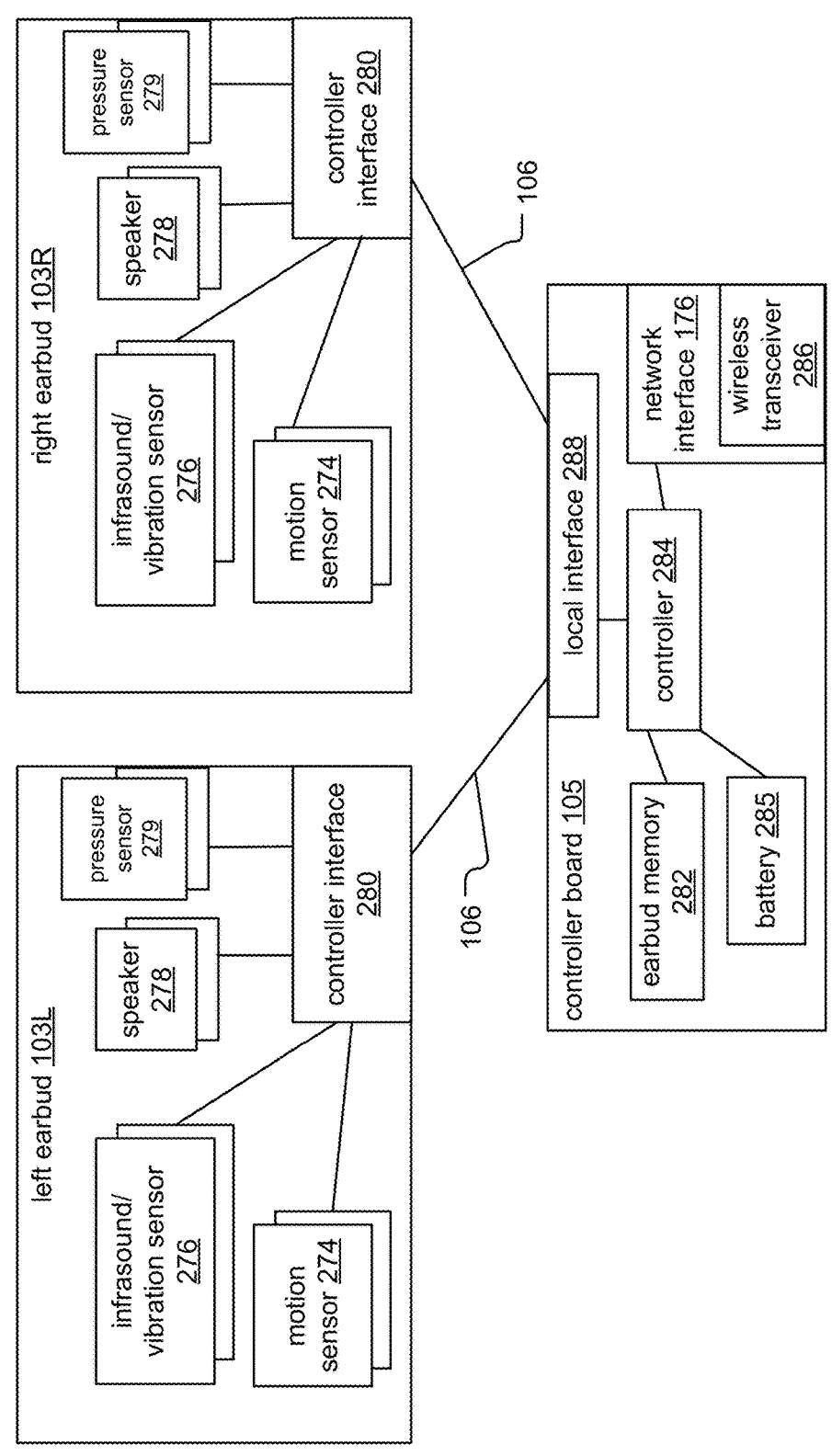
FIG. 2B is a schematic diagram showing detail for an implementation of the in-ear biosensor system in FIGS. 1A and 1B.

FIG. 2B shows detail for one implementation of the in-ear biosensor system 102 in the CV monitoring systems 10A and 10B.

The left and right earbuds 103L,103R include substantially the same components and operate in substantially the same way. The earbuds 103 each include one or more motion sensors 274, acoustic sensors such as infrasound/vibration sensors 276, speakers 278, pressure sensors 279, and a controller interface 280. The motion sensors include accelerometers and gyroscopes, in examples. The infrasonic/vibration sensors 276 operate in the infrasonic range, and might also operate in the audible range as well. The pressure sensors 279 can be used to characterize a level of seal/occlusion and monitor changes in baseline pressure in the ear canal due to, for example, physiological changes. These pressure sensors 279 are examples of auxiliary sensors that can detect pressure biosignals in the individual's ear to monitor occlusion level of one or both of the earbuds 103L,R and to monitor physiological changes of the individual 100.

The controller board 105 includes a local interface 288, earbud memory 282, a battery 285, a controller 284, and a network interface 176. The network interface 176 includes a wireless transceiver 286. The controller board 105 provides power to and enables communications between the earbuds 103L, 103R via the local interface 288 and the earbud connection 106.

Within the earbuds 103, the controller interface 280 connects to the sensors 274, 276, 279 and the speakers 278. The controller interface 280 also connects to the controller board 105 via the earbud connection 106. In one implementation, the controller interface 280 is a wired bus.

Within the controller board 105, the controller 284 connects to local interface 288, the earbud memory 282, the battery 285, and the network interface 176. The controller 284 can be configured as a microcontroller or microprocessor. In one example, the controller 284 is a reprogrammable FPGA. The controller 284 controls the operation of the other components in the controller board 105.

The sensors 274, 276, 279 within each of the earbuds 103L, 103R detect various information including sounds and vibrations originating from the individual 100 and send biosignals representing the information to the controller board 105. These signals and vibrations are typically associated with operation of the heart 30 and its various chambers and valves. Additionally, the infrasound/vibration sensors 276 can also detect sounds and vibrations associated with other cardiovascular components such as the lungs, arteries, veins, coronary and portal vessels. The motion sensors 274 detect movement of the individual (e.g. moving, sneezing), and represent the motion as motion artifacts within the biosignals.

The controller board 105 receives the biosignals detected by and sent from the earbuds 103 and transmits the biosignals to other components in the system 10 via the network interface 176. The controller 284 receives the biosignals from the earbuds 103 via the local interface 288, and buffers the signals in the earbud memory 282 or in local memory of the network interface 176. The network interface 176 then sends the biosignals via the wireless transceiver 286 to other components of the CV monitoring system 10. In one example, the controller board 105 transmits the biosignals to other components in the CV monitoring system 10, in response to receiving commands sent from the user app 40 executing on user device 107 worn by the individual 100.

The controller board 105 also receives information from other components in the system 10 via the network interface 176. This information includes the notification messages 111 for presentation at the earbuds 103L, 103R, and commands sent from the user app 40. In another example, the information includes updates for application code running within the controller 284. In yet another example, the information includes replacement image files for updating the internal logic of the controller 284 (when the controller is an FPGA). In still another example, the information includes requests to establish wireless communications links between the earbuds 103 and other components in the CV monitoring system 10.

Figure 2C:
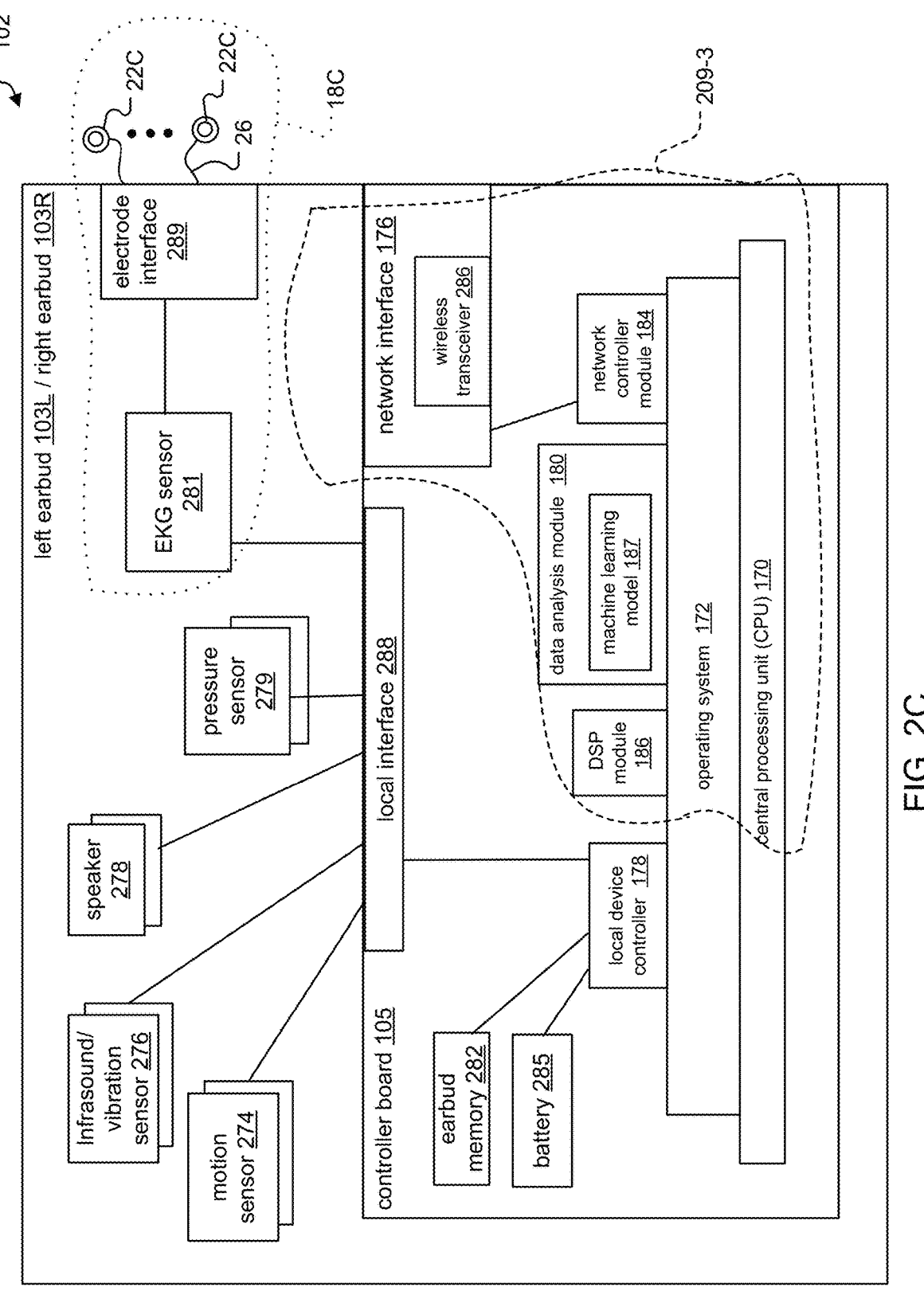
FIG. 2C is a schematic diagram showing detail for another implementation of the in-ear biosensor system in FIG. 1B.

FIG. 2C shows detail for an implementation of the in-ear biosensor system 102 in the CV monitoring system 10B of FIG. 1B. In the illustrated example, one or both of the earbuds 103L,R can be configured as shown. The in-ear biosensor system 102 includes similar sensors as in FIG. 2A and additionally includes an EKG sensor/transducer 281 and an electrode interface 289. The controller board 105 includes some of the same components as the controller board in FIG. 2A and also includes an integrated data analysis system 209-3. The in-ear biosensor system 102 also includes an integrated ECG detection system 18C.

The controller board 105 includes a local interface 288, non-volatile earbud memory 282, a battery 285, and a network interface 176. The controller board 105 is configured as a microprocessor. For this purpose, the controller board additionally includes central processing unit (CPU) 170, operating system 172 and various software applications. The software applications include a data analysis module 180, a digital signal processing (DSP) module 186, a network controller module 184 and a local device controller 178.

The network interface 176 includes wireless transceiver 286 and the data analysis module 180 includes machine learning model 187. Local device controller 178 connects to the local interface 288 and controls the earbud memory 288 and the battery 285. The network controller module 184 connects to and controls the network interface 176. The EKG sensor 281 connects to the local interface 288 and to the electrode interface 289.

Multiple electrodes 22C are connected to wires 26, which in turn connect to the electrode interface 289. The electrodes 22C are either urged against or are attached to various locations on the skin of the individual 100. In one example, the electrodes 22C can be formed within a material of the earbuds 103 (e.g. compressible foam) and the wires 26 are within the material/hidden from view. In this way, the electrodes 22C are urged against skin of the inner ear canal when the earbuds 103 are snugly placed/fit within the inner ear canal. In another example, as shown in the figure, the wires 26 project outward from the earbuds 103. The electrodes 22C connected to the wires 26 are then attached to different locations on the skin of the individual. These locations might include skin of the outer ear, and other locations near the ear such as the temples (temporal arteries) and the sides of the neck (carotid arteries).

The in-ear biosensor system 102 illustrated in the figure generally operates as follows. The sensors 276, 279 and 281 detect biosignals from the individual 100 and send the biosignals over the local interface 288. The motion sensor 274 sends the detected motion signals to the local interface 288. The local device controller 178 receives the biosignals including the CV signals 101 from the infrasound/vibration sensor 276, the pressure biosignals from the pressure sensor 279 and the EKG signals 24 from the EKG sensor 281, and receives the motion signals. The local device controller 178 then sends the biosignals and the motion signals via the operating system 172 and the CPU 170 for processing by the data analysis module 180.

In one implementation, only one of the earbuds 103 is configured as shown, and the other earbud 103 does not include the data analysis module 180, the DSP module 186, and the components that form the EKG detection system

18C. In this configuration, the earbud detects and sends its biosignals and motion signals wirelessly via its network interface 176 to the network interface 176 of the other earbud 103. At the other earbud, the network controller module 184 receives the biosignals and motion signals from the other earbud 103 and sends the signals via the operating system 172 and the CPU 170 for processing by the data analysis module 180.

It can also be appreciated that the EKG detection system 18C can be integrated within the "wired" version of the in-ear biosensor system 102 of FIG. 2A. Here, the components of the EKG detection system 18C would be included within the controller board 105 that is separate from the earbuds 103L,R. In this example, the electrode interface 289 could be a socket, and the wires 26 connected to the electrodes 22C would terminate in a plug that connects to the socket. In this way, the individual 100 would be able to more easily attach the electrodes 22C to locations on the skin throughout the individual's body.

Figure 3A:
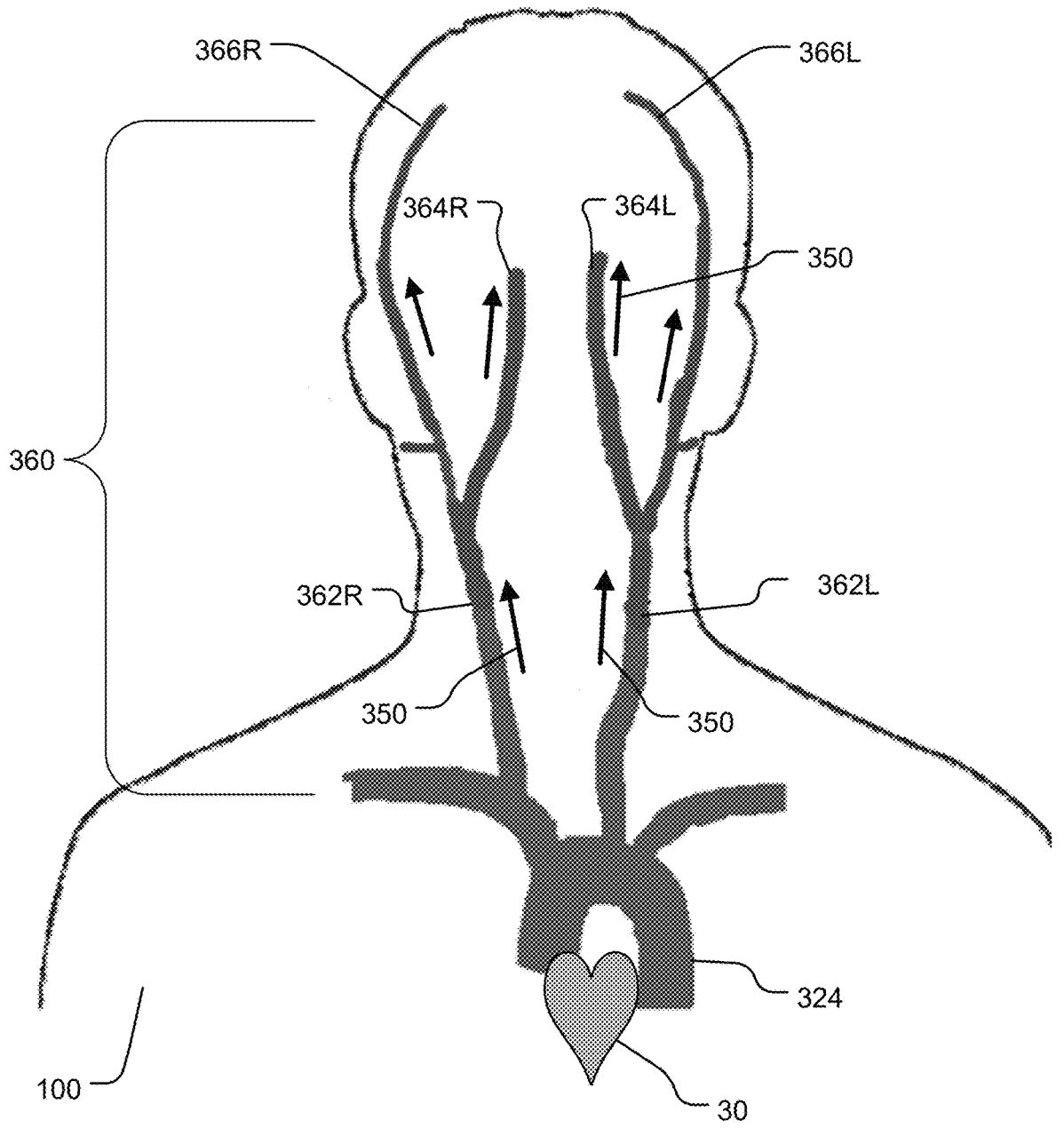
FIG. 3A is a schematic diagram that illustrates a portion of a cardiovascular system of an individual.
Figure 3B:
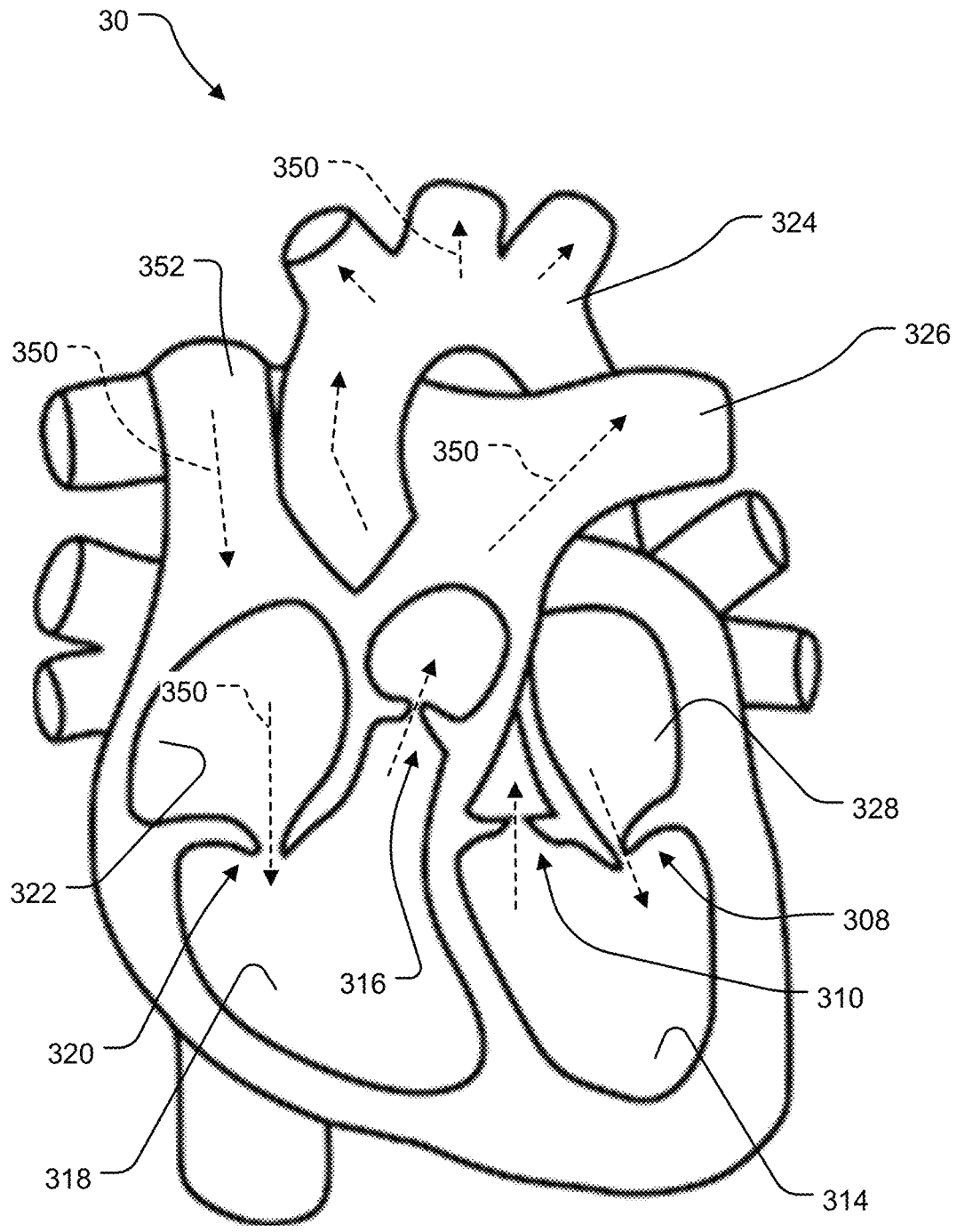
FIG. 3B is a front section view of an individual's heart.

FIG. 3A illustrates a portion of a vascular system 360 of an individual 100. The diagram identifies major arteries of an individual 100 from the heart 30 upwards towards the head, and illustrates blood flow 350 within the arteries.

Vascular system 300 is connected to heart 30, which ejects blood into a branching set of arteries during ventricular contraction. Following ventricular contraction, blood is ejected from the heart 30 through its aortic valve and into the aorta 324. The blood continues upward and divides into smaller arteries that branch off of the aorta 324. The two main branches are a left common carotid artery (LCCA) 362L and a right common carotid artery (RCCA) 362R.

Before the RCCA 362R branches, the RCCA 362R shares a base portion of the branch with a right subclavian artery before the two diverge soon off of the aorta 324. The RCCA 362R and the LCCA 332 extend up from the heart 30 into the neck for a distance that is approximately 12.4 cm. The RCCA 362R bifurcates again at this point into a right internal carotid artery (RICA) 364R and a right external carotid artery (RECA) 366R. In a similar fashion, the LCCA 362L bifurcates into a left internal carotid artery (LICA) 364L and a left external carotid artery (LECA) 366L.

Following these bifurcations, the blood continues to traverse through the arteries until reaching the corresponding terminal branches, from which blood is provided to tissues via capillaries. In the case of the LICA 364L and RICA 364R, these terminal arteries reside in the brain; such terminal arteries may not be sensed by the CV monitoring system 10. Corresponding branches of the LECA 366L and RECA 366R reside on a superficial surface of the left and right sides of the skull, respectively. As such, the termination of these arteries into their corresponding branches may be sensed by the CV monitoring system 10.

FIG. 4 is a cutaway view of an individual's heart 30. This shows various components of the heart 30 and illustrates blood flow 350 among the components.

The heart 30 has four chambers and four valves. The chambers include a right atrium 322, a right ventricle 318, a left atrium 328 and a left ventricle 314. The valves include a tricuspid valve 320, a pulmonary valve 316, an aortic valve 310 and a mitral valve 308.

Two main arteries pump blood to all parts of the body. These arteries are the aorta 324 and a pulmonary artery 326. The aorta 324 connects to and arises from the left ventricle 314 and pumps blood to all parts of the body except the lungs. The pulmonary artery 326, in contrast, connects to and arises from the right ventricle 318 and transports blood to the lungs.

All veins include valves to maintain the direction of blood flow 350 and to prevent backflow. While the pulmonary artery 326 and the aorta 324 technically also include valves, the pulmonary valve 316 and the aortic valve 310, respectively, each of these valves are located within the heart 30 at a point where these arteries attach to the heart 30. As a result, these valves 310, 316 are generally considered to be heart valves.

Connections among the components of the heart 30 are as follows. The mitral valve 312 connects the left atrium 328 and the left ventricle 314. The tricuspid valve 320 connects the right atrium 322 and the right ventricle 318. The pulmonary valve 316 connects the right ventricle 318 and the pulmonary artery 326. The aortic valve 310 connects the left ventricle 314 and the aorta 324. A superior vena cava 352 is also shown.

Basic operation of the heart is described below, with reference to the various components of the heart 30 in the figure. Some cardiovascular function measurements are also referenced in the description. The cardiac function measurements described below include an isovolumetric contraction period (IVC) 207, a left ventricle ejection time (LVET) 208, a pre ejection period (PEP) 206 and an isovolumetric relaxation period (IVR period) 211.

The cardiac cycle of the heart 30 basically operates as follows. The right atrium 322 receives de-oxygenated blood from the veins and pumps the blood via the tricuspid valve 320 to the right ventricle 318. The right ventricle 318 pumps the blood via the pulmonary valve 316 and pulmonary artery 326 to the lungs, which adds oxygen to the blood. The left atrium 328 receives the oxygenated blood from the lungs, and pumps the blood via the mitral valve 312 to the left ventricle 314. The left ventricle 314 (the strongest chamber) then pumps the oxygen-rich blood via the aortic valve 310 and the aorta 324 to the rest of the body of the individual 100. The vigorous contractions of the left ventricle 314 create the blood pressure of the individual 100.

The cardiac cycle is divided into two periods that repeat in succession: systole (or systolic timing duration), and diastole (or diastolic timing duration). The systolic timing duration generally refers to the time during which the left ventricle 314 is contracting. This period begins when the mitral valve 312 closes and ceases the flow of blood between the left atrium 328 and the left ventricle 314. This is also the onset of the IVC period 207, in which the left ventricle 314 is contracting but its volume is not yet changing. This IVC 207 is the only time during the systole in which all the valves of the heart are closed.

Once the left ventricle 314 contracts sufficiently, the pressure forces the aortic valve 310 open and the blood flows through the aortic valve 310 into the aorta 324. Once the blood enters the aorta 324, the blood perfuses to the periphery of the body of the individual 100. The period during which the aortic valve 310 is open is the LVET 208. This period ends when the aortic valve 310 closes.

When the LVET 208 ends, the pulmonary valve 316 also closes, which allows blood to leave the opposing right ventricle 318. The blood leaves the right ventricle 318 via the pulmonary artery 326 during the same time frame, meaning no more blood is leaving the heart and left ventricle 314 contraction has ceased. This marks the end of the systolic timing duration/systole.

Once the systolic period ends, the diastolic period or diastole begins. During the diastolic period, the ventricles 314, 318 relax and the atria 322, 328 fill with blood. The atria 322, 328 eventually contract just prior to the onset of another systolic period.

Just prior to the onset of the next systolic period, the PEP 206 begins. This period begins at the onset of electromechanical stimulation of the ventricles, often determined as the time of the Q wave in an EKG signal 24. This period contains the IVC 207 and terminates when the aortic valve 310 opens and the LVET 208 begins.

FIG. 4A shows major fields of a medical record 50 of an individual 100 stored in the medical record database 90. The fields include user data 902, biometric data 904, baseline cardiovascular data (baseline CV data) 930 and user cardiovascular data (user CV data) 950. Additional fields include normal ranges of CV function measurements 932, normal ranges of BP measurements 934, threshold percentage change values of the CV function measurements 936, and threshold percentage change values of the BP measurements 938.

The user data 902 includes information that identifies the individual 100. This information includes a name, address, and telephone number of the individual 100. The biometric data 904 includes information such as age, weight, and height of the individual 904.

FIG. 4B shows major fields of a user account 60 of an individual 100 stored in the user account database 80. The fields include credentials 960, an in-ear biosensor system version 962, a user app version 924, and system calibration data 966.

The credentials 960 include information that uniquely identifies the individual 100. This information can be entered by the individual 100 and stored to a user account 60 created by the system 10 as part of an initial registration process. The credentials might include a username/password combination, and/or a biometric ID such as fingerprint or iris scan, in examples.

FIG. 5A shows detail for the baseline CV data 930 and user CV data 950 fields within an individual's medical record 50. The baseline CV data 930 and user CV data 950 generally have the same structure and content.

The baseline CV data 930/user CV data 950 include time-stamped records or instances of detected information 952, CV function measurements 954 and aggregated BP measurements 956. The aggregated BP measurements 956 include both measured values and predicted values (BP measurements predicted by the CV monitoring system 10A). Each time-stamped instance is stored in an individual row 630-1 . . . 630N.

Each row 630 has the following contents: a time stamp 602; the detected information 952 that the in-ear biosensor system detects from the body of the individual 100; CV function measurements 954 of the individual 100 calculated by the data analysis system 209; and aggregated BP measurements 956 of the individual 100. Time stamps 602-1 . . . . 602-N, detected information 952-1 . . . 952-N, CV function measurements 954-1 . . . 954-N, and BP measurements 956-1 . . . 956-N for rows 630-1 . . . 630-N are shown.

The baseline CV data 930, as its name implies, is a reference or baseline that the CV monitoring system 10 or a medical professional 110 establishes for each individual 100. When an individual 100 first uses the system 10, the data analysis system 209 first creates a time-stamped instance of user CV data 950, and copies this instance to the baseline CV data 930. This establishes an initial baseline of the detected information 952, the calculated CV function measurements 954, and the BP measurements 956 to be used as a reference. Alternatively, a medical professional might populate the baseline CV data 930 via a private, secure interface of the application server 132.

The detected information 952 includes (raw) CV signals 101, a stacked CV signal 101S, and a user app version 964 of the user app 40 that was running when the CV monitoring system 10A created the instance of baseline CV data 930/ user CV data 950. The stacked CV signal 101S refers to CV signals 101 detected over a successive number of cardiac cycles and then averaged.

While the CV monitoring system can calculate the CV function measurements and predict the BP measurements over individual cardiac cycles (i.e. based upon individual CV signals 101 associated with each of the cardiac cycles), experimentation has shown that more accurate measurements can be obtained using the average or stacked CV signal 101S for a successive number CV signals 101 detected and obtained for a successive number of cardiac cycles.

The CV function measurements include various measurements that the CV monitoring system 10A calculates from the raw CV signals 101 and/or stacked CV signals 101S of the detected information 952. These measurements include a mitral valve closing and an opening time (MVC) 201, an aortic valve opening time (AVO) 202 and closing time (AVC) 203, a systolic peak 218 and a diastolic peak 220, an elasticity index 412, a left ventricle ejection time (LVET) 208, an isovolumetric closing time (IVC) 207 and relaxation period (IVR) 211, a stroke volume (SV) 210, an inflection point 222 and a ventricular contraction period (VC period) 301, and a vascular aging index 414.

The aggregated BP measurements 956 include measured values and predicted values for the BP measurements. The measured values include a measured systolic BP 370, a measured diastolic BP 372 and a measured mean arterial pressure 374. The predicted measurements include a predicted systolic BP 376, a predicted diastolic BP 378 and a predicted mean arterial pressure 380.

The mean arterial pressure can be calculated from systolic and diastolic BP measurements using the simple formula:

(Systolic BP+2(Diastolic BP))/3.

More accurate and complex formulae also exist. Typically, mean arterial pressure is measured most accurately via the invasive catheter BP system and is the reference for this measurement in clinical trials.

Over time, a medical professional 100 might manually populate the baseline CV data 930, or direct the individual 100 to establish a new baseline/instance of baseline CV data 930. This could occur in response to a change of the individual's medical condition, age, or other factors. For this purpose, the CV monitoring system 10 could append a new time-stamped instance of baseline CV data 930 to the medical record 60, or overwrite the existing instance of the baseline CV data 930 with a copy of the recently obtained user CV data 950. The former method is likely more useful, as the medical professional 110 could track changes to the baseline CV data 930 over time as an indication of health changes/trends.

Figure 5B:
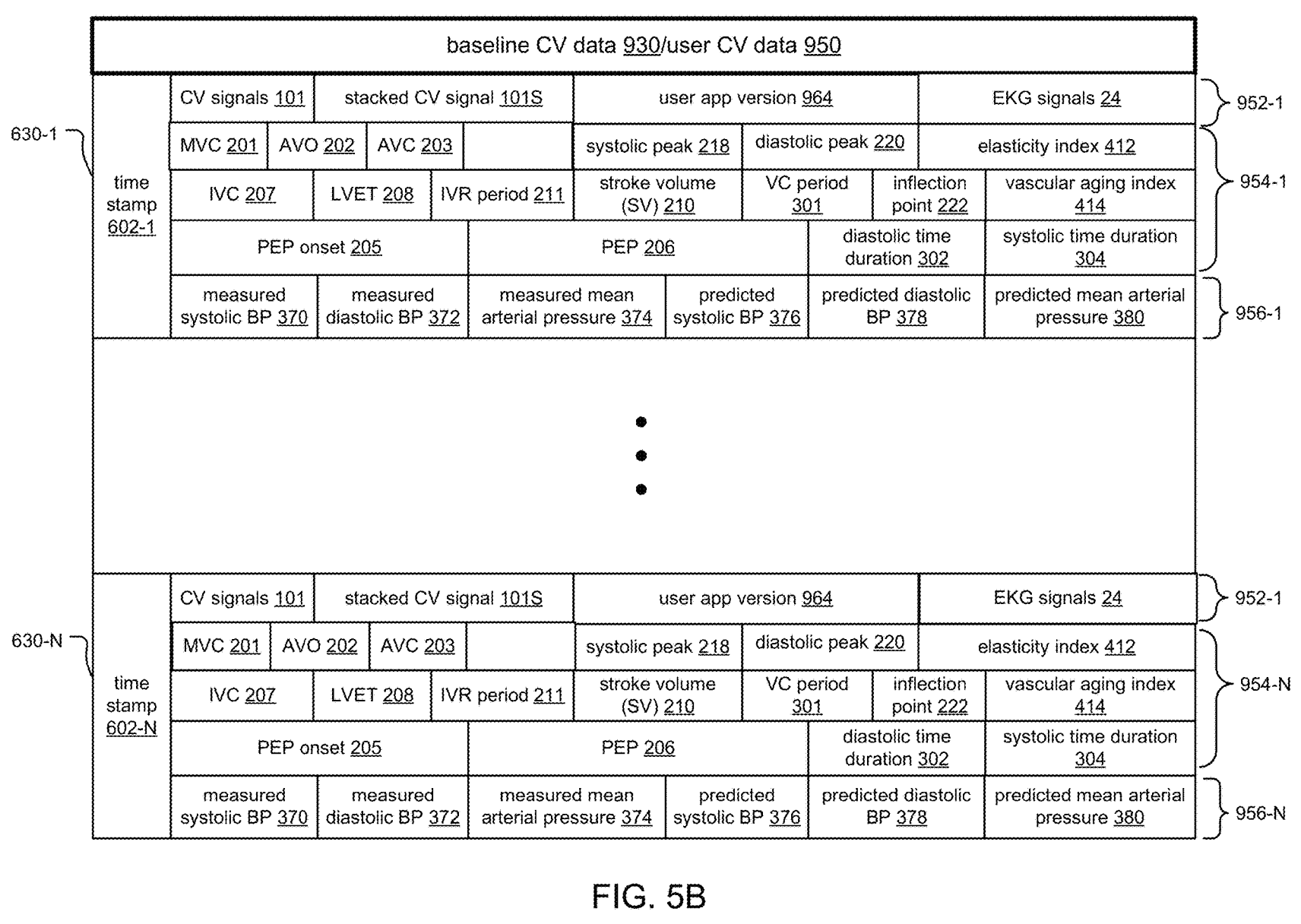

FIG. 5B also shows detail for the baseline CV data 930 and user CV data 950 fields within an individual's medical record 50. The baseline CV data 930 and user CV data 950 generally have the same structure and content. Here, the baseline CV data 930 and user CV data 950 are created and populated by the CV monitoring system 10B of FIG. 1B.

The baseline CV data 930 and user CV data 950 have the same content and structure as that shown in FIG. 5A. However, the baseline CV data 930 and user CV data 950 include additional fields, due to the presence and use of the EKG detection systems 18 in FIG. 1B. In more detail, the detected information 952 additionally includes EKG signals 24 detected by one or more of the EKG detection systems 18. The calculated CV function measurements additionally include a pre-ejection period onset (PEP onset) 205, a pre-ejection period (PEP) 206, a diastolic timing duration 302, and a systolic timing duration 304.

It can also be appreciated that many other CV function measurements other than the measurements 954 listed in FIGS. 5A and 5B can be obtained/calculated by the CV monitoring system 10. In non-limiting examples, CV function measurements including a rapid ejection period, a reduced ejection period, a rapid ventricular filling period, and a reduced ventricular filling period can also be obtained.

Figure 6:
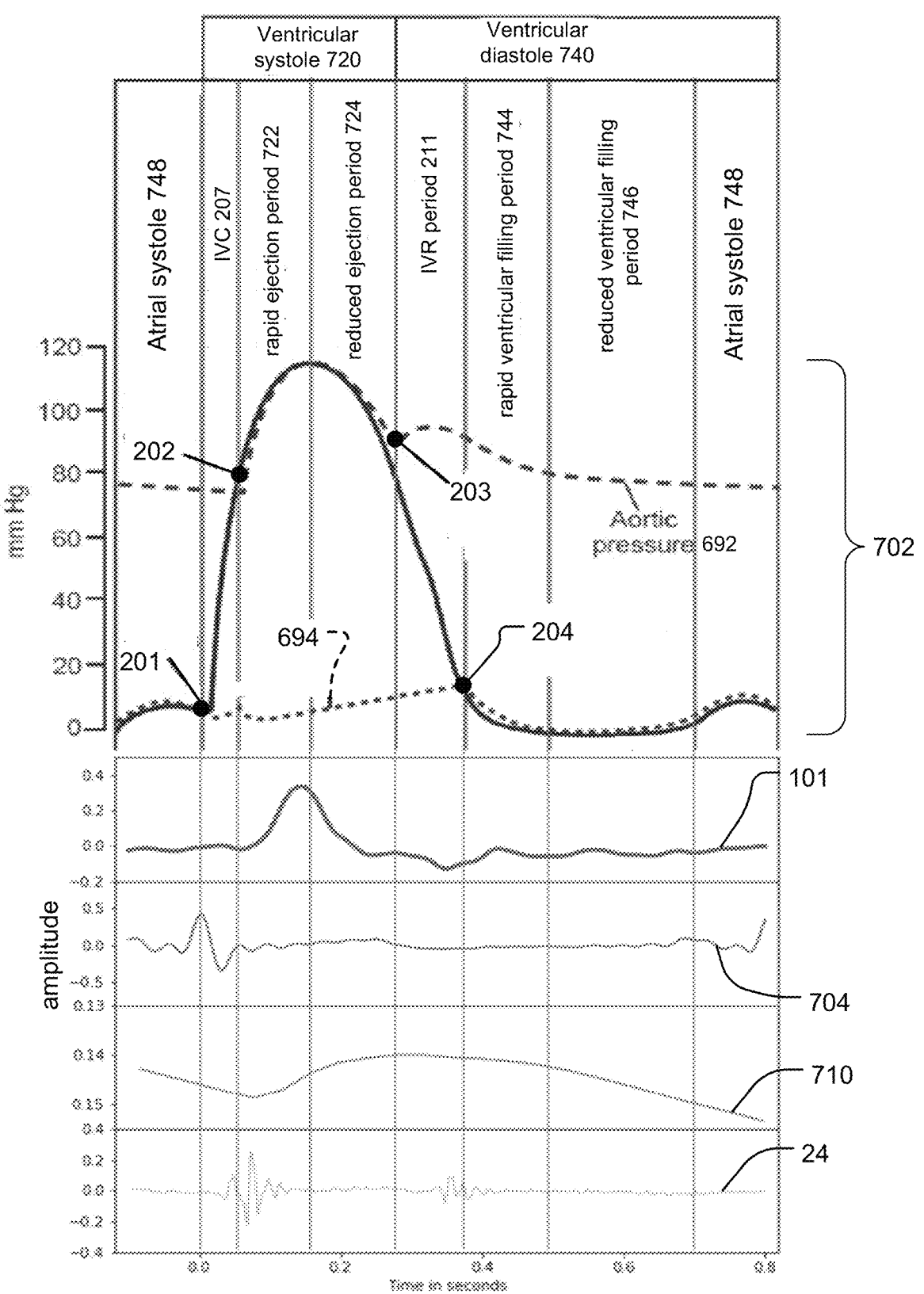
FIG. 6 is a Wiggers diagram that plots exemplary signals/waveforms associated with cardiovascular activity from different medical diagnostics systems, on a same time scale, and references some CV function measurements relative to each of the signals for comparison.

FIG. 6 is an augmented Wiggers diagram that illustrates operation of the left ventricle 314 for the same individual 100 over a single cardiac cycle. The diagram includes plots obtained by various medical diagnostics systems and/or reference BP monitoring systems, and includes a plot of a CV signal 101 obtained by the CV monitoring system over the same time frame for comparison.

From the top down, the diagram shows a BP plot 702 obtained by a BP cuff system, a CV signal 101 obtained by the CV monitoring system 10 and a phonocardiograph signal 704 from a phonocardiogram (PCG) system. Next is a photoplethysmogram signal 710 obtained by a photoplethysmography (PPG) system, and an EKG signal 24 obtained by an EKG system. The pressure shown in this diagram is the aortic pressure. Each of the signals represent activity of the left ventricle 314 of an individual's heart 30 over a single cardiac cycle.

Some cardiac function measurements are shown in the diagram, relative to the plots. These measurements include the MVC 201, the AVO 202, the AVC 203, and the MVO 204. Also shown is the IVC 207, the IVR period 211, an atrial systole 748, a rapid ejection period 722, a reduced ejection period 724, a rapid ventricular filling period 744, and a reduced ventricular filling period 746.

When blood pressure is measured using the BP cuff system, the upper value is the systolic pressure and the lower value is the diastolic pressure. The difference between the systolic and diastolic pressures is the aortic pulse pressure 692, which typically ranges between 40 and 50 mmHg. Atrial pressure 694 is also shown.

The remaining plots have scalar amplitude values. For the remainder of the description of FIG. 6, current medical diagnostics systems that can calculate various cardiac function measurements 954 are contrasted against the ability of the CV monitoring system 10 to calculate the same measurements.

It is important to note that none of the existing medical diagnostics systems can calculate all of the CV function measurements 954 individually. Rather, multiple existing medical diagnostics systems must be used to obtain all of the measurements. The individual 100 must visit clinics of possibly different medical professionals 110, who each often specialize in and have access to only one of the medical diagnostics systems. In contrast, the CV monitoring system 10 can calculate all of the CV function measurements 954, and without requiring an office visit and an administrator.

By way of background, multiple existing medical diagnostics systems must be currently used to calculate all of the CV function measurements 954 for the following reasons. In one example, the EKG signals 24 from the EKG detection systems 18 can be used to accurately calculate a starting point of the systolic time duration 304 and to detect heart rhythms, but generally do not provide an exact point in time where heart valves open or close. Using the EKG signals 24 only, cardiologists must use approximations to estimate the heart valve opening and closing times and the systolic time duration 304. In contrast, the echo system is designed to specifically and accurately calculate heart valve opening and closing times including the AVO 202, a mitral valve opening time (MVO), the MVC 201 and AVC 203. However, the echo system is generally ill-suited for obtaining other CV function measurements. The phonocardiograph signals 704 obtained by the PCG system are associated with audible heart sounds and can be used to detect heart murmurs. However, S1 and S2 waves in the signals 704 can only roughly indicate the MVC 201 and the AVC 203, respectively, and cannot provide information about valve opening times. In yet another example, the PEP 206 is the difference between the onset of left ventricular depolarization and the AVO time 202. While the onset of left ventricular depolarization is accurately indicated by the onset of the QRS complex in an EKG signal 24, the echo system is required to obtain the AVO time 202.

For calculating the MVC time 201, current medical diagnostics systems including the PCG, echo, and some invasive systems can be used. However, most of these systems require external equipment placed over the heart/chest area and generally a secondary administrator/medical professional 110 must administer the test. In contrast, the CV monitoring system can calculate this measurement individually.

For calculating the AVO time 202, the echo system is typically used. The CV monitoring system 10 also calculates the AVO time 202, and additionally calculates the LVET 208, which is used as a noninvasive measure of cardiovascular health. The CV monitoring system 10 can also use the LVET 208 to determine various other measurements such as the stroke volume (SV) 210, a left ventricle ejection fraction, and also to identify general aortic and ventricle functioning, in examples.

To calculate the AVC time 203, current medical diagnostics systems including the echo system and some invasive methods can be used. However, as with all uses of the echo system, a trained technician in a clinical setting is required and the equipment is expensive. In contrast, the CV monitoring system 10 can easily detect and calculate the AVC time 203. Moreover, the system 10 can use the AVC time 203 to determine the onset of the LVET 208. The system 10 can also use the AVC time 203 to determine various other measurements such as the SV 210, left ventricle ejection fraction, and general aortic and ventricle functioning.

Calculation of the PEP 206 currently requires using a combination of the EKG and ICG or echo systems, or an invasive system. The ICG system measures electrical currents that control the rhythmic contraction cycles of the heart. The onset of the QRS complex in the EKG signal 24 indicates the start time of the PEP 206 while the detection of the AVO time on the EKG signal indicates the end time of the PEP 206. Additionally, invasive systems such as impedance cardiography can be used, where the PEP 206 is represented by the first derivative of the thorax impedance change.

In contrast, the PEP 206 is easily determined by the CV monitoring system 10B and is considered to be a direct representation of the degree of sympathetic nervous system (SNS) activation. As a result, the system 10 can use the PEP 206 to determine the relative degree of stress the individual 100 is experiencing. Additionally, the CV monitoring system 10 can calculate a ratio of the PEP 206 to the LVET 208 to obtain a systolic time index. This index is considered to be a noninvasive determinant of cardiac health and efficiency.

Specifically, the PEP 206 and the systolic time index are representative of the myocardial contractility of the heart 30 and can be used to noninvasively determine whether there is an abnormality in the heart contraction pattern and strength.

For the LVET 208, the echo system can typically calculate this measurement. Alternatively, a combination of EKG and PCG systems or EKG and ICG systems can estimate this measurement, but require extensive preprocessing that allows for the identification of the AVO time 202 and the AVC time 203 (from which the LVET 208 is determined). Alternative methods require combining measurements obtained from echo and PCG systems, or EKG.

In contrast, the LVET 208 is easily determined by the CV monitoring system 10, and fluctuations in the LVET 208 can be considered with variations in the SV 210 to determine cardiac efficiency. Moreover, discrepancies between the LVET 208 and the SV 210 can also be used to determine aortic abnormalities such as aortic stenosis. In addition, the LVET 208 also provides the denominator for the systolic time index. Finally, the LVET 208 is used as an effective noninvasive determinant of myocardial contractility. For this purpose, a myocardial performance index can be calculated using the LVET 208, where the ejection time is compared with both the IVC 207 and IVR periods 211, which immediately precede and succeed the LVET 208. This index provides immediate information regarding the initiation, duration, and recovery behavior of the heart contraction and can detect whether there is an abnormality in the contraction mechanism.

As to the IVC 207, the echo system typically obtains this measurement. This interval is typically provided as an estimate by the echo system, but such an estimate is rarely used for clinical evaluation. In contrast, the CV monitoring system 10 can easily and accurately determine the IVC 207. Using the IVC 207, the system can calculate the myocardial performance index. This index provides immediate information regarding the initiation, duration, and recovery behavior of the heart contraction and can detect whether there is an abnormality in the contraction mechanism. When observed immediately after a heart attack, or myocardial infarction, this index has also been shown to be predictive of the degree of ventricular function post attack. Additionally, this index has been shown to have superior specificity and accuracy in detecting chronic heart failure than other more invasive measures such as left ventricle ejection fraction. This index is also significantly correlated with max dP/dt of ventricular contraction, the official index of contractile performance and indicative of left ventricle ejection fraction and stroke volume.

As to the IVR 211, the echo system typically obtains this measurement. This interval can also be estimated by echo and seismograph, but these estimates are rarely used for clinical evaluation. In contrast, the CV monitoring system 10 can easily and accurately determine the IVR 211. Using the IVR 209, the system 10 can also calculate the myocardial performance index.

The diastolic time duration 302 and the systolic time duration 304 are currently measured using an EKG system in conjunction with the echo system. However, the CV monitoring system 10B in FIG. 10B can also determine these measurements. This is because the CV monitoring system 10B includes one or more EKG detection systems that detect and send EKG signals 24 of the individual 100 to the data analysis system 2019 for analysis. The data analysis system 209 determines the diastolic time duration 302 and the systolic time duration 304 based upon the combination of EKG signals 24, and CV signals 101; and can use these CV function measurements in conjunction with the CV function measurements obtained from the CV signals 101 to obtain additional CV function measurements.

Figure 7:
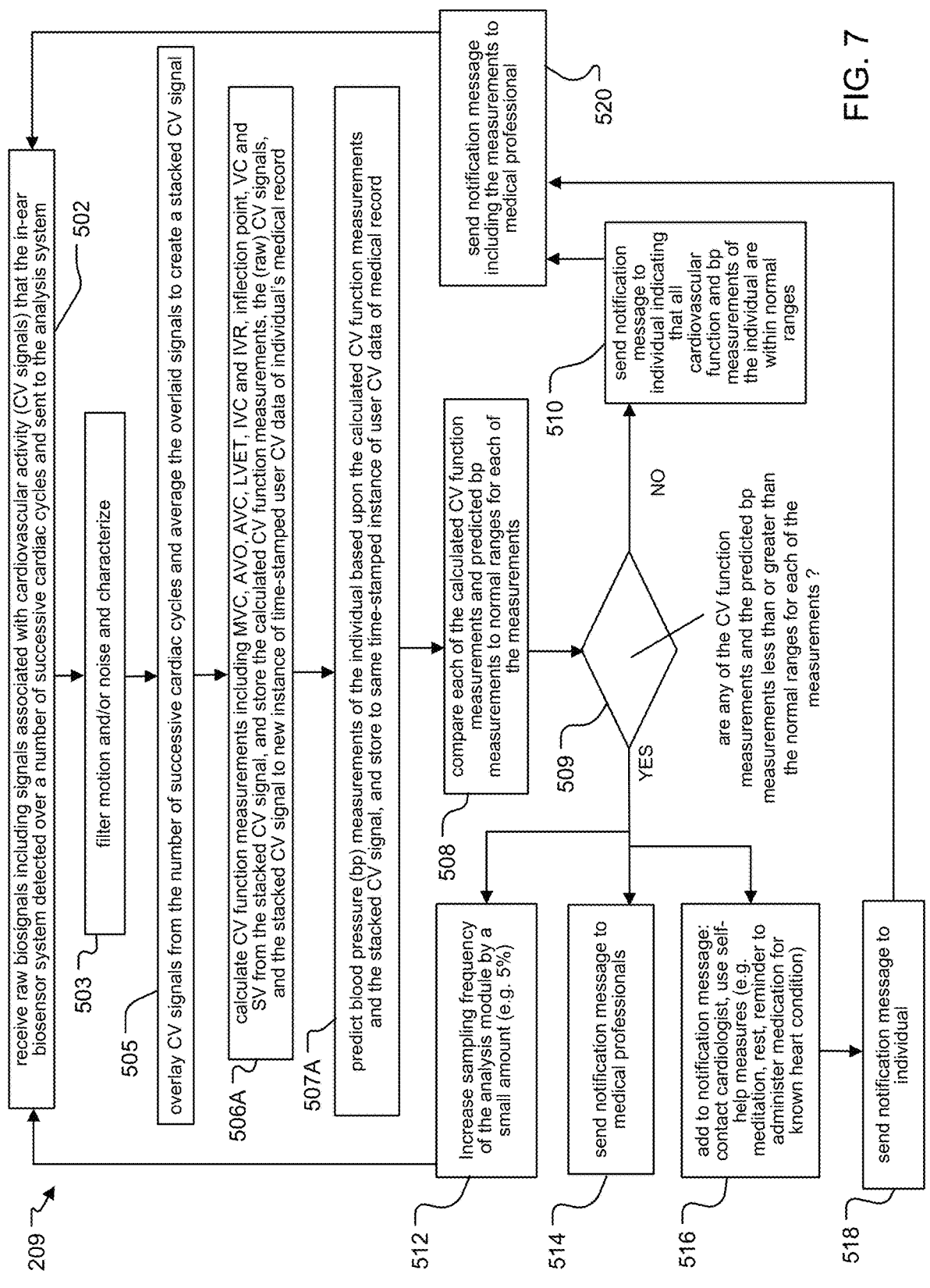
FIG. 7 is a flow diagram that illustrates a method of operation of the data analysis system in the CV monitoring systems of FIGS. 1A and 1B.

FIG. 7 is a flow diagram that describes an exemplary method of operation of the data analysis system 209. In one example, the data analysis module 180 of the data analysis system 209 performs this method.

In step 502, the analysis module 180 receives raw biosignals including CV signals 101 that the in-ear biosensor system detected over a number of successive cardiac cycles and sent to the analysis system 209. In step 503, the module 180 filters motion and/or noise from the biosignals and characterizes the biosignals as being CV signals 101 or pressure signals, in examples. Then, in step 505, the method creates a stacked CV signal 101S from the CV signals 101. Specifically, the method overlays/superimposes the CV signals upon one another in a stacked fashion, and creates a stacked CV signal 101S that is an average value of the overlaid CV signals 101.

According to step 506A, the module 180 calculates CV function measurements 954 from the CV signals 101/the stacked CV signal 101S. These include the MVC 201, AVO 202, AVC 203, MVO 204, LVET 208, IVC 207 and IVR 211, inflection point 222, VC period 301 and SV 210. The module 180 then stores these measurements to a new instance of time-stamped user CV data 950 within the individual's medical record 60.

In step 507A, the analysis module 180 predicts BP measurements of the individual based upon the calculated CV function measurements 954 and the CV signals 101/ stacked CV signal 101S. These predicted measurements include the predicted systolic BP 376, the predicted diastolic BP 378, and the predicted mean arterial pressure 380. The module 180 then stores these predicted BP measurements to the aggregated BP measurements 956 of the same time-stamped instance of user CV data 950 as in step 506A.

According to step 508, the analysis module 108 compares each of the calculated CV function measurements 954 to the normal ranges for each of the CV function measurements 932 stored in the medical records 50 of the individuals 100. The normal ranges 932 include standard normal ranges and individual-specific ranges for each of the measurements. The standard ranges, in examples, can include ranges for groups of individuals 100 such as all adults, or for cohorts such as adults over the age of 50, or possibly even a subset of individuals having similar cardiac conditions. In a similar vein, the analysis module 180 also compares each of the predicted BP measurements to normal ranges (standard and/or individual-specific) for each of the BP measurements 934. The normal ranges 934 are also obtained from the individual's medical record 50.

In step 509, the analysis module 108 determines whether any of the calculated function measurements 954 are less than or greater than their normal ranges 932 (e.g. standard and individual-specific) and whether any of the predicted BP measurements are less than or greater than their normal ranges 934 (e.g standard and individual-specific). If any of the CV function measurements 954 or the predicted BP measurements are outside their normal ranges 932/934, respectively, the method transitions to steps 512, 514, and 516. Otherwise, the method transitions to step 510.

Additionally or alternatively, the analysis module 180 in step 508 might also compare each of the calculated CV function measurements 954 to the threshold percentage change values of the CV function measurements 936 for the individual 100 and compare each of the predicted BP measurements to the threshold percentage change values of the BP measurements 938 for the individual 100. The threshold percentage change values 936 are specific to each of the CV function measurements 954 and are user-specific/ obtained from the individual's medical record 50. Similarly, the threshold percentage change values of the predicted BP measurements 938 are specific to each of the predicted BP measurements and are user-specific/obtained from the individual's medical record 50.

The threshold percentage change values 936, 938 may be able to detect issues in otherwise healthy individuals 100 that have a sudden change to their cardiac health that they are not aware of/is asymptomatic, in one example. Such a change might be an anomaly and an early sign of trouble for an otherwise healthy individual 100, but this change could escape detection if the measurements 954 were compared only to their normal ranges 932. For example, a 10% change to a particular CV function measurement 954 could still be within the normal range 932 for that measurement, but is unusual for the individual 10. For this purpose, the individual might set a threshold percentage change 936 value of 5% in association with this measurement. In this way, significant skips or jumps that are still within normal ranges in one or more of the CV functions measurements for that individual 100 can be detected and reported.

Steps 512, 514, and 516 are executed in parallel when any of the CV function measurements 954 or any of the predicted BP measurements were determined to be less than or greater than their normal ranges 932, 934. In step 512, the analysis module 180 increases a sampling frequency for sampling the CV signals 101 by a small amount (e.g. 5%), and the method transitions to step 502 to obtain a new set of biosignals/CV signals 101. In addition, the method in step 514 sends notification messages 111 to the medical professionals 110 regarding the results of the analysis. In step 516, the analysis module 516 might also add information to a notification message for transmission to the individual 100. The information might suggest that the individual 100 contact his/her cardiologist, and/or use self-help measures (e.g. meditation, rest, reminder to administer medication for known heart condition), in examples.

The analysis module 180, in step 518, then sends the user notification message prepared in step 516 to the individual 100. The method then transitions to step 520, and the analysis module prepares and sends a notification message that includes the CV function measurements 954 and the calculated BP measurements to the medical professional 110. Upon conclusion of step 520, the method transitions to step 502 to obtain a new set of biosignals/CV signals 101.

FIG. 8 provides more detail for step 506A in the method of FIG. 7. Here, FIG. 8 describes a method of the analysis module 180. The method calculates some CV function measurements 954 in the CV monitoring system 10A of FIG. 1A. For this purpose, the analysis module 180 of the data analysis system 209 derives the CV function measurements from the stacked CV signal 101S.

In step 902, the analysis module 180 samples a segment of the stacked CV signal 101S and detects cardiac peaks. In step 904, the analysis module 180 calculates a heart rate of the individual 100 from the detected peaks. According to step 906, the analysis module 180 calculates a baseline LVET using a reference equation and the heart rate. Here, the baseline LVET is an approximate LVET describing a relationship between heart rate and the LVET 208. This baseline value is used to guide algorithms that the analysis module 180 executes for determining aortic valve opening and closing events within the stacked CV signal 101S, in one example.

Then, in step 910, the analysis module 180 calculates the systolic peak 218 by identifying the peak of the stacked CV signal 101S. In step 912, the analysis module 180 identifies a left time point of interest within the stacked CV signal 101, indicated by: systolic peak—(baseline LVET*0.3), and defines a left region of interest as a 50 ms time window starting from 20 ms before and 30 ms after the left point of interest.

The analysis module 180 calculates a first derivative and a second derivative of the stacked CV signal in step 914. In step 916, the analysis module 180 saves all points where the first derivative crosses the x-axis of the stacked CV signal 101S as first derivative zero crossings. According to step 918, the analysis module 180 calculates the aortic valve opening time (AVO) 202 by identifying a second derivative peak within the left region of interest.

In step 920, the analysis module 180 calculates the mitral valve closing time (MVC) 201 by accessing the first derivative zero crossings and identifying a positive-to-negative zero crossing immediately preceding the AVO 202. In step 922, the method calculates the diastolic peak 220 by accessing the first derivative zero crossings, and identifying a positive-to-negative zero crossing immediately following the AVO 202 and the baseline LVET. Then, in step 924, the method calculates the aortic valve closure time (AVC) 203 by identifying a second derivative peak between: (AVO 202+ baseline LVET–20 ms) and the diastolic peak 220.

According to step 926, the method calculates the inflection point 222 by identifying a second derivative peak between: (AVO 202+20 ms) and (AVC 203–20 ms). The method also calculates the VC period 301 as the difference between the MVC 201 and the AVC 203. In step 928, the method finds the area under curve (e.g. perform integration) for stacked CV signal 101S, from the AVO 202 as the starting point to the AVC 203 as the ending point, and normalizes and calibrate the integral to obtain the stroke volume (SV) 210 for the stacked CV signal 101S. In step 930, the analysis module 180 stores the calculated CV function measurements 954 to time-stamped user CV data 950 within the medical record 50 of the individual 100, e.g. by sending a notification message including the calculated CV function measurements via the applications server 132 to the medical record database 90.

Figure 9:
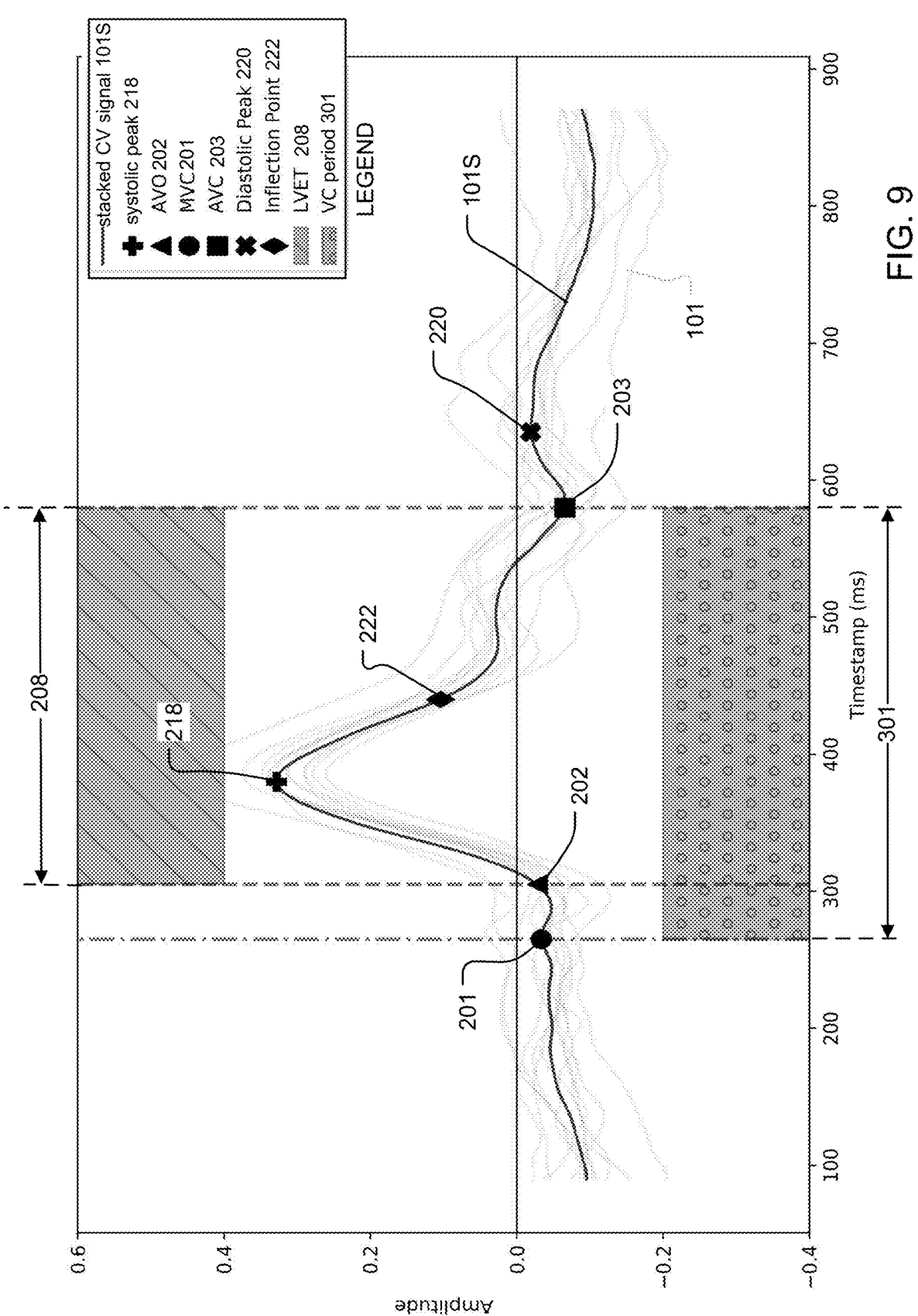
FIG. 9 is a plot of CV signals obtained from multiple successive cardiac cycles of an individual from one earbud of an in-ear biosensor system, where the CV signals are averaged to form a stacked signal, and where the plot illustrates how the method of FIG. 7 can calculate various CV function measurements from the CV signals via the stacked CV signal.

FIG. 9 shows CV signals 101 obtained by the in-ear biosensor system 102 over a number of successive cardiac cycles. The CV signals 101 are from only one "channel" or earbud 103. The figure illustrates the calculation of various cardiovascular function measurements 954 in accordance with the method of FIG. 8.

In the illustrated example, the CV signals 101 are superimposed upon one another, or "stacked," and an average CV signal waveform also known as a stacked CV signal 101S is determined from the CV signals 101. This figure also illustrates calculation of various cardiovascular function measurements 954 in accordance with the method of FIG. 8. These cardiovascular function measurements 954 are calculated based upon the CV signals 101 by deriving their values from or in relation to the stacked CV signal 101S determined from the CV signals 101 (more specifically, from an in-memory representation of the stacked CV signal 101S).

Various CV function measurements 954 relative to the stacked CV signal 101S are shown. These measurements include the MVO 201, AVO 202, AVC 203, systolic peak 218, diastolic peak 220, SV 210, VC period 301, inflection point 222 and LVET 208.

FIG. 10 provides more detail for step 507A in the method of FIG. 7.

Here, the data analysis system uses a machine learning model 187 that the data analysis system 209 has previously created (i.e. trained) from training data in the training data repository 70. In one implementation, the training data includes anonymized versions of calculated CV function measurements 954 and/or raw CV signals 101 copied from the medical records 50 of multiple individuals 100, along with corresponding reference BP measurements of the multiple individuals 100 obtained from one or more reference BP monitoring systems. In another implementation, the training data might include CV function measurements and corresponding BP measurements calculated from synthetic waveforms generated from one or more blood pressure models.

In step 970, the analysis module 180 accesses stacked CV signals 101S and calculated CV function measurements 954 for multiple individuals 100. In one example, this information is in anonymized form and included in training data within the training data repository 70. In another example, the analysis module 180 might query this information directly from the medical records 50 of selected individuals 100. The analysis module 180 then anonymizes the information before use. In this example, the medical records 50 selected were in response to instructions provided by a medical professional 110 via the application server 132. In this way, the medical professionals 110 can specify criteria that enables selection of medical records 50 for a specific age, race, sex, or gender cohort, or any combination of these criteria.

According to step 972A, the method selects at least some of the calculated CV function measurements (e.g. AVO 202, AVC 203, systolic peak 218, diastolic peak 220, and inflection point 222) of the multiple individuals to use as input to a pre-existing machine learning model 187 that was previously trained (i.e. created) by the data analysis system 209. The method in step 974 then fits an asymmetric Gaussian mixture model having at least two components within the stacked CV signals 101S, using constraints derived from the systolic peak 218, the AVO 202 and the AVC 203 of the calculated CV function measurements 954.

In step 976, the method performs a principal components analysis on the stacked CV signals 101S to obtain a minimum number of principal components that can recreate the stacked CV signals 101S. Then, in step 978, the method performs a Fourier analysis (e.g. discrete Fourier transform, fast Fourier transform) on the stacked CV signals 101S and extracts CV signal metadata including frequencies, amplitudes and phase difference values. In step 980, the method passes the fitted Gaussian mixture model, the minimum number of principal components and the extracted CV metadata along with the selected CV function measurements as input to the machine learning model 187.

As a result, the input applied to the model 187 not only includes the CV signals 101 and the calculated CV function measurements 954 that the CV monitoring system 10 obtained for the current individual 10, but can also include different combinations of the following: stacked versions of CV signals and calculated CV function measurements previously obtained for other individuals; an asymmetric Gaussian mixture model with at least two components fitted within the stacked CV signals; a minimum number of principal components that can recreate the stacked CV signals; and CV signal metadata extracted from the stacked CV signals that includes frequencies, amplitudes, and phase difference values of the stacked CV signals.

In step 982, the method applies the inputs to the machine learning model 187 to predict BP function measurements for the individual 100 as output of the model 187. The method in step 984 then stores the predicted BP measurements to time-stamped user CV data 950 within the medical record 50 of the individual 100. For this purpose, in one example, the analysis module 180 might send a notification message 111 including the predicted BP measurements via the applications server 132 for updating the medical record 50 in the medical record database 90.

Figure 11:
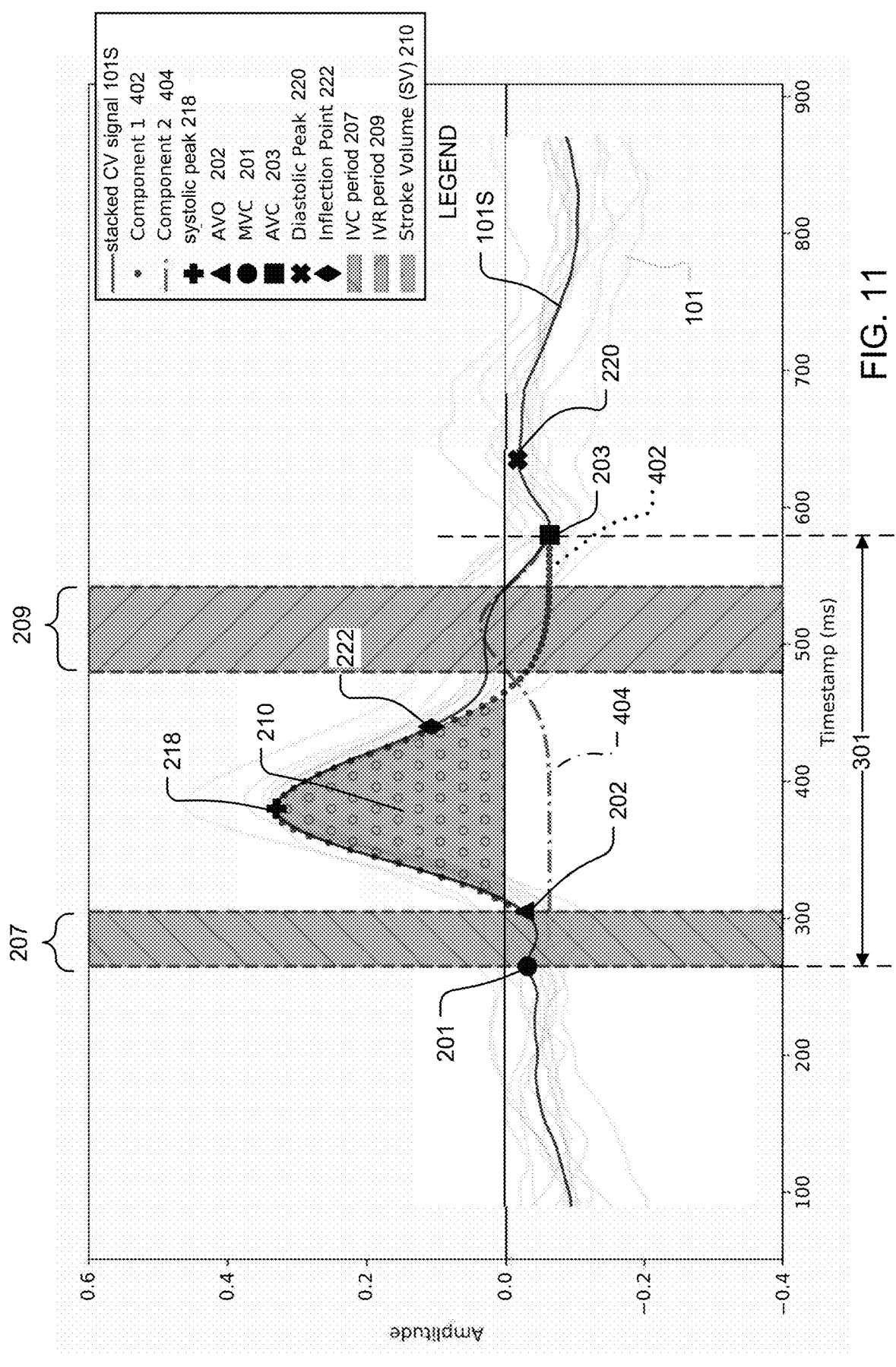
FIG. 11 is a plot of CV signals and an associated stacked CV signal as in FIG. 9 that further illustrates operation of the method of FIG. 7, and also illustrates operation of the flow diagram of FIG. 10.

FIG. 11 shows CV signals 101 obtained by the in-ear biosensor system 102 over a number of successive cardiac cycles. The CV signals 101 are from only one "channel" or earbud 103. The figure illustrates a portion of the method of FIG. 10 for predicting BP measurements of an individual 100. Specifically, the figure illustrates steps 972 through 974 in the method of FIG. 10 for preparing inputs to apply to machine learning model 187.

The illustrated example shows substantially similar information as that provided in FIG. 9. However, there is some additional information. More CV function measurements 954 derived from/relative to the stacked CV signal 101S and an asymmetric Gaussian mixture model fitted to the stacked CV signal 101S are shown. Additional CV function measurements 954 such as IVC period 207, IVR period 209 and SV 210 are shown.

Figure 12A:
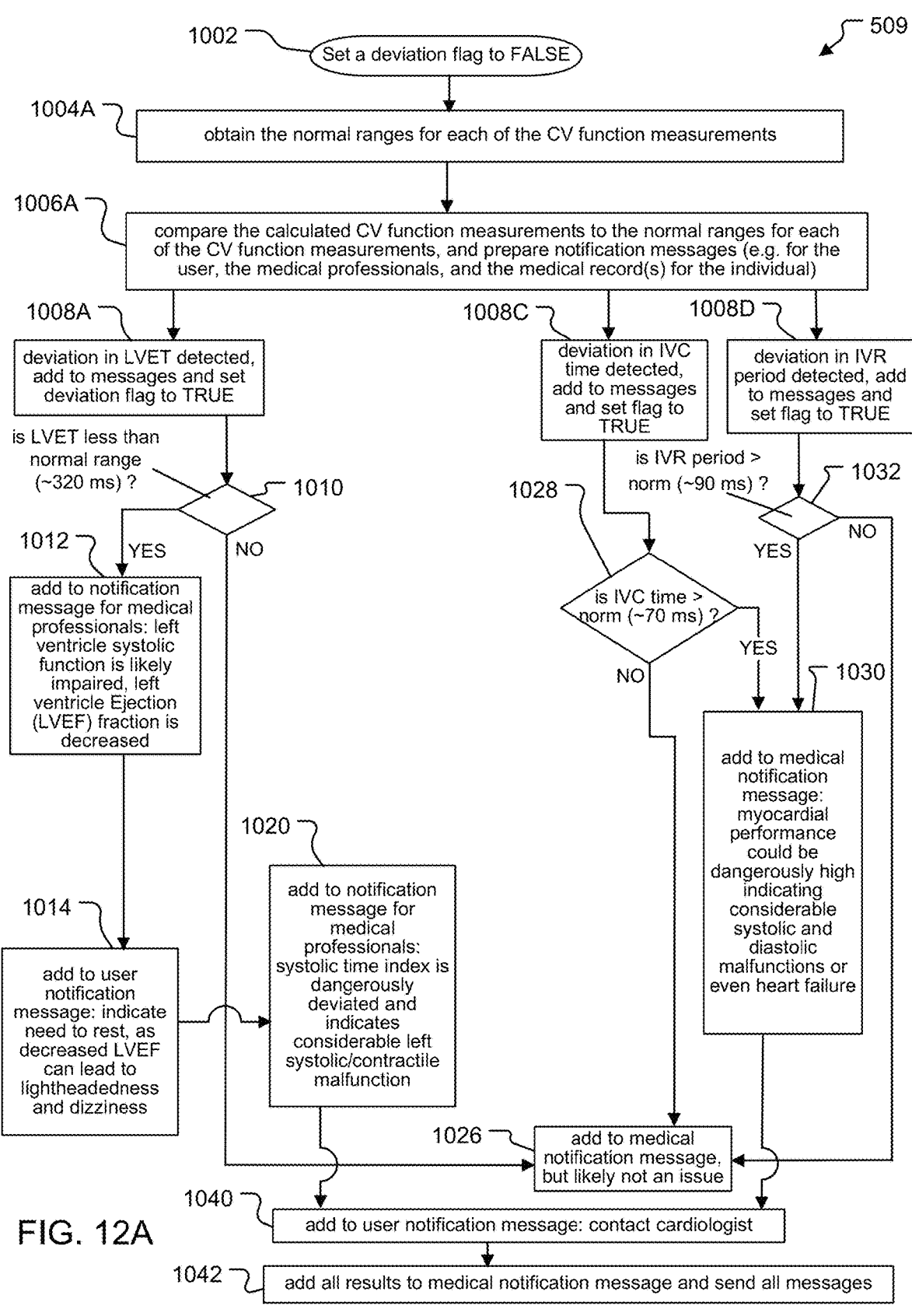
FIG. 12A is a flow diagram that provides more detail for the method of FIG. 7, where the diagram shows how the data analysis system compares the calculated CV function measurements for an individual to normal ranges for each the measurements and notifies the individual and medical professionals in response to the comparisons.

FIG. 12A provides more detail for step 509 in the method of FIG. 7. Here, FIG. 12A describes a method of the analysis module 180. The method provides more detail for how the analysis module 180 determines whether any of the calculated CV function measurements 954 are less than or greater than their normal ranges 932 for each of the CV function measurements 954. Values that are less than or greater than their normal ranges are also known as being "outside of" their normal ranges.

Values for the CV function measurements 954 that are determined to be outside the normal ranges are referred to as deviations. In the illustrated example, all of the CV function measurements 954 are compared to their corresponding normal ranges 932. However, only the processing of deviations detected for the LVET 208, IVC period 207, and IVR period 209 are shown. The processing of deviations for these measurements are selected because they are included among the measurements that are most associated with the systolic time duration 304.

In the method below, the data analysis module 180 of the data analysis system 209 can identify possible heart conditions based on the CV function measurement comparisons and possibly in conjunction with other defined qualifying criteria. The analysis module 180 can then notify the individual 100 and/or at least one medical professional 110 in response. The method begins in step 1002.

According to step 1002, the analysis module 180 sets a Boolean deviation flag to FALSE, and obtains the normal ranges for each of the CV function measurements 954 in step 1004A. In one implementation, the normal ranges 932 are obtained by the user app 40 executing on the user device 107 once the user is authorized. For this purpose, the user device 107 obtains the medical record 50 for the user from the medical record database 90 via the application server 132. The user device 107 extracts the normal ranges (e.g. standard and individual-specific) of the cardiac function measurements 932 from the medical record 50, and sends the normal ranges 932 to the data analysis system 209. In another example, cached values for the normal ranges 932 are maintained on the user device 107.

In step 1006A, the module 180 compares the calculated CV function measurements 954 to the normal ranges 932 for each of the measurements, and prepares various notification messages 111. These include user notification messages for sending to the user of the CV monitoring system 10, medical notification messages for sending to the medical professionals 110, and record notification messages for sending information including the detected information 952 and the calculated CV measurements 954 to update the medical record 50 in response to completion of the analysis. In one example, the module 180 sends these messages to the application server 132, which forwards the messages to proper destination based on message type or destination address.

Steps 1008A, 1008C, and 1008D describe details of deviation processing for the LVET 208, IVC period 207, and IVR period 209, respectively. When any deviations in the measurements in steps 1008A,C,D are found, the information is added to the notification messages 111 and the deviation FLAG is set to TRUE. The details in the deviation processing are other defined qualifying criteria that the analysis module 180 can use in conjunction with the normal range comparisons to determine whether heart conditions of the individual exist, and whether to send notifications 111 to the individuals 100 and/or to the medical professionals 110 in response.

In another implementation, the deviation processing can be less tailored to any given CV function measurement 954. For example, if any of the CV function measurements 954 are determined to deviate from their normal ranges 932 by three (3) standard deviations, the deviation flag will be set to TRUE.

In the remaining steps of FIG. 11, further measurement-specific processing is performed to determine the severity (if any) of the deviation(s). In step 1008A, a deviation in the LVET 208 is detected and the deviation flag is set to TRUE. In step 1010, the method additionally determines whether the LVET 208 is less than its normal range (e.g. −320 ms). If this statement is true, the method transitions to step 1010; otherwise, the method transitions to step 1026.

When the result of step 1010 is true, more information is added to a medical notification message for sending to a medical professional 110. Here, the information might include a suggestion that left ventricle function is likely impaired and a left ventricle ejection fraction (LVEF) is thus decreased. Results of the analysis are added to the notification messages 111. The method then transitions to step 1014, and more information is added to the message. This information might include the need for the individual 100 to rest, as decreased LVEF can lead to lightheadedness and dizziness, in examples. The method then transitions to step 1020, and more information is added to the message.

In step 1020, more information is added to the medical notification message 111. This information includes an inference that a systolic time index is dangerously deviated and indicates considerable left systolic/contractile malfunction. The method transitions to step 1040.

When the result of step 1010 is false, the method transitions to step 1026 and the information requested for addition to the medical notification messages 111 from any previous step that entered step 1026 are finalized. This information is added to the medical notification message for subsequent transmission to medical professionals 110, though the information likely does not indicate a medical issue that merits concern.

In step 1008C, a deviation in the IVC period 207 is detected and the deviation flag is set to TRUE. In step 1028, the method additionally determines whether the IVC period 207 is less than its normal range (e.g. −70 ms). If this statement is true, the method transitions to step 1030; otherwise, the method transitions to step 1026.

According to step 1030, the method adds information to the medical notification message. The information suggests that myocardial performance could be dangerously high indicating considerable systolic and diastolic malfunctions or even heart failure, and the method transitions to step 1030.

In step 1008D, a deviation in the IVR period 211 is detected and the deviation flag is set to TRUE. In step 1032, the method additionally determines whether the IVR period 211 is less than its normal range (e.g. −90 ms). If this statement is true, the method transitions to step 1030; otherwise, the method transitions to step 1026.

In step 1040, a suggestion indicating that the individual 100 should contact their cardiologist is added to the user notification message 111. The method transitions to step 1042, where the method adds all results from the comparisons to the medical notification message and sends all messages 111. In this way, in response to the CV measurement comparisons, the data analysis system 209 can notify the individual to engage in self-help activities including the need to rest, and to contact medical professionals such as cardiologists for follow-up.

Figure 12B:
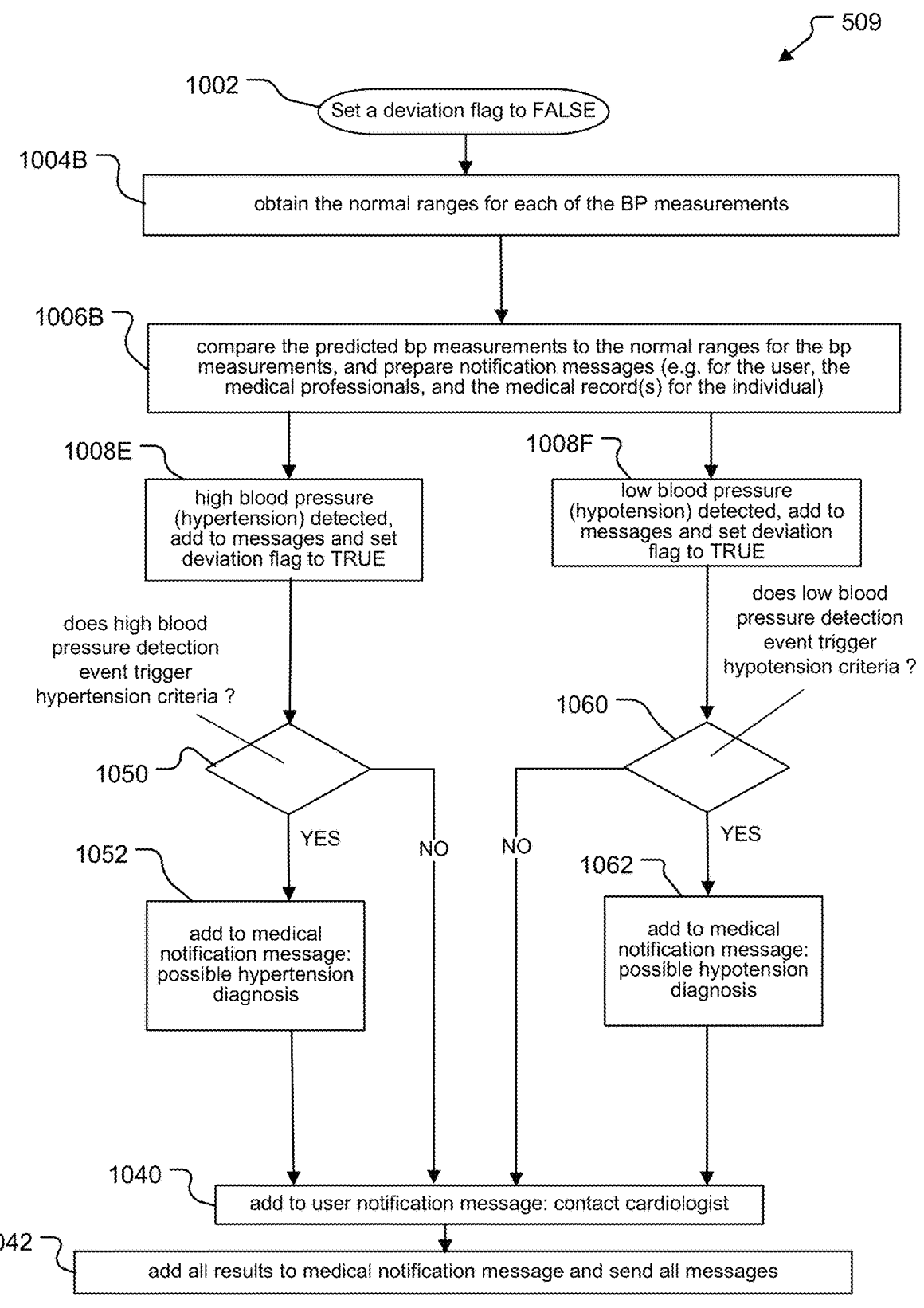
FIG. 12B is a flow diagram that provides more detail for the method of FIG. 7, where the diagram shows how the data analysis system compares the predicted BP measurements for an individual to normal ranges for each of the measurements, and in response to the comparisons, can notify the individual and medical professionals of possible hypertension or hypotension.

FIG. 12B also provides more detail for step 509 in the method of FIG. 7. Here, FIG. 12B describes a method of the analysis module 180. The method provides more detail for how the analysis module 180 can determine whether any of the predicted BP measurements are less than or greater than the normal ranges 934 for each of the BP measurements. The method further describes how the data analysis system 209 can identify possible health conditions including hypertension and hypotension based on the comparisons and possibly in conjunction with other defined qualifying criteria, and notifies the individual 100 and at least one medical professional 110 in response.

According to step 1002, the module 180 sets a Boolean deviation flag to FALSE, and obtains the normal ranges for each of the BP measurements 934 in step 1004B. In step 1006B, the analysis module 180 compares the predicted BP function measurements to the normal ranges 932 for each of the BP measurements, and prepares various notification messages 111. These include user notification messages for sending to the user of the CV monitoring system 10, medical notification messages for sending to the medical professionals 110, and record notification messages for sending information including the detected information 952 and the predicted BP measurements to update the medical record 50 in response to completion of the analysis.

Steps 1008E and 1008F respectively describe how the analysis module 180 can determine whether hypertension or hypotension are detected, based upon the comparisons performed in step 1006B and in conjunction with other defined criteria, such as hypertension and hypotension criteria.

Step 1008E detects hypertension in the individual 100 and sets the deviation flag to TRUE in response. In step 1050, the method then determines whether the detection of high blood pressure triggers hypertension criteria. Hypertension criteria includes analyzing historical stored user data and detecting repeat/consistent detection of high BP within a specified time frame, or monitoring rate of change over a specified time frame, in examples, to qualify for a notification.

If the criteria is triggered, the method transitions to step 1052; otherwise the method transitions to step 1040. In step 1052, the method adds information to a medical notification message indicating a possible hypertension diagnosis. The method then transitions to step 1040.

Step 1008F detects hypotension in the individual 100 and sets the deviation flag to TRUE in response. In step 1060, the method then determines whether the detection of low blood pressure triggers hypotension criteria. If the criteria is triggered, the method transitions to step 1062; otherwise the method transitions to step 1040. In step 1062, the method adds information to a medical notification message indicating a possible hypotension diagnosis. The method then transitions to step 1040.

In step 1040, a suggestion indicating that the individual 100 should contact their cardiologist is added to the user notification message 111. The method transitions to step 1042, where the method adds all results from the comparisons to the medical notification message and sends all messages 111.

Figure 12C:
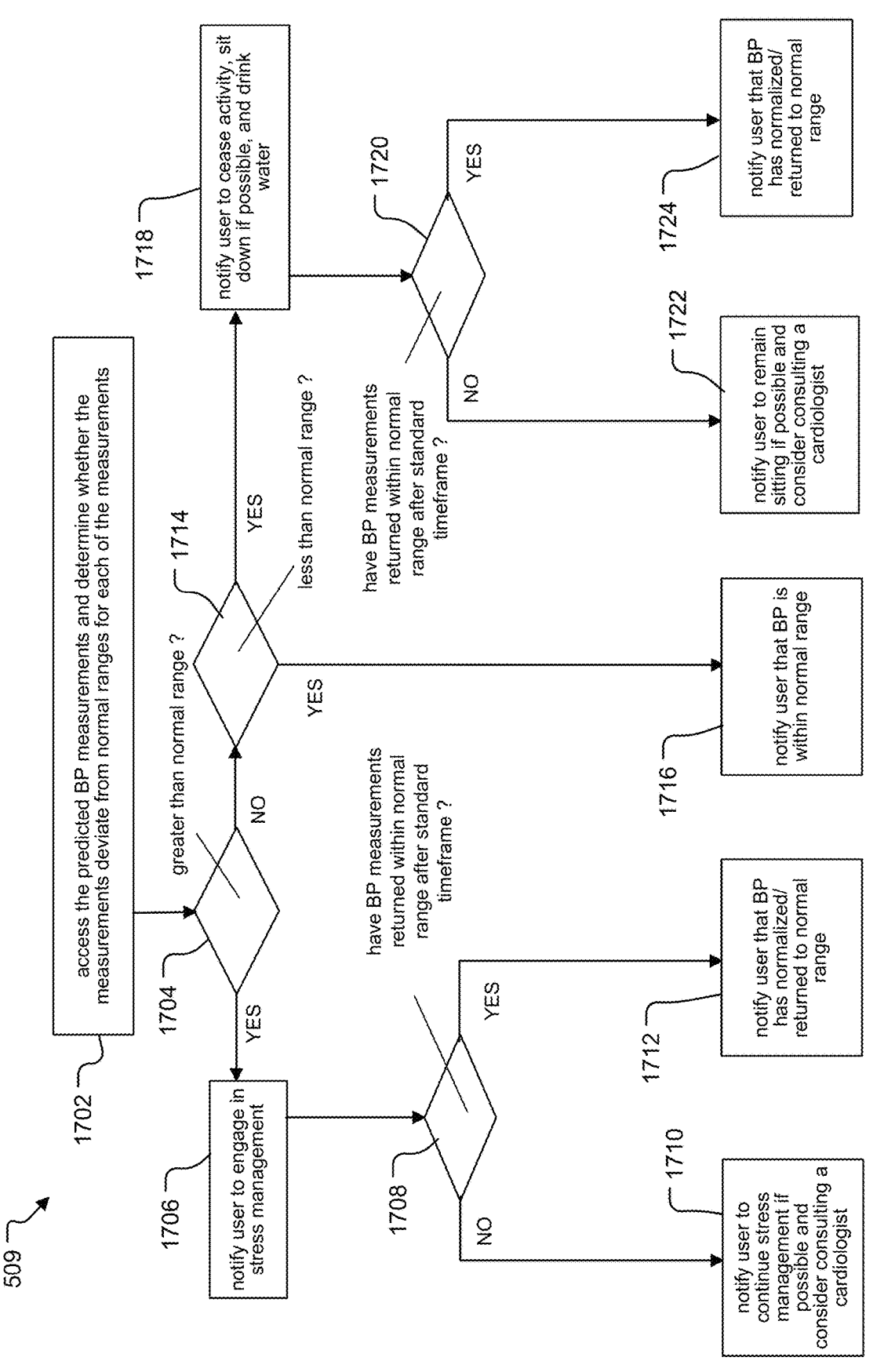
FIG. 12C is a flow diagram that provides more detail for the method of FIG. 7, where the diagram shows how the data analysis system compares the predicted BP measurements for an individual to normal ranges for each of the measurements as in FIG. 12B, but instead can notify the individual to possibly engage in stress management in response to the comparisons.

FIG. 12C also provides more detail for step 509 in the method of FIG. 7. Here, FIG. 12C describes one implementation for a method of the analysis module 180. The method provides more detail for how the analysis module 180 can determine whether any of the predicted BP measurements are less than or greater than the normal ranges 934 for each of the BP measurements. The method can then recommend the individual 100 engage in self-help activities such as stress management in response to the comparisons.

In step 1702, the method accesses the predicted BP measurements and determines whether any of the measurements are less than or greater than their normal ranges 934 for each of the BP measurements. If any of the BP measurements are greater than their normal ranges 934 in step 1704, the method transitions to step 1706. If any of the BP measurements are less than their normal ranges 934 in step 1714, the method transitions to step 1718. If all BP measurements are within their normal ranges 934, the method transitions to step 1716 and notifies the user that the BP measurements are within normal ranges.

In step 1706, the method notifies the user (e.g. via a user notification message 111) to engage in stress management. In step 1708, the method determines whether the BP measurements have returned within normal ranges after a standard timeframe, such as 15 minutes or as much as 30 minutes. If the BP has returned to normal within the timeframe, the method notifies the user in step 1710 to continue stress management if possible and consider consulting a cardiologist. Otherwise, the method transitions to step 1712 and notifies the user that the BP measurements have normalized/returned to normal range.

In step 1718, the method notifies the user (e.g. via a user notification message 111) to cease activity, sit down if possible and drink water. In step 1720, the method determines whether the BP measurements have returned within normal ranges after the standard timeframe. If the BP has returned to normal within the timeframe, the method notifies the user in step 1724 that the BP has normalized/returned to normal range. Otherwise, the method transitions to step 1722 and notifies the user to remain sitting if possible and consider consulting a cardiologist.

Figure 13:
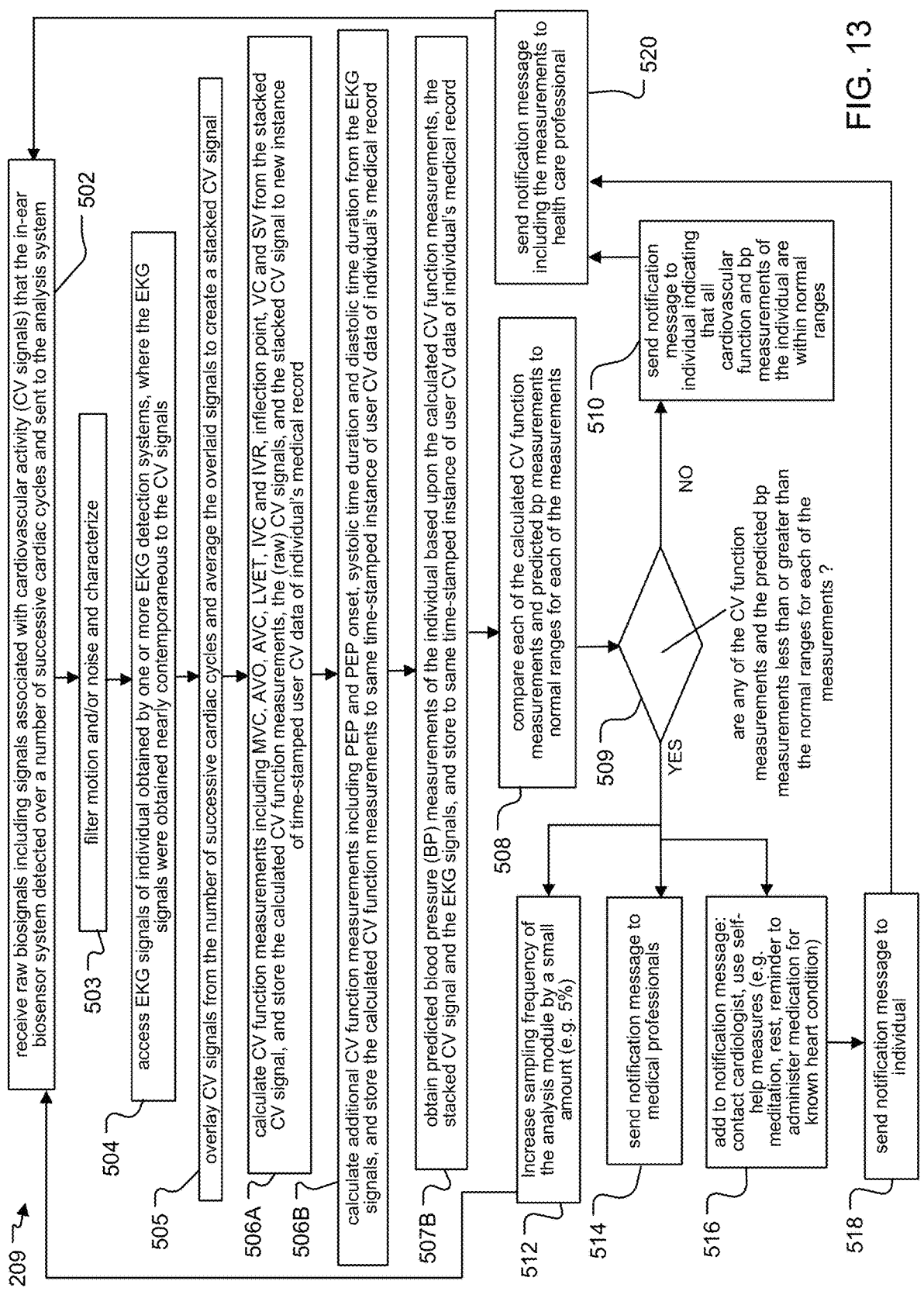
FIG. 13 is a flow diagram that illustrates a method of operation of the data analysis system in the CV monitoring system of FIG. 1B, where the method has similar steps as and operates in a similar way as the method of FIG. 7 for the system of FIG. 1A.

FIG. 13 is a flow diagram that describes another method of operation of the data analysis system 209. The method has similar steps as and operates in a similar way as the method of FIG. 7. However, this method describes operation of the CV monitoring system 10B in FIG. 1B. Here, the data analysis system 209 calculates CV function measurements from the detected CV signals 101 as in the method of FIG. 7, and calculates additional CV function measurements from the EKG signals 24 detected by and sent from one or more of the EKG detection systems in FIG. 1B. The data analysis system 209 can then use the calculated CV function measurements in conjunction with the additional CV function measurements to predict BP measurements for individuals 100.

Steps 502 and 503 are the same as in FIG. 7 for detecting biosignals including CV signals and filtering motion and/or noise from the biosignals, and characterizing the biosignals as being CV signals 101 or pressure signals.

In step 504, the analysis module 180 accesses EKG signals 24 of the individual 100 obtained by one or more EKG detection systems 18. The EKG signals 24 that the analysis module 180 accesses could be EKG signals 24 received by the analysis module 180 in real-time, or previously obtained and stored EKG signals 24 from the user CV data 950 or baseline CV data 930 of the individual's medical record 50. For optimum accuracy, the EKG signals should be obtained nearly contemporaneous to the CV signals 101, such as within 30 minutes or less. For this purpose, the analysis module 180 can compare a time stamp of the EKG signals 24 to that of the CV signals 101.

Step 505 is the same as in FIG. 7 for creating a stacked signal 101S from the CV signals 101. Step 506A is the same as in FIG. 7 for calculating CV function measurements from the stacked CV signal 101S and storing the calculated CV function measurements 954 to a new instance of time-stamped user CV data 950 of the individual's medical record 50. Here, the format of the user CV data 950/baseline CV data 930 is shown in FIG. 5B.

In step 506B, the method calculates additional CV function measurements 954 including PEP 206 and PEP onset 205, systolic time duration 304 and diastolic time duration 302 from the EKG signals 24. The method then stores the additionally calculated CV function measurements to the same time-stamped instance of user CV data 950 of the individual's medical record 50 that was created in step 506A.

Step 507B obtains predicted BP measurements of the individual 100 based upon the calculated CV function measurements 954, the stacked CV signal 101S and the EKG signals 24, and stores the predicted BP measurements to the same time-stamped instance of user CV data 950 created in step 506A.

Remaining steps 508, 509, 510, 512, 514, 516, 518, and 520 are the same as the correspondingly numbered steps in the method of FIG. 7 and operate in a substantially similar way. However, there may be somewhat different implementations for some of these steps because of the additional CV function measurements calculated in step 507B.

FIG. 14A is a flow diagram that provides more detail for step 506B in the method of FIG. 13. The diagram shows how the data analysis system 209 calculates CV function measurements based upon the CV signals 101, and can calculate additional CV function measurements 954 from the ECG signals 24 detected by and sent from one of the EKG detection systems in FIG. 1B. Typically, the method is performed by the data analysis module 180 of the data analysis system 209.

The first step is 506A. This is identical to step 506A in the method of FIG. 7 for calculating CV function measurements 954 based upon the CV signals 101 and storing the calculated CV measurements 954 to a new time-stamped instance of user CV data 950.

In step 1402, the analysis module 180 characterizes the EKG signals 24. In one example, this is accomplished by detecting and storing time points associated with P, Q, R, S and T complexes in the EKG signals 24. In step 1404, the method calculates the systolic time duration 304 by identifying the time between the R peak in the EKG signals and the AVC 203 of the calculated CV function measurements 954. According to step 1406, the method calculates the diastole 302 by determining a difference between successive R complex peaks in the EKG signals 24 and the systolic time duration 304. the time between the R peak in the EKG signals and the AVC 203 of the calculated CV function measurements 954. In step 1408, the method calculates the PEP onset 205 by identifying the timepoint of the Q complex in the EKG signals 24.

According to step 1410, the method calculates the PEP 206 by determining the time between the PEP onset 205 and the AVO 202 of the calculated CV function measurements 954. Then, in step 1412, the method stores the calculated systolic time duration 304, diastolic time duration 302, PEP onset 205 and PEP 206 additional CV function measurements 954 to the instance of user CV data 950 created in step 506A.

FIG. 14B provides more detail for step 507B in the method of FIG. 13.

The method has substantially similar structure and steps as in the method of FIG. 10, Specifically, steps 970, 974, 976, 978, 980, 982, and 984 are common to FIG. 10 and FIG. 14B. In contrast, method step 972A in FIG. 10 is replaced with step 972B in FIG. 14B.

The method of FIG. 14B operates as follows. The analysis module 180 accesses stacked signals and calculated CV function measurements 954 for multiple individuals in step 970, and transitions to step 972B.

In step 972B, the analysis module 180 selects at least some of the calculated CV function measurements (e.g. AVO 202, AVC 203, systolic peak 218, diastolic peak 220 and inflection point 222, as well as PEP 206, PEP onset 205, diastolic time duration 302 and systolic time duration 304) of the multiple individuals 100 to use as input to a preexisting machine learning model that was previously trained (i.e. created) by the data analysis system 209.

The method then transitions to steps 974, 976, 978, 980, 982, and 984 in sequence to obtain the predicted BP measurements.

In one implementation, the training data includes anonymized versions of calculated CV function measurements 954 and/or raw CV signals 101 copied from the medical records 50 of multiple individuals 100, along with corresponding reference BP measurements of the multiple individuals 100 obtained from one or more reference BP monitoring systems. In another implementation, the training data might include CV function measurements 954 and corresponding BP measurements, calculated from synthetic waveforms generated from one or more blood pressure models. In both of these implementations, the calculated CV function measurements include the additional CV function measurements calculated by the analysis module 209 using the EKG signals 24, or alternatively in conjunction with the measurements obtained using the EKG signals 24. These additional measurements include the PEP 206, PEP onset 205, diastolic time duration 302 and systolic time duration 304.

Figure 14C:
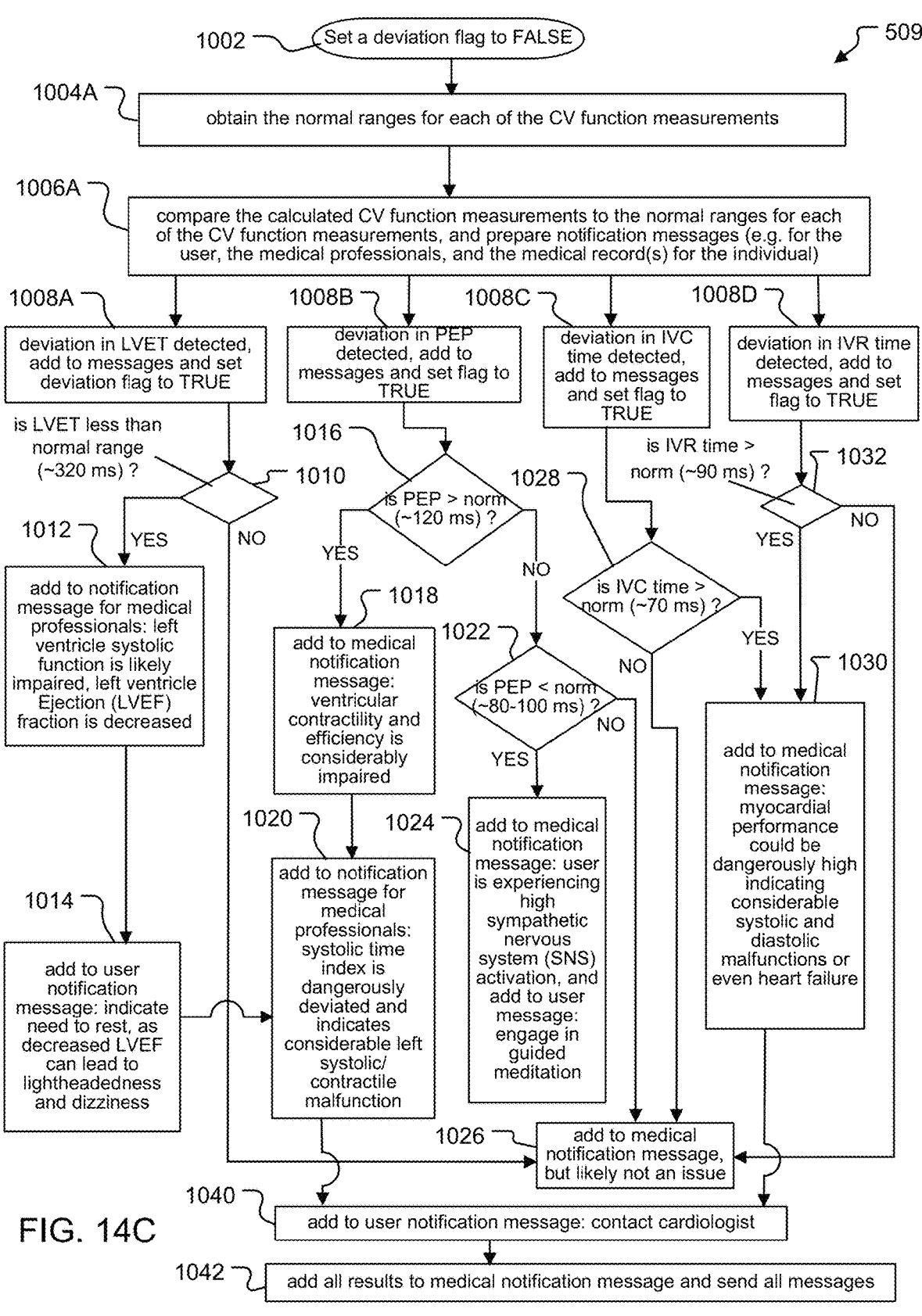
FIG. 14C is a flow diagram that provides more detail for the method of FIG. 13, where the diagram shows how the data analysis system compares the calculated CV function measurements for an individual to normal ranges for each the measurements and notifies the individual and medical professionals in response to the comparisons.

FIG. 14C describes a method for implementing step 509 in the method of FIG. 13. The method is similar in structure to and includes all steps of the method of FIG. 12A. FIG. 14B also includes a processing path that is not included in FIG. 12A.

As in the method of FIG. 12A, the method of FIG. 14C starts at step 1002 by obtaining normal ranges 932 for each of the CV function measurements 954, and compares the calculated CV function measurements 954 to the normal ranges 932 (e.g. standard and individual-specific normal ranges) for each of the CV function measurements 954 in step 1006A. The method prepares notification messages, and in steps 1008A, 1008C, and 1008D describes details of deviation processing for the LVET 208, IVC period 207, and IVR period 209, respectively. In addition, the method of FIG. 14C includes step 1008B for processing a detected deviation in the PEP 206. The details in the deviation processing are other defined qualifying criteria that the analysis module 180 can use in conjunction with the normal range comparisons to determine whether heart conditions of the individual exist, and whether to send notifications 111 to the individuals 100 and/or to the medical professionals 110 in response.

In step 1008B, the method detects a deviation in the PEP 206, adds the information to the notification messages 111 and sets the deviation flag to TRUE. In step 1016, the method determines whether the PEP 206 is greater than its normal range (e.g. −120 ms). If this statement is true, the method transitions to step 1018; otherwise, the method transitions to step 1022.

In step 1018, the method adds information to the medical notification message, indicating that ventricular contractility and efficiency is considerably impaired. The method then transitions to step 1020. In step 1022, the method determines whether the PEP 206 is less than its normal range 932. If this statement is true, the method transitions to step 1024; otherwise, the method transitions to step 1026.

In step 1024, the method adds information to the medical notification message 111. This information suggests that the user is experiencing high sympathetic nervous system (SNS) activation. The method also adds information to a user notification message that instructs the user to engage in guided meditation or other relaxation technique.

Steps 1020, 1026, 1404, and 1402 are the same as the steps having the same number in FIG. 12A. As a result, the method completes traversal of its path starting at step 1008B by executing steps 1020, 1040, and 1042 in sequence, or by executing step 1026.

Figure 15:
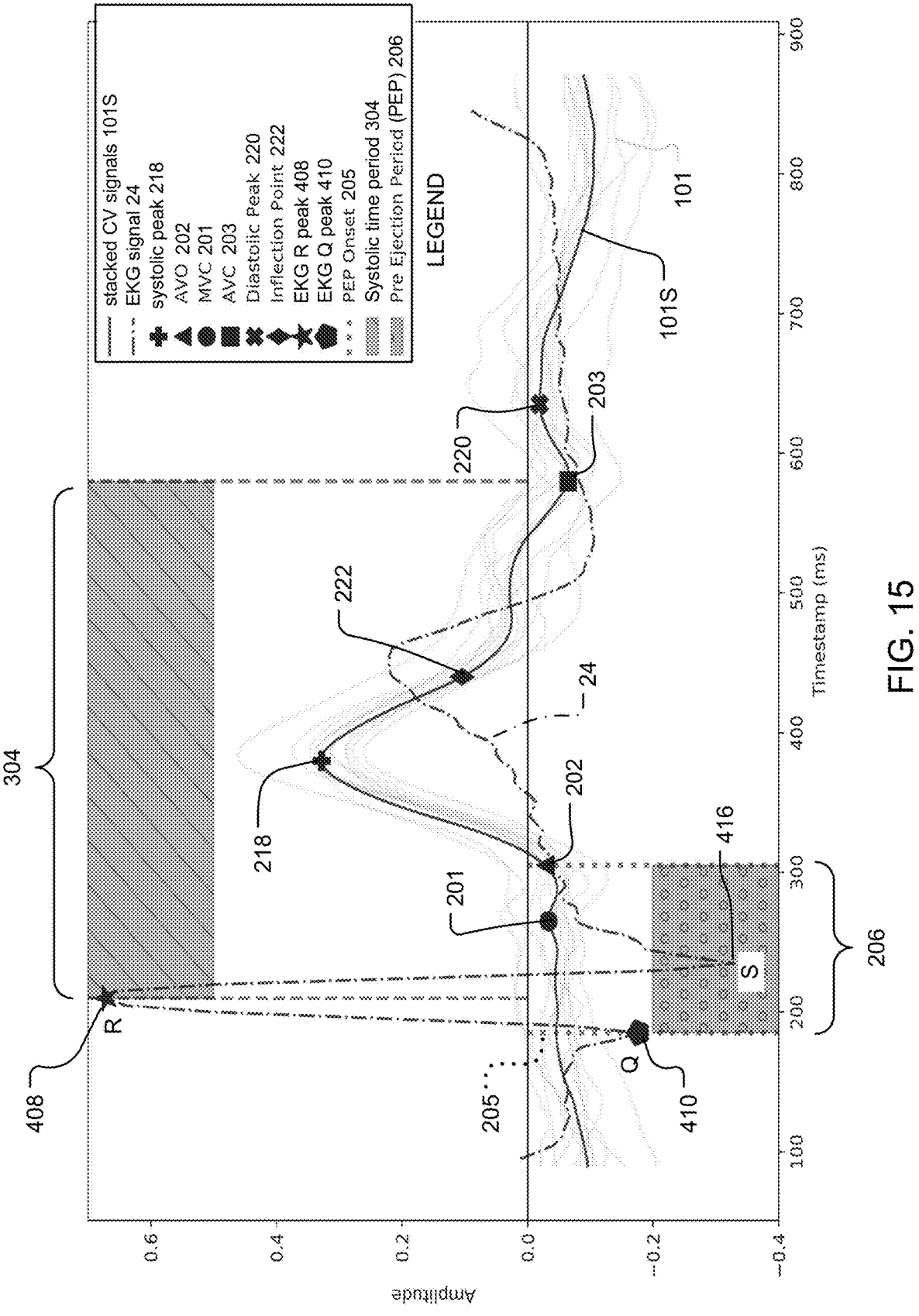
FIG. 15 is a plot of CV signals and an associated stacked CV signal as in FIG. 11 that further illustrates operation of the method of FIG. 13, and also illustrates operation of the flow diagram of FIG. 14A.

FIG. 15 is a plot of CV signals and an associated stacked CV signal 101S as in FIG. 11. The figure further illustrates operation of the method of FIG. 13 and operation of the flow diagram of FIG. 14A. In the illustrated example, a stacked CV signal 101 and an EKG signal 24 from one of the EKG detection systems 18 are shown on the same time scale. The figure shows the same CV function measurements 954 as in FIG. 11. Additional CV function measurements 954 that can be calculated in FIG. 15 based upon the EKG signal 24 and/or in conjunction with the measurements obtained from the CV signals 101 include the PEP 206, PEP onset 205, the systolic time duration 304, and the diastolic time duration 302 (not shown). Other measurements associated with the EKG signal 24 include an EKG R peak 408, EKG Q peak 410 and S value 416. The measurements 408, 410, and 416 are also indicated by capital letters R, Q, and S in the diagram, respectively.

FIG. 16A is a flow diagram that describes another implementation for how the analysis module 180 of the data analysis system 209 can use machine learning to predict BP measurements of an individual 100.

In step 1604, the analysis module 180 uses training data to train (i.e. create) the machine learning model 187. The model 187 might be any of the following types: random forest regressor, boosted decision trees, K-nearest neighbors (KNN), support vector machine (SVM) or a neural network such as a convolutional neural network (CNN), in examples.

Here, the training data at least includes reference BP measurements of multiple individuals 100 obtained from one or more reference BP monitoring systems. In one example, the training data additionally includes anonymized versions of biometric data 904 and baseline CV data 950 from the medical records 50 of multiple individuals 100. In another example, the training data additionally includes raw CV signals 101 and/or calculated CV function measurements 954 of multiple individuals 100, copied from the medical records 50 of the individuals, along with corresponding reference bp measurements of the same individuals 100 obtained from one or more reference BP monitoring systems.

According to step 1606, the analysis module 180 accesses recently calculated CV function measurements 924 and biometric data 904 from user CV data 950 of a new individual's medical record 50. This individual is "new" in that their user CV data 950 was not included in the training data used to train/create the machine learning model 187. In step 1608, the analysis module 180 applies the recent biometric data 904 and the recently calculated CV function measurements of the new individual 100 as input to the machine learning model to obtain predicted BP function measurements of the individual 100 as the output. In step 1610, the analysis module 180 stores the predicted BP measurements to the user CV data 950 of the individual's medical record 50.

FIG. 16B is a flow diagram that describes yet another implementation for how the analysis module 180 of the data analysis system 209 can use machine learning to predict the BP measurements of an individual 100.

As in FIG. 16A, the data analysis system 209 creates a machine learning model 187 using training data from the repository 70, and applies recently or newly calculated CV function measurements for a new individual as input to the (trained) model. The output of this operation is the predicted BP measurements for the individual 100.

When creating/training the model 187, however, the data analysis system 209 uses different training data than the training data used in FIG. 16A. Here, the training data is derived from one or more blood pressure models. The blood pressure models can be standard blood pressure models or blood pressure models that the data analysis system 209 creates/calculates.

More detail for the creation of the training data used to create the model 187 and the ability of the CV monitoring system 10B to obtain predicted BP measurements of individuals 100 using the model 187 is provided in the steps below, beginning with step 1620.

According to step 1620, the analysis module 180 accesses various standard blood pressure models such as a 3-component Windkessel model or a simulated pulse wave model, in examples. Alternatively, the analysis module 180 might create an accurate blood pressure model based on user CV data 950 of one or more selected individuals 100, where the created model can generate synthetic waveforms within acceptable error range compared to the user CV data 950. The training data is then derived from the created blood pressure model.

In step 1624, the analysis module 180 validates the standard or the calculated/created blood pressure models using reference CV function measurements obtained from various existing medical diagnostics systems. These systems include an EKG system, a doppler-based system and a PPG system, in examples. In step 1626, the analysis module 180 generates synthetic data based on the validated models and calculates CV function measurements 954 from the synthetic data.

According to step 1628, the analysis module 180 uses the CV function measurements calculated from synthetic data to train (i.e. create) machine learning model 187. In examples, the model 187 might be of type Random Forest Regression, Boosted Decision Trees or neural network such as a CNN, in examples.

In step 1630, the data analysis module 180 accesses recently stored or newly calculated CV function measurements 952 for an individual 100. Then, in step 1632, the analysis module 180 applies the calculated CV function measurements 952 as input to the machine learning model 187 to obtain predicted BP measurements for the individual 100 as the output. The analysis module 180 stores the predicted BP measurements to the user CV data 950 of the individual's medical record 50 in step 1634.

While this invention has been particularly shown and described with references to preferred embodiments thereof, it will be understood by those skilled in the art that various changes in form and details may be made therein without departing from the scope of the invention encompassed by the appended claims.

What is claimed is:

1. A cardiovascular monitoring and reporting system, the system comprising:

an in-ear biosensor system that includes at least one earbud configured to be placed at or within an ear canal of an individual, the at least one earbud including one or more infrasound/vibration sensors that are configured to detect cardiovascular signals (CV signals) from the individual over a number of successive cardiac cycles; and a data analysis system that receives the CV signals over the number of successive cardiac cycles from the biosensor system, creates a stacked CV signal as a function of the CV signals over the number of successive cardiac cycles, calculates cardiovascular function measurements (CV function measurements) of the individual from the stacked CV signal, and predicts blood pressure measurements (BP measurements) of the individual based upon the calculated CV function measurements and the stacked CV signal.

2. The system of claim 1, wherein the data analysis system creates the stacked CV signal by overlaying and averaging the CV signals over the number of successive cardiac cycles.

3. The system of claim 1, wherein the data analysis system calculates a stroke volume CV function measurement from the stacked CV signal and other CV function measurements calculated from the stacked CV signal.

4. The system of claim 1, wherein the data analysis system predicts the BP measurements of the individual based upon the calculated CV function measurements and the stacked CV signal of the individual, and based upon calculated CV function measurements and stacked CV signals of multiple other individuals.

5. The system of claim 1, wherein the predicted BP measurements include hypertension and hypotension.

6. The system of claim 1, further comprising an EKG detection system included within the at least one earbud.

7. The system of claim 1, further comprising:

an EKG detection system worn by the individual that detects EKG signals of the individual over a series of consecutive heart cycles that are nearly contemporaneous to a time period during which the CV signals over the number of successive cardiac cycles were obtained;

wherein the data analysis system receives the EKG signals over the series of consecutive heart cycles from the EKG detection system, and calculates additional CV function measurements from the EKG signals.

8. The system of claim 7, wherein the data analysis system calculates the additional CV function measurements from the EKG signals and from some of the CV function measurements calculated from the stacked CV signal.

9. The system of claim 7, wherein the data analysis system predicts at least some of the BP measurements based upon the CV function measurements calculated from the stacked CV signal, and from the additional CV function measurements calculated from the EKG signals.

10. The system of claim 7, wherein the data analysis system predicts the BP measurements of the individual based upon the calculated CV function measurements and the stacked CV signal of the individual and upon the additionally calculated CV measurements of the individual, and based upon calculated CV function measurements and stacked CV signals of multiple other individuals and upon additionally calculated CV function measurements of the multiple other individuals.

11. A method for monitoring cardiovascular health of an individual, the method comprising:

detecting cardiovascular signals (CV signals) over a number of successive cardiac cycles from the individual, via one or more infrasound/vibration sensors included within at least one earbud of an in-ear biosensor system worn by the individual;

creating a stacked CV signal as a function of the CV signals over the number of successive cardiac cycles;

calculating cardiovascular function measurements (CV function measurements) of the individual based upon the stacked CV signal; and predicting blood pressure measurements (BP measurements) of the individual based upon the stacked CV signal and the calculated CV function measurements.

12. The method of claim 11, wherein creating the stacked CV signal as a function of the CV signals over the number of successive cardiac cycles comprises overlaying and averaging the CV signals over the number of successive cardiac cycles into the stacked CV signal.

13. The method of claim 11, wherein the calculating CV function measurements of the individual based upon the stacked CV signal comprises calculating a stroke volume CV function measurement from the stacked CV signal and from other CV function measurements calculated from the stacked CV signal.

14. The method of claim 11, further comprising predicting the BP measurements of the individual additionally based upon calculated CV function measurements and stacked CV signals of multiple other individuals.

15. The method of claim 11, wherein the predicted BP measurements include hypertension and hypotension.

16. The method of claim 11, further comprising detecting EKG signals of the individual via an EKG detection system included within the at least one earbud.

17. The method of claim 11, further comprising:

detecting EKG signals of the individual from an EKG detection system worn by the individual, the EKG signals being obtained over a series of consecutive heart cycles that are nearly contemporaneous to a time period during which the CV signals over the number of successive cardiac cycles were obtained; and receiving the EKG signals over the series of consecutive heart cycles from the EKG detection system, and calculating additional CV function measurements from the EKG signals.

18. The method of claim 17, further comprising calculating the additional CV function measurements from the EKG signals and from some of the CV function measurements calculated from the stacked CV signal.

19. The method of claim 17, further comprising predicting at least some of the BP measurements based upon the CV function measurements calculated from the stacked CV signal, and from the additional CV function measurements calculated from the EKG signals.

20. The method of claim 17, further comprising predicting the BP measurements of the individual based upon the calculated CV function measurements and the stacked CV signal of the individual and upon the additionally calculated CV measurements of the individual, and based upon calculated CV function measurements and stacked CV signals of multiple other individuals and upon additionally calculated CV function measurements of the multiple other individuals.

21. A multi-user cardiovascular monitoring and reporting system, the system comprising:

in-ear biosensor systems worn by individuals that each include at least one earbud configured to be placed at or within ear canals of the individuals, wherein the at least one earbud of each of the in-ear biosensor systems includes an infrasound/vibration sensor that is configured to detect cardiovascular signals (CV signals) over a number of successive cardiac cycles from each of the individuals; and a data analysis system that, for each of the individuals, receives the CV signals over the number of successive cardiac cycles from each of the biosensor systems, overlays and averages the CV signals into a stacked CV signal for each of the individuals, calculates cardiovascular function measurements (CV function measurements) of each individual from the stacked CV signal for each individual, and predicts blood pressure measurements (BP measurements) of each individual based upon the calculated CV function measurements and the stacked CV signal of each individual.

22. The system of claim 21, wherein the data analysis system predicts the BP measurements of each individual based upon the calculated CV function measurements and the stacked CV signal of each individual, and based upon the calculated CV function measurements and the stacked CV signals of multiple other individuals.

23. The system of claim 21, further comprising:

EKG detection systems worn by each of the individuals that obtain EKG signals of the individuals over a series of consecutive heart cycles that are nearly contemporaneous to a time period during which the CV signals over the number of successive cardiac cycles of each of the individuals were obtained;

wherein the data analysis system receives the EKG signals over the series of consecutive heart cycles from each of the EKG detection systems, and calculates additional CV function measurements for each of the individuals from the EKG signals obtained from each of the individuals.

24. The system of claim 23, wherein the data analysis system predicts at least some of the BP measurements for each of the individuals based upon the CV function measurements calculated from the stacked CV signal of each individual and from the additional CV function measurements calculated from the EKG signals from each individual.

25. The system of claim 23, wherein the data analysis system predicts the BP measurements of each of the individuals based upon the calculated CV function measurements and the stacked CV signal of each individual and upon the additionally calculated CV measurements of each individual, and based upon calculated CV function measurements and stacked CV signals of multiple other individuals and upon the additionally calculated CV function measurements of the multiple other individuals.

\* \* \* \* \*